US006115673A

United States Patent [19]
Malin et al.

[11] Patent Number: 6,115,673
[45] Date of Patent: Sep. 5, 2000

[54] METHOD AND APPARATUS FOR GENERATING BASIS SETS FOR USE IN SPECTROSCOPIC ANALYSIS

[75] Inventors: Stephen F. Malin; Kevin H. Hazen, both of Phoenix, Ariz.

[73] Assignee: Instrumentation Metrics, Inc., Tempe, Ariz.

[21] Appl. No.: 08/911,588

[22] Filed: Aug. 14, 1997

[51] Int. Cl.$^7$ .................................................. G01J 3/28
[52] U.S. Cl. .............................................. 702/23; 702/30
[58] Field of Search .................................. 702/22, 23, 24, 702/25, 26, 27, 28, 29, 30, 31, 32; 356/300, 302, 303, 345, 346; 378/44, 45, 47

[56] References Cited

U.S. PATENT DOCUMENTS

| | | | |
|---|---|---|---|
| 4,893,253 | 1/1990 | Lodder | 364/497 |
| 5,308,982 | 5/1994 | Ivaldi et al. | 250/339.01 |
| 5,348,002 | 9/1994 | Caro | 128/633 |
| 5,518,694 | 5/1996 | Bentsen | 422/82.08 |
| 5,606,164 | 2/1997 | Price et al. | 250/339.09 |
| 5,655,530 | 8/1997 | Messerschmidt | 128/633 |
| 5,743,262 | 4/1998 | Lepper, Jr. et al. | 128/633 |
| 5,747,806 | 5/1998 | Khalil et al. | 250/339.12 |
| 5,823,951 | 10/1998 | Messerschmidt | 600/322 |
| 5,830,132 | 11/1998 | Robinson | 600/310 |
| 5,876,121 | 3/1999 | Burns et al. | 374/161 |

FOREIGN PATENT DOCUMENTS

| | | | |
|---|---|---|---|
| 419222 A2 | 3/1991 | European Pat. Off. | G01N 21/35 |
| WO96/32631 | 10/1996 | WIPO | G01N 21/27 |
| WO97/06418 | 2/1997 | WIPO | G01J 3/457 |

OTHER PUBLICATIONS

Arnold et al., "Determination of Physiological Levels of Glucose in an Aqueous Matrix with Digitally Filtered Fourier Transform Near-Infrared Spectra," Anal. Chem., 1990, 62.

Arnold et al., Ohio University, spectroscopic–based glucose sensors no date.

Small et al., "Strategies for Coupling Digital Filtering with Partial Least–Squares Regression: Application to the Determination of Glucose in Plasma by Fourier Transform Near–Infrared Spectroscopy," Anal. Chem., 1993, 65.

Hazen et al., "Temperature–Insensitive Near–Infrared Spectroscopic Measurement of Glucose in Aqueous Solutions," Applied Spectroscopy, vol. 48, No. 4, 1994.

Hazen, "Glucose Determination in Biological Matrices Using Near–Infrared Spectroscopy," University of Iowa Thesis, Aug. 1995.

*Primary Examiner*—Marc S. Hoff
*Assistant Examiner*—Craig Steven Miller
*Attorney, Agent, or Firm*—Michael A. Glenn

[57] ABSTRACT

One or more basis sets are applied to a spectroscopic signal during analysis to produce an accurate spectral representation from which analyte concentration may be accurately determined. A basis set includes all interfering components found in a sample, such as serum. With regard to an analyte, such as glucose, it is necessary to define those components of a sample that have a larger interference than that of glucose. A basis set may be generated, for example, that produces a transform for the red blood cells that interfere or scatter the light; and also for skin effects. Once the spectra of all these components is known, it is then necessary to determine how each of these components interact, e.g. taking serum data, extracting each of the components, and then comparing the spectra for the individual components with that of the components in solution. The invention characterizes each component in a sample, as well as all other possible interferants and, after producing an accurate representation of each component at each frequency of interest, identifies and subtracts each interferant from the spectra produced at the frequency of interest. The basis sets may take the form of transforms that may be stored in a look-up table for use during analysis.

47 Claims, 37 Drawing Sheets

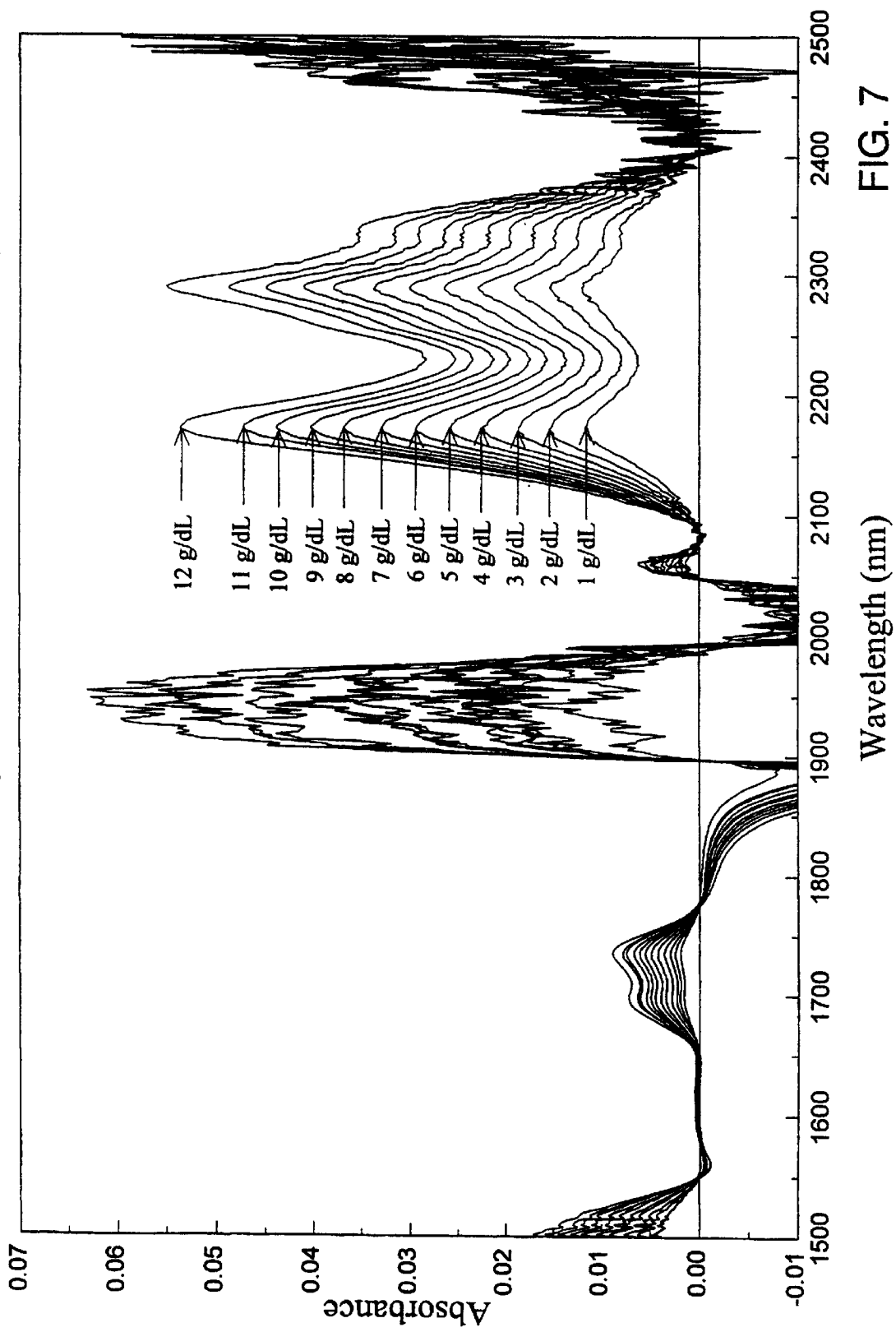

METHOD AND APPARATUS FOR GENERATING BASIS SETS FOR USE IN SPECTROSCOPIC ANALYSIS

BACKGROUND OF THE INVENTION

1. Technical Field

The invention relates to determining the concentration of a target analyte in a sample. More particularly, the invention relates to a method and apparatus for generating basis sets for use in determining the concentration of a target analyte in a sample, for example using multi-spectral analysis.

2. Description of the Prior Art

Data analysis during spectroscopic analysis refers to the process of finding optimum wavelengths and generating accurate calibrations to relate a given set of spectroscopic data to reference laboratory values for the composition of a set of samples, such that it is possible to analyze, i.e. predict, the values of future samples of unknown composition. Calibration of spectroscopic instruments that are used to perform spectroscopic measurements is typically accomplished by application of multiple regression of the absorbance at some number of wavelengths against the reference laboratory values, i.e. mathematically determining the best possible fit of a straight line to a set of data (see, for example, H. Mark, *Principles and Practice of Spectroscopic Calibration*, John Wiley & Sons, Inc. (1991)).

An error free calibration, i.e. a sample for which Beer's law applies, is one in which the constituent of interest, and which is the only constituent in the sample, is dissolved in a completely nonabsorbing solvent, and has only a single absorbance band. In this case, the concentration of the constituent is known exactly over a broad range for the set of calibration samples; and the spectrometer has no noise, nonlinearity, or other fault. In such an idealized case, the height of the absorbance peak is strictly proportional to the concentration of the constituent. Thus, it is possible to calibrate a system using only two samples because two points determine the line, and the slope of the line and intercept of data are readily determined using known mathematical formulae.

Unfortunately, the ideal case does not prevail in the real world. For example, spectroscopic measurements are subject to such phenomena as skew in the data, which is caused by physical changes in the instrument, sample, or experiment. For example, interfering and/or dominating constituents in the sample other than the constituent of interest can affect the data. Temperature, medium, pathlength, and scattering effects must also be considered.

Near-infrared (near-IR) absorbance spectra of liquid samples contain a large amount of information about the various organic constituents of the sample. Specifically, the vibrational, rotational, and stretching energy associated with organic molecular structures (e.g. carbon-hydrogen, oxygen-hydrogen, and nitrogen-hydrogen chemical bonds) produce perturbations in the near-IR region which can be detected and related to the concentration of various organic constituents present in the sample. However, in complex sample matrices, near-IR spectra also contain an appreciable amount of interference, due in part to similarities of structure amongst analytes, relative levels of analyte concentration, interfering relationships between analytes, and the magnitude of electronic and chemical noise inherent in a particular system. Such interference reduces the efficiency and precision of measurements obtained using near-IR spectrometry to determine the concentration of liquid sample analyses.

For example, temperature is a critical parameter for near-IR spectroscopic analysis of aqueous based samples. Major water absorption bands are centered at approximately 3800, 5200, and 6900 nm, but the exact positions of these bands are temperature sensitive. These bands shift to higher frequencies at higher temperatures. Changes in temperature also alter the extent of water hydrogen bonding to other chemical species, which causes significant shifts in band positions. The large water content of most clinical samples, e.g. when determining glucose concentration in an aqueous solution, necessitates precise control of the sample temperature.

With regard to temperature, K. Hazen, M. Arnold, G. Small, Temperature-Insensitive Near-Infrared Spectroscopic Measurement of Glucose in Aqueous Solutions, Applied Spectroscopy, Vol. 48, No. 4, pp. 477–483 (1994) disclose the use of a digital Fourier filter that is combined with partial least squares (PLS) regression to generate a calibration model for glucose that is insensitive to sample temperature. The calibration model is initially created using spectra collected over the 5000 to 4000 nm spectral range with samples maintained at 37° C. The model is evaluated by judging the ability to determine glucose concentrations from a set of prediction spectra. Absorption spectra in the prediction set are obtained by ratioing single-beam spectra collected from solutions at temperatures ranging from 32° C. to 41° C. to reference spectra collected at 37° C. The temperature sensitivity of the underlying water absorption bands creates large baseline variations in the prediction spectra that are effectively eliminated by the Fourier filtering step.

See, also, G. Small, M. Arnold, L. Marquardt, Strategies for Coupling Digital Filtering with Partial Least-Squares Regression: Application to Determination of Glucose in Plasma by Fourier Transform Near-Infrared Spectroscopy, Analytical Chemistry, Vol. 65, No. 22, pp. 3279–3289 (1993) (Gaussian-shaped bandpass digital filters are implemented by use of Fourier filtering techniques and employed to preprocess spectra to remove variations due to the background absorbance of the [bovine] plasma matrix. PLS regression is used with the filtered spectra to compute calibration models for glucose); M. Arnold, G. Small, Determination of Physiological Levels of Glucose in an Aqueous Matrix with Digitally Filtered Fourier Transform Near-Infrared Spectra, Analytical Chemistry, Vol. 62, No. 14, pp. 1457–1464 (1990) (and G. Small, M. Arnold, Method and Apparatus for Non-Invasive Detection of Physiological Chemicals, Particularly Glucose, U.S. Pat. No. 5,459,317 (Oct. 17, 1995)) ( . . . A digital Fourier filter . . . removes both high-frequency noise and low-frequency base-line variations from the spectra. Numerical optimization procedures are used to identify the best location and width of a Gaussian-shaped frequency response function for this Fourier filter. A dynamic area calculation, coupled with a simple linear base-line correction, provides an integrated area from the processed spectra that is linearly related to glucose concentration . . . ); and K. Hazen, Glucose Determination in Biological Matrices Using Near-infrared Spectroscopy, Ph.D. Thesis, Univ. of Iowa (August 1995) (glucose determinations in water, serum, blood, and the body are performed using near-IR spectroscopy, multivariate analysis is used to correlate minor spectral variations with analyte concentrations.

A number of near-IR devices and methods have been described that may be used in connection with the foregoing techniques to provide noninvasive blood analyte determinations:

U.S. Pat. No. 5,360,004 to Purdy et al. describes a method and apparatus for the determination of blood analyte concentrations, wherein a body portion is irradiated with radiation containing two or more distinct bands of continuous-wavelength incident radiation. Purdy et al. emphasize filtration techniques to specifically block radiation at the two peaks in the near-IR absorption spectrum for water, occurring at about 1440 and 1935 nm. Such selective blocking is carried out in order to avoid a heating effect that may be due to the absorption of radiation by water in the body part being irradiated.

By contrast, U.S. Pat. No. 5,267,152 to Yang et al. describes noninvasive devices and techniques for measuring blood glucose concentration using only the portion of the IR spectrum which contains the near-IR water absorption peaks (e.g. the water transmission window, which includes those wavelengths between 1300 and 1900 nm), where water absorbance reaches a minimum at 1600 nm. Optically controlled light is directed to a tissue source and then collected by an integrating sphere. The collected light is analyzed and blood glucose concentration calculated using a stored reference calibration curve.

U.S. Pat. No. 5,606,164 to Price et al. describes a method and apparatus for measuring the concentration of an analyte present in a biological fluid, near-IR radiation is applied to calibration samples to produce calibration data. Unknown sample data is analyzed using data pretreatment followed by projection into the calibration model space with prediction of analyte concentration using the calibration model.

Devices have also been described for use in determination of analyte concentrations in complex samples, for example:

U.S. Pat. No. 5,242,602 to Richardson et al. describes methods for analyzing aqueous systems to detect multiple components. The methods involve determination of the absorbance or emission spectrum of the components over the range of 200 to 2500 nm, and application of chemometrics algorithms to extract segments of the spectral data obtained to quantify multiple performance indicators.

U.S. Pat. No. 5,252,829 to Nygaard et al. describes a method and apparatus for measuring the concentration of urea in a milk sample using an infrared attenuation measuring technique. Multivariate techniques are carried out to determine spectral contributions of known components using partial least squares algorithms, principal component regression, multiple linear regression or artificial neural network learning. Calibration is carried out by accounting for the component contributions that block the analyte signal of interest. Thus, Nygaard et al. describe a technique of measuring multiple analyte infrared attenuations and compensating for the influence of background analyses to obtain a more accurate measurement.

U.S. Pat. No. 4,975,581 to Robinson et al describes a method and apparatus for determining analyte concentration in a biological sample based on a comparison of infrared energy absorption (i.e. differences in absorption at several wavelengths) between a known analyte concentration and a sample. The comparison is performed using partial least squares analysis or other multivariate techniques.

U.S. Pat. No. 4,882,492 to Schlager describes a method and apparatus for noninvasive determination of blood analyte concentrations. Modulated IR radiation is directed against a tissue sample (e.g. an ear lobe) and either passed through the tissue or impinged on a skin surface where it is spectrally modified by a target analyte (glucose). The spectrally modified radiation is then split, wherein one portion is directed through a negative correlation cell and another through a reference cell. Intensity of the radiation passing through the cells are compared to determine analyte concentration in the sample.

U.S. Pat. No. 4,306,152 to Ross et al. describes an optical fluid analyzer designed to minimize the effect of background absorption (i.e. the overall or base level optical absorbance of the fluid sample) on the accuracy of measurement in a turbid sample or in a liquid sample which is otherwise difficult to analyze. The apparatus measures an optical signal at the characteristic optical absorption of a sample component of interest and another signal at a wavelength selected to approximate background absorption, and then subtracts to reduce the background component of the analyte dependent signal.

U.S. Pat. No. 4,893,253 to Lodder describes a method for analyzing intact capsules and tablets by using near-infrared reflectance spectroscopy. The method detects adulterants in capsules by obtaining spectra for a training set of unadulterated samples, representing each spectrum as a point in a hyperspace, creating a number of training set replicates and a bootstrap replicate distribution, calculating the center of the bootstrap replicate distribution, obtaining a spectrum for an adulterated sample, transforming the spectrum into a point in hyperspace, and identifying the adulterated sample as abnormal based on a relationship between the adulterated sampl's hyperspatial point and the bootstrap replication distribution. See, also, R. Rosenthal, L. Paynter, L. Mackie, Non-Invasive Measurement of Blood Glucose, U.S. Pat. No. 5,028,787 (Jul. 2, 1991) (A near-infrared quantitative analysis instrument and method non-invasively measures blood glucose by analyzing near-infrared energy following interactance with venous or arterial blood, or transmission through a blood containing body part.).

The accuracy of information obtained using the above described methods and devices is limited by the spectral interference caused by background, i.e. non-analyte, sample constituents that also have absorption spectra in the near-IR range. Appreciable levels of background noise represent an inherent system limitation particularly when very little analyte is present. In light of this limitation, attempts have been made to improve signal-to-noise ratios, e.g. by avoiding water absorption peaks to enable the use of increased radiation intensity, by reducing the amount of spectral information to be analyzed, or by using subtraction or compensation techniques based on an approximation of background absorption. As discussed above, these techniques have focused primarily upon examining all constituents of a spectra simultaneously. Although such techniques have provided some improvement, there remains a need to provide a method and apparatus for performing a more precise determination of the concentration of analytes, for example in a liquid matrix, i.e. where an accurate representation of each and every sample component is obtained during analysis.

SUMMARY OF THE INVENTION

The invention provides one or more basis sets that are applied to a spectroscopic signal during analysis to produce an accurate spectral representation from which analyte concentration may be accurately determined. The presently preferred embodiment of the invention is applicable for the determination of such analytes as glucose in serum, as determined using non-invasive techniques. For example, in the basis sets, near-IR absorbance features over the 1100 to 2500 nm spectral region are provided for water, albumin protein, globulin protein, triacetin, cholesterol, BUN, and glucose. In addition, sample temperature effects are also included, along with instrument noise levels.

A basis set includes all interfering components found in a sample, such as serum. These components can include, for example, water, temperature/hydrogen bonding effects, albumin globulin protein, triglycerides, cholesterol, urea, and all organic components. The basis set also includes electrolytes, such as $Na^+$, $K^+$ and $Cl^-$.

The basis set does not include those components that do not interfere, such as anything that in terms of concentration is less than the background signal or noise level. With regard to an analyte, such as glucose, it is necessary to define those components of a sample that have a larger interference than that of glucose. Instead of considering only the analytes that are mentioned above, which are all in blood or serum, a basis set may be generated, for example, that produces a transform for the red blood cells that interfere or scatter the light; and also for skin effects.

Once the spectra of each of these components is known, it is then necessary to determine how the components interact, e.g. taking serum data, extracting each of the components, and then comparing the spectra for the individual components with that of the components in solution.

Thus, once a basis set is generated for glucose in the presence of water, it is determined that water interferes with glucose, and it is determined how to remove the water, then a basis set for a next component can be generated, such as for temperature effect. In the example of non-invasive glucose concentration determination, the invention sequentially adds basis sets for other components, e.g. globulin, protein, triglycerides, urea, or cholesterol, in the presence of water, to build up to a serum matrix. Once basis sets are generated for serum, it is then possible to generate basis sets for red blood cells, muscle layers, skin layers, fat layers, even the whole body.

It is significant to note that the basis set approach herein thus characterizes each component in a sample, as well as all other possible interferants and, after producing an accurate representation of each component at each frequency of interest, subtracts each interferant from the spectra produced at the frequency of interest. In this way, all interferants may be identified within the context of all other relevant sample components, and thence removed from the spectra, leaving substantially only the signal produced by the analyte of interest.

The various basis sets may be also combined mathematically to generate a set of transforms that may be stored in a look-up table for use during analysis. In this way, a fast real time determination of analyte concentration may be made using relatively simple, low power computer hardware, e.g. a low power embedded controller.

BRIEF DESCRIPTION OF THE DRAWINGS

FIG. 7 is a plot of absorbance vs. wavelength showing $albumin_{(aq)}$—buffer (pathlength corrected);

DETAILED DESCRIPTION OF THE INVENTION

Figure 1:
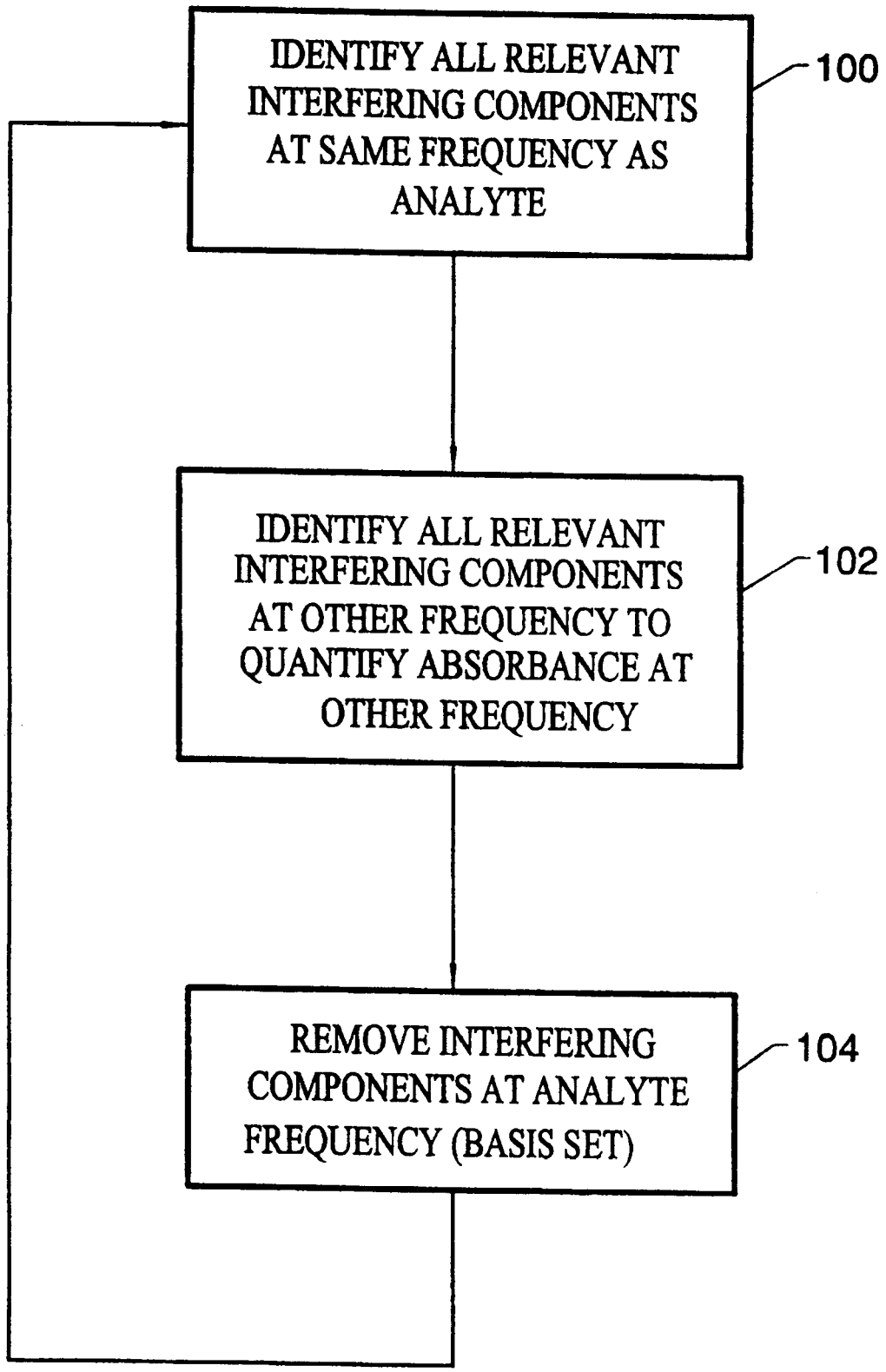
FIG. 1 is a flow diagram showing the generation of a basis set according to the invention.

The following discussion describes what the basis set is, how it is collected, the instrument that is required, the data collection parameters, the data analysis as far as such factors as temperature and path length are concerned, and what are considered to be additional basis sets.

The simplest example of a basis set is a basis set that includes all interfering components in a sample, such as serum. These components can include, for example, water, temperature/hydrogen bonding effects, albumin, and globulin protein, triglycerides, cholesterol, urea, all organic components, and $Na^+$, $K^+$, and $Cl^-$. To a lesser degree, the basis set may include additional electrolytes.

The basis set does not include those components that do not interfere, such as anything that in terms of concentration is less than the background signal or noise. With regard to an analyte, such as glucose, it is necessary to define those components of a sample that have a larger interference than that of glucose. Instead of considering only the analytes that are mentioned above, which are all in blood or serum, a basis set may be generated, for example, that produces a transform for the red blood cells that interfere or scatter the light; and also for skin effects.

Once the spectra of all these components is known, it is then necessary to determine how each of these components interact, e.g. taking serum data, extracting each of the components, and then comparing the spectra for the individual components with that of the components in solution.

Once a basis set is generated for glucose in the presence of water, it is determined that water interferes with glucose, and it is determined how to remove the water, then a basis set for a next component can be generated, such as for temperature effect. In the example of non-invasive glucose concentration determination, the invention sequentially adds basis sets for other components, e.g. globulin, protein, triglycerides, urea, or cholesterol, in the presence of water, to build up to a serum matrix. Once basis sets are generated for serum, it is then possible to generate basis sets for red blood cells, muscle layers, skin layers, fat layers, even the whole body.

It is significant to note that the basis set approach herein thus characterizes each component in a sample, as well as all other possible interferants, and subtracts each interferant from the spectra produced at the frequency of interest. In this way, all interferants are identified within the context of the sample and systematically from the spectra, leaving substantially only the signal produced by the analyte of interest.

The various basis sets may be combined mathematically to generate a set of transforms that may be stored in a look-up table for use during analysis. In this way, a fast, real time determination of analyte concentration may be made using relatively simple, low power computer hardware, e.g. a low power embedded controller.

Once it is determined which components are present in the sample, it is necessary to determine the best method of collecting spectra for these components. However, it is also necessary to define instrument specifications, such as signal to noise ratio, resolution, and wavelength reproducibility, before the spectra can be collected. These instrument considerations are discussed in detail below.

The procedure for generating basis sets is iterative. In some embodiments of the invention it is necessary to consider such factors as scatter correction, refractive index correction, depth of penetration into the tissue, total optical path length, and temperature. Once the basis sets are generated, they may be applied to a spectroscopic input signal. The signal thus processed by the basis sets is then preprocessed using standard chemometric techniques, such as smoothing and second derivative analysis.

Another approach to processing after application of the basis sets is that of deconvolution. If deconvolution is used, then it is necessary to perform temperature correction after the data collection and scatter correction. This approach uses the basis sets to identify and isolate various components of the sample in an iterative fashion. Thereafter, multivariate analysis may be applied, which may include partial least squares analysis or principal components analysis. Such processing is a matter of choice and is well known in the art. For example, in a glucose concentration C for which there is a spectra of interferograms n x m, where m is the number of interferograms and n is the number of interferogram points, a data reduction is performed, in which:

$$C = b_o + b_1 P_1 + \ldots b_n P_n; \quad (1)$$

where $P_i$ are PLS factor scores derived from the interferogram points and concentration values; and $b_i$ provides the regression coefficients.

Unique to the invention, various transforms such as deconvolution are performed with reference to the basis set. Pre-processing also relies on the basis set in the invention. For example, in the case of a Fourier filter in which certain frequencies pass through the filter, it is necessary to know what frequency the filter passed. In this way, it is possible to determine if the analyte is passed by the filter. The basis set is referenced to identify the analyte concentration at various frequencies, such that the Fourier filter only need be applied at those frequencies of interest, and not across a broad range of absorbance frequencies (as is practiced in the prior art). Thus, the basis set may loosely be thought of in this application as a filter for the filter.

Various molecular relations may be considered to be basis sets in themselves, such as carbon-hydrogen, oxygen-hydrogen, and nitrogen-hydrogen bonding. In such cases, there are more absorbance bands than can be accounted for by these fundamental components. This means that there are related effects for those portions of molecular structures to which these components are bonded. Thus, even though these molecules or pieces of molecules may be found in common among different constituents, it is possible to assign them to a constituent and then discard them during deconvolution because of the signature across the spectra of a particular constituent.

FIG. 1 is a flow diagram showing the generation of a basis set according to the invention. The first step of the process involves identifying relevant interfering components of the sample at the same frequency as that of the analyte (100). This step and subsequent steps may be performed using known spectroscopic and chemometric techniques, as is discussed in greater detail below. Once the interfering components are identified, the relevant interfering components are then all identified at other frequencies to quantify absorbance at these other frequencies (102). The interfering components, once quantified, are then removed at the frequency of the analyte (104). Each iteration of the foregoing steps may be described as a separate basis set. Thus, the invention produces a plurality of basis sets for an analyte.

Figure 2:
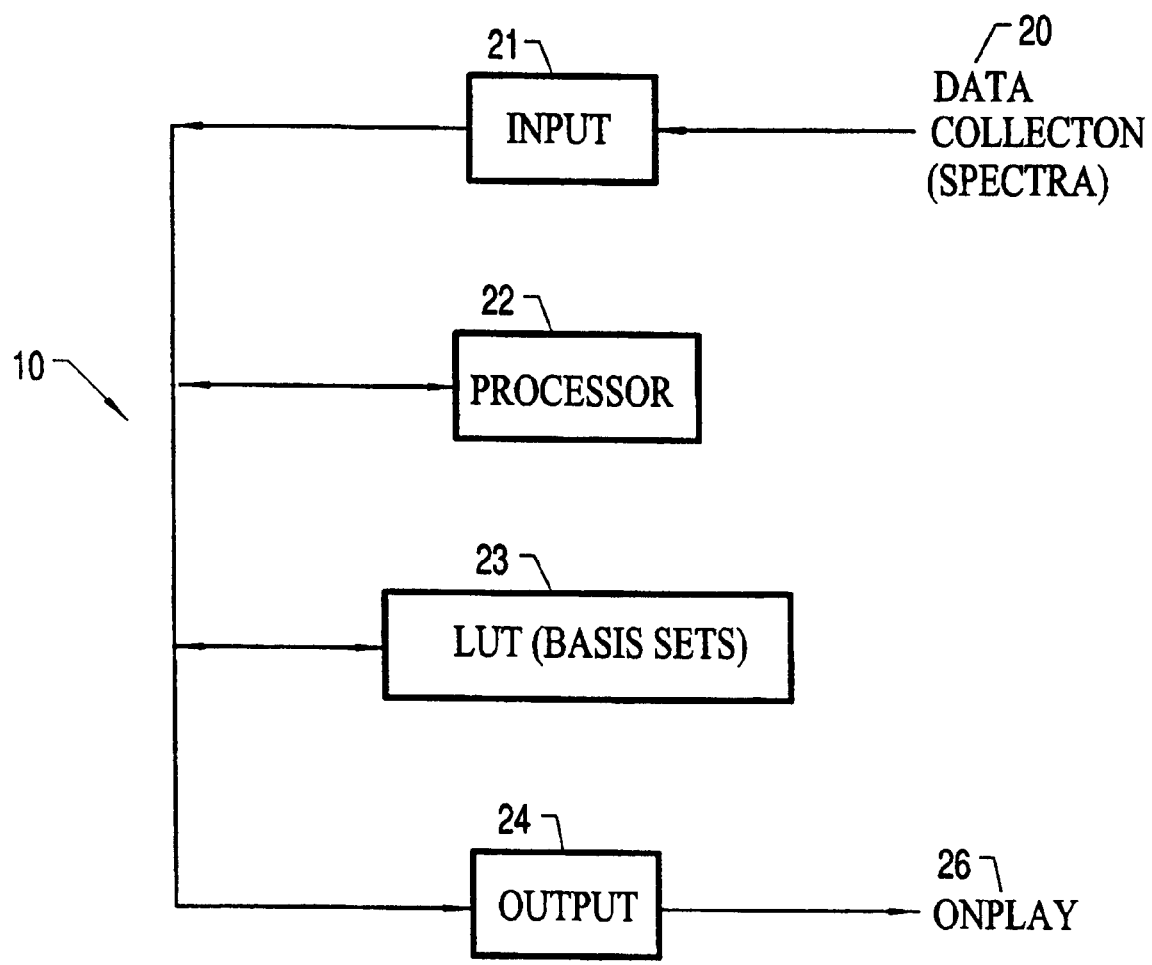
FIG. 2 is a block schematic diagram of an instrument that incorporates one or more basis sets according to the invention.

FIG. 2 is a block schematic diagram of an instrument that incorporates one or more basis sets according to the invention. In operation, a device 10, collects spectra 20 using standard or modified (see below) spectroscopic devices. The spectra are provided to the input port/buffer 21 of a system that includes a processor 22. The input port/buffer may include an analog-to-digital conversion function, such that spectral data collected by the spectroscopic device are converted to digital data. The processor operates upon such digital input data in accordance with various transforms stored in one or more look-up tables (LUTs). The LUTs contain transforms that incorporate the various basis sets. The transform process performed by the processor uses the basis sets to identify and remove substantially all interfering constituents from the spectral signal produced by the spectroscopic device. Once processing with regard to the basis sets is completed, the digital signal contains substantially only the analyte information. This information is then further processed in accordance with known spectroscopic calibration and chemometric techniques and provided to an output port/buffer 24. The output information may then be observed on a display 26, in any desired format, to provide an accurate indication of analyte concentration within the sample.

As also discussed both above and below, the basis sets generated in accordance with the invention herein may be stored in a lookup table or they may be mixed in with the other transform information. In producing such look-up tables, the basis sets first exist as matrix raw data collected during the iterative process of generating the several basis sets. In view of the several basis sets generated in the preferred embodiment of the invention, there may be different matrices in the look-up tables, or there may be a single matrix that generates a transform which is representative of all of the basis sets and that is applied directly to the raw data. Thus, one embodiment of the invention takes each of the components and builds them into a complex matrix that comprises an algorithm for identifying and removing interferants. In this way, the invention provides a system that accurately represents how the components appear within the spectra of interest when such components are all combined. It is this ability of the invention to identify each relevant component of a sample individually within the context of each other component that allows the ultimate determination of look-up table entries for an analyte of interest.

Although possible, the presently preferred embodiment of the invention does not provide spectra of glucose that has been corrected for all interferants at all concentration levels in a lookup table. Rather, there are a series of spectra of the analyte at certain different physiological concentrations of interest. For example, in the case of glucose, there are look-up basis set values for hypo- and hyperglycemia concentrations. Thus, the invention does not need to represent all of the information in all of the basis sets in the look-up tables. Rather, it is only necessary to represent information over the whole range of glucose that occurs in the body. The approach is taken for albumin protein, and other sample components. As discussed above, a single equation may be written for all of the spectral information in this matrix, or one or more look-up tables may be provided. In any event, this approach of storing only useful spectral information in the look-up tables reduces the memory and processing power requirements of the instrument.

As discussed more fully below, the basis sets are first generated and, thereafter, incorporated into an instrument for use during analysis. To determine those values that are to be put into the look-up tables it is necessary to go through any number of basis sets. As discussed above, it is necessary to identify the major interfering components that affect the analyte in the sample and generate basis sets for each and every one of these components.

Figure 3:
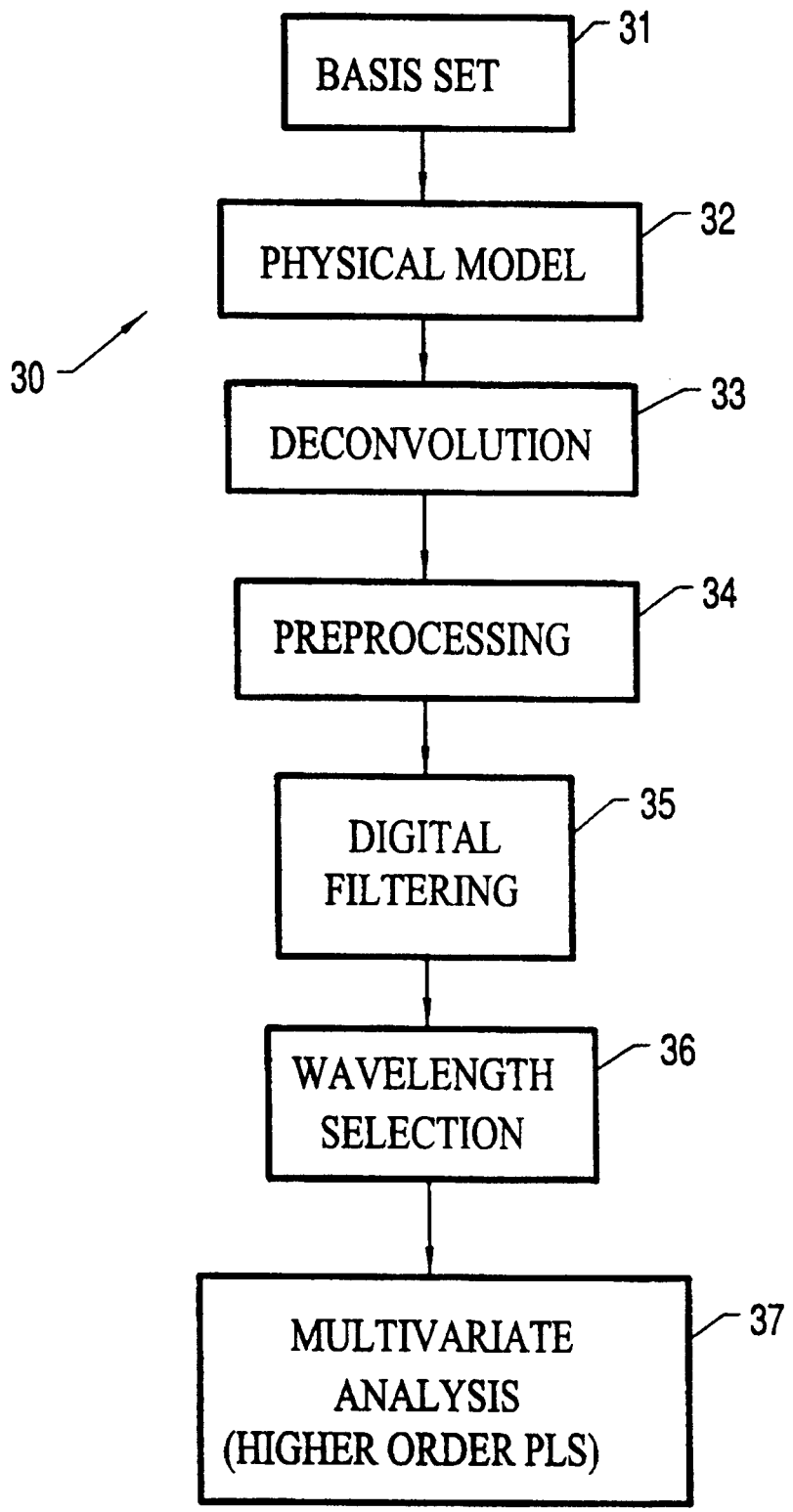
FIG. 3 is a block schematic diagram of an instrument that implements an algorithm which incorporates one or more basis sets according to the invention.

FIG. 3 is a block schematic diagram of an instrument that implements an algorithm which incorporates one or more basis sets according to the invention. FIG. 3 provides a detailed overview of the software/firmware component 30 of the device discussed in connection with FIG. 2. It should be appreciated that the invention herein is readily applied to any spectroscopic system. Thus, the system described in connection with FIGS. 2 and 3 is provided only as an example of a presently preferred embodiment of the invention and not by way of limitation.

During processing within the instrument, the digitized spectral information is first applied to the basis sets 31. As discussed above (and in greater detail below), the basis sets are reduced to transforms that remove interfering constituents and/or components (chemical and/or physical) from the spectral information. The basis sets may be applied before or in connection with a physical model 32 that corrects for such interfering physical factors as scattering, pathlength, and/or temperature.

After the spectral information is applied to the basis sets and (optionally) the physical model, the signal thus produced is deconvolved 33 to correct the signal to a reference. The signal is next preprocessed 34 and digitally filtered 35. Preprocessing may employ such techniques as Kubelka-Munk transformation, mean centering, normalization, baseline correction, scatter correction, and interference correction, although it is presently preferred that the basis sets be used to resolve such issues as scatter correction, baseline correction, and interference correction. Correction techniques that may be applied, for example to scattering, can include multiplicative scatter correction, standard normal variate correction, and extended multiplicative signal correction. The digital filtering function may be accomplished by such technique as Gaussian filtering, low and high bandpass filters, and Lorentzian filtering.

Spectral wavelengths for the analyte are selected 36 and a multivariate analysis, such as higher order partial least squares (PLS) is performed 37. Such analysis techniques may include principal component regression, partial least squares, rotated principal components, or correlation principal components analysis.

The preferred embodiment of the invention provides a plurality of basis sets that are used to quantify an analyte in a liquid sample. For purpose of illustration and example, the invention is now described in connection with glucose quantification in noninvasive spectra.

Data Collection. The first step of the process involves identifying major interfering chemical analytes and structures in the body. These factors include, inter alia, water percentage present in the sample, temperature/hydrogen bonding effects on water, albumin protein, globulin protein, triglycerides, cholesterol, urea, glucose, lactate, ethanol, also $Na^+$, $K^+$, $Cl^-$, and other electrolytes, glycosylated hemoglobin, skin, keratin, fibrinogen, and red blood cells.

One advantage of the invention is the basis set may be generated in such way that it includes spectra for all interfering components.

Noninterfering components include, for example, components of lower molar absorptivity concentration, such as low dosage drugs and medications.

In the presently preferred embodiment of the invention, data collection instrumentation should take into account the following:

Signal is defined for each analyte by first determining the delta absorption from top of absorbance band to base, and then by defining the slope of change in absorbance versus concentration for samples spanning the physiological concentration at all frequencies.

Noise is defined as root mean square (rms) noise of analyte absorbance in the band of interest.

Signal to Noise is defined as (slope X concentration)/ noise. This value must be greater than one for a minimum specified concentration to be analyzed.

Resolution in the presently preferred embodiment of the invention requires a minimum of seven points per peak.

Another factor to be considered is wavelength reproducibility. In the invention, a modified NIRS 5000 spectrometer is used to achieve the above criteria.

The data collection parameters for the basis set include the following:

Pathlengths due to absorbance of water, which is the primary interferant. It is necessary to select different pathlengths for each spectral window for an optimal basis set.

In the presently preferred embodiment of the invention, these pathlengths are:

0 to 2 mm for combination band region;

5 to 10 mm for first overtone region; and 10 mm or greater for second overtone region.

While not necessary, it is possible to generate a basis set over the entire frequency range in a single data collection to compare information in different regions. In the preferred embodiment of the invention, this dictates a 1 mm pathlength. Optimal signal to noise levels are obtained separately. It is also necessary to provide continuous spectra to identify and model parameters, such as change in refractive index as a function of frequency.

For applications that involve the use of diffuse reflection, pathlength considerations are not taken into account because light penetration is proportional to the inverse of water absorbance, as defined by the system, based upon molecules interacting with specific concentrations at specific refractive indices.

In some embodiments of the invention it is desirable to use optical filters. Because water behaves as natural short pass filter, it is advantageous to use long pass cutoff filters in conjunction with water bands to form a bandpass filter (although a system that provides sufficient resolution, i.e. a sufficient number of analog-to-digital (A/D) bit, may not require a filter). In the presently preferred embodiment of the invention, any filter in the midst of the $H_2O$ absorbance band may be used, e.g. the following filters may be used:

1950 nm long pass filter for the combination band;

1450 nm long pass filter for the first overtone; and 1100 nm long pass filter for the second overtone.

The number of averaged scans for each spectra must be determined, where noise decreases with an increasing number of scans. In the presently preferred embodiment of the invention, noise vs. number of averaged scans is set to 64 averaged scans.

Replicate spectra. Experiments were conducted in which four replicates were collected due to the temperature coefficient of the spectrometer. The following results were obtained (which were due to the spectrometer used to make the measurements—these results are not indicative of a general phenomenon):

First replicate—outlier due to temperature;

Second replicate—small outlier characteristics; and

Fourth replicate—acceptable for further analysis.

For purpose of experiments conducted in connection with the invention, the following additional parameters were defined:

Ionic strength is 0.1 M to match that of the body;

pH 7.35 phosphate buffer to approximate that of the body;

Temperature maintained at 38.0±0.2° C. to match that of the body;

Components: ACS reagent grade chemicals used as standards.

Data Analysis. Data analysis must take into account temperature variations. In the presently preferred embodiment of the invention, temperature variations of 0.1° C. are observed to severely obscure the analyte absorbance bands (even concentrated albumin). Laboratory and instrument temperatures are impossible to control to 0.01° C. for daily use. This effect is amplified in regions of high water absorbance and large changes of water absorbance due to temperature.

Data analysis must take into account pathlength. This consideration is similar to differential measurements taken in dual beam spectrometers, where one beam is focused through the sample and a second beam is focused through a pathlength corresponding to the pathlength interference in the sample.

It is desirable to control pathlength to 0.0001 mm. For a 1 mm cell with buffer present there is a 1 mm pathlength of water. When an analyte is present, the pathlength of water is reduced due to displacement. The displacement is linearly proportional to the concentration of the analyte present. While various components of the sample may be rotated out if their concentration is unknown, such processing is unnecessary upon using the invention because such concentrations are known.

Temperature and pathlength correction algorithm. The following discussion provides an exemplary temperature and pathlength correction algorithm in accordance with the invention.

1. Response function: residual (sample—buffer) about zero for regions where the analyte does not absorb.
2. Residual as function of spectral range is inversely weighted by the spectral noise of the sample.
3. Thousands of buffers collected at roughly 38° C. are compared with the sample to match temperature. By using thousands of buffers, a good temperature match can be found.
4. For each buffer tested, incremental pathlengths of water are tested to match pathlength of buffer in the sample. For example, to get a pathlength of 0.99 mm, the buffer being tested as a possible background is multiplied by 0.9900. For example, albumin protein from 0.95 mm to 1 mm at 0.0005 mm steps is tested with each buffer.

The following is a Matlab temperature/pathlength correction program for selected parameters that must be optimized for each analyte, such as pathlength, and regions for the response function:

```
temppath.M
% PROBLEM: Basis Set
% spectra require background substraction of temperature and pathlength.
% This program corrects the temperature by searching for a buffer
% collected at the same temperature as the sample and match the amount
% of buffer present in the sample.
clear
% enter wavelength region
wavelength = 1100:2:2498;
% load sample spectra
load albl2__1.txt
sample = albi2__1;
[o p] = size (sample);
% load buffer spectra
% usually use all buffers collected to date
load albbuff.txt
buff = albbuff;
[m n] = size (buff);
% Code minimizes residual over user set regions
% These regions can not have absorbance for the analyte
% they are fine tuned iteratively.
% in this case - three regions are used in the response function.
b__1st__pt = find(wavelength>= 1640 & wavelength < 1655);
b__2nd__pt = find(wavelength>= 2077 & wavelength < 2085);
b__3rd__pt = find(wavelength>= 1640 & wavelength < 1655);
s__1st__pt = b__1st__pt;
s__2nd__pt = b__2nd__pt;
s__3rd__pt = b__3rd__pt;
% initialize to large residual
pathlength = 0;
for aaa = 1 : p
            best__min(aaa) = 1000000;
end
% pathlength optimization
% determine pathlength matching water in sample
% (water absorbance * pathlength)
for j = 0.95 : 0.0005 : 0.997 %.98 j=manual__pathlength
            pathlength = pathlength + 1;
% temperature optimization
% for each pathlength, test every buffer for temperature match
        for temp = 1:n
            avg_b__1st__pt = mean(buff(b__1st__pt,temp))*j;
            avg_b__2nd__pt = mean(buff(b__2nd__pt,temp))*j;
            avg_b__3rd__pt = mean(buff(b__3rd__pt,temp))*j,
% repeat for every sample and replicate
            for sample__num = 1 : p
            avg_s__1st__pt = mean(sample(s__1st__pt,sample__num));
            avg_s__2nd__pt = mean(sample(s__2nd__pt,sample__num));
            avg_s__3rd__pt = mean(sample(s__3rd__pt,sample__num));
            diff__1st__pt = abs(avg_s__1st__pt - avg_b__1st__pt);
            diff__2nd__pt = abs(avg_s__2nd__pt - avg_b__2nd__pt);
            diff__3rd__pt = abs(avg_s__3rd__pt - avg_b__3rd__pt);
% store results of each loop
            results(sample__num) = diff__1st__pt + diff__2nd__pt + diff__3rd__pt;
% usually add in weighting function as inverse of noise for each region
% here if response function for given sample is best - record parameters
            if results(sample__num) < best__min(sample__num)
                best__min(sample__num) =
results(sample__num);
                best__pathlength(sample__num) = j;
                best temp(sample num) = temp;
            end % end if
        end % end sample
    end % end temperature
end % end pathlength
% dump best parameters to screen for interpretation
best__min
best__pathlength
best__temp
% plot temperature and pathlength corrected spectra
hold off
clg
hold on
v = [1500 2500 -0.01 0.07];
axis(v);
for sample__num = 1:p
    best__sample__corr(:,sample__num) = sample(:,sample__num) - buff(
:,best__temp(sample__num)) * best__pathlength(sample__num);
```

-continued

```
    plot (wavelength,best__sample__corr(:,sample__num));
    intensity(sample__num) = best__sample__corr(481,sample__num);
end
```

The resulting spectra are clean and baseline resolved. The spectra are selected to cover physiological concentrations for each analyte.

The following example illustrates the generation of a first basis set "Basis Set I."

EXAMPLE

Basis Set I near-IR absorbance features over the 1500 to 2500 nm spectral region are provided for water, albumin protein, globulin protein, triacetin, cholesterol, urea, and glucose with a 1 mm pathlength. In addition, sample temperature effects are included along with instrument noise levels.

Experimental:

Spectra of the major constituents of serum were collected over their respective physiological ranges. Sample preparation consisted of dissolving dried, reagent grade solid samples in a 0.1 M phosphate buffer adjusted to pH 7.35. All spectra were collected on a NIRS 5000 in transmission mode, with a 1 mm path length infrasil quartz cell, with a 120 second equilibration period, at 38.0° C., with 64 averaged scans, done in quadruplicate. A single instrument was used for all data acquisition.

Results and Discussion:

Spectra are analyzed in order of decreasing absorbance changes in the two spectral windows from 2050 to 2350 nm and 1550 to 1850 nm. The first replicate is discarded in all cases due to a consistent variation in temperature caused by the instability of the NIRS 5000 spectrometer and photons heating the sample (data not included). The sample is in equilibrium by the second sample replicate.

Figure 4:
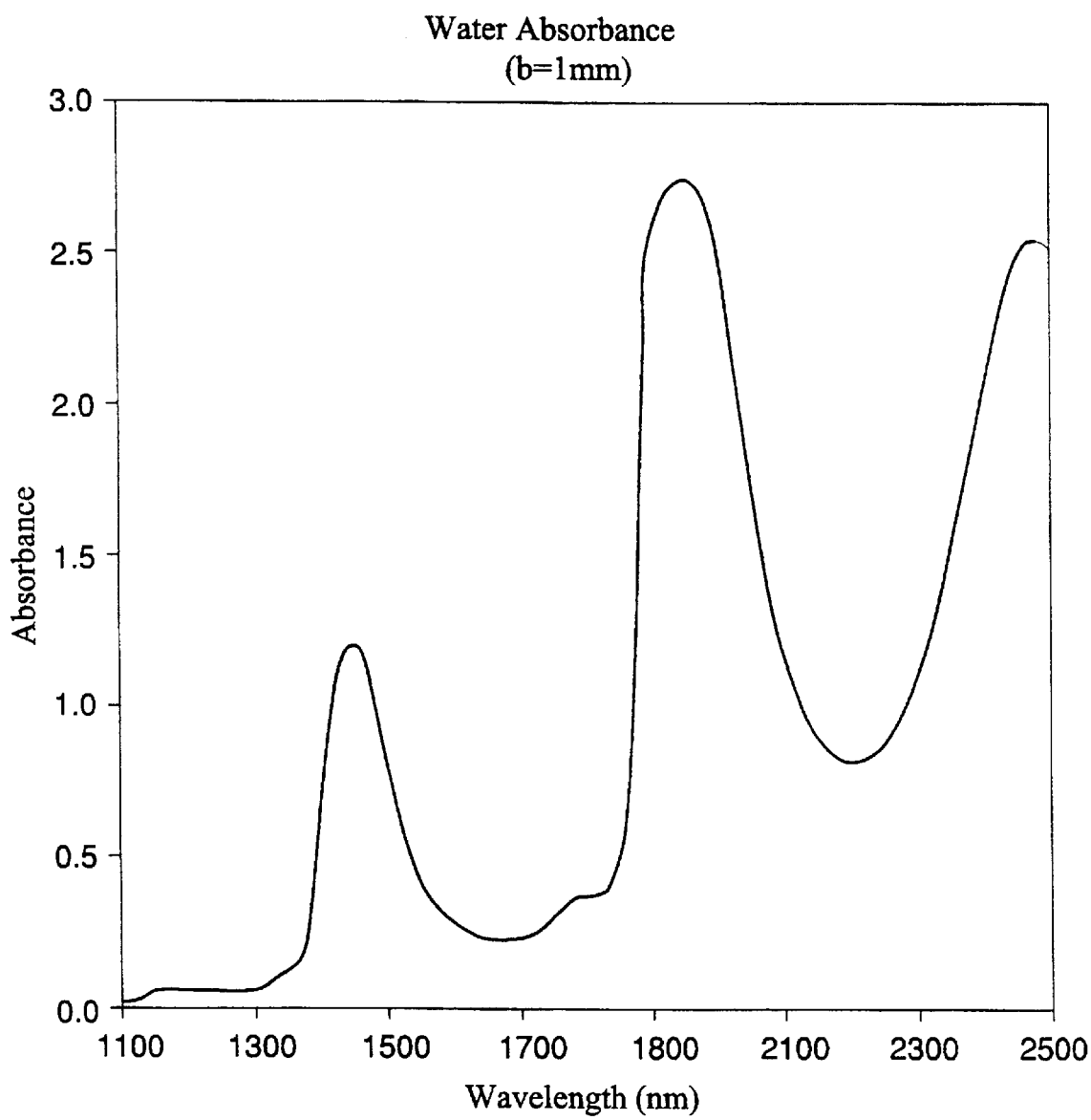
FIG. 4 is a plot of water absorbance vs. wavelength.

Water Spectra:

The near-IR is dominated by three large water absorbance bands centered at 2500, 1950, and 1450 nm as presented in FIG. 4. The high absorbance limits analysis done in aqueous solution in the near-IR to three spectral regions. The region from 2350 to 2050 nm is referred to herein as the combination band region; the region from 1850 to 1550 nm is referred to herein as the first overtone spectral region; and the region from 1400 to 1100 nm is referred to as the second overtone spectral region.

The NIRS spectrometer sets the gain and hence the dynamic range of the detector based upon the spectral region with the most light intensity reaching the detector. This is the second overtone spectral region for aqueous samples. However, the combination band region has the largest absorbance, followed by the first overtone region, and then the second overtone region. Due to the low absorbance of water in the 1300 nm region versus the 2200 nm region, a relatively small dynamic range is left for the 2200 nm region where glucose bands are the largest. Therefore, a 1500 nm long pass filter was employed which forces the NIRS system to set the gain based upon the first overtone spectral region. Hence, in the initial basis set no spectral information is provided for the second overtone region, optimum signal to noise levels are provided for the first overtone spectral region, and slightly degraded signal to noise levels are obtained for the combination bands. Among many modifications made to the NIRS system is an order sorter which allows a different gain setting for each of the three spectral regions during a single scan for the next basis data set.

Figures 5A, 5B:
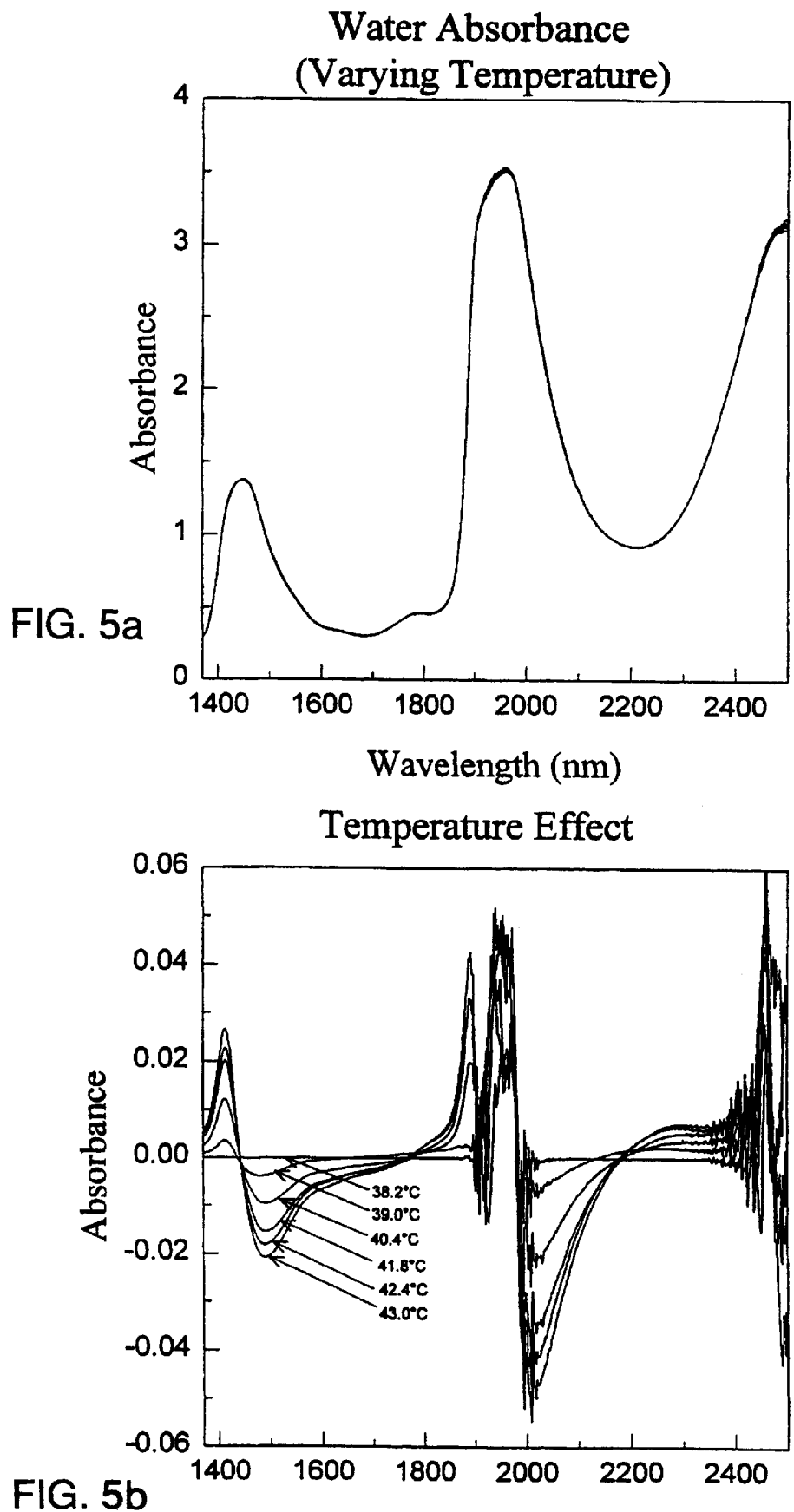
FIG. 5a is a plot of water absorbance for a varying temperature vs. wavelength.
FIG. 5b is a plot showing temperature effect.

Temperature Effects on Water Spectra:

All three water absorbance bands in the near-IR shift to higher frequency with increasing temperature. Buffer spectra collected from 38.2 to 43.0° C. are presented in FIG. 5A. The instrument should be modified to collect lower temperature spectra. A slight broadening of the lines can be observed on each of the water absorbance band shoulders. Subtracting a spectrum of water collected at 38.2° C. from spectra of water collected at higher temperatures reveals the magnitude and direction of the shift. Negative absorbance bands that increase with temperature are observed at 2000 and 1480 nm. As the water bands shift to higher temperature, there is less water absorbance in these regions, so that subtracting out a water absorbance band from a lower temperature results in too much background being subtracted. Positive absorbance bands that correlate with increasing temperature are observed at 2300, 1890, and 1400 nm. With increasing temperature, the water absorbance increasingly moves into these spectral regions. Subtracting out the 38.2° C. water spectrum does not subtract out enough in these regions. The large water absorbance, coupled with the temperature shift, greatly hinders near-IR analysis. FIG. 5B reveals that in the subtraction, no useful information is obtained where the raw absorbance is greater than 3.0±0.1, indicating the limit of the dynamic range of the NIRS system. Therefore, the regions above 2460 nm and from 2010 to 1890 nm result in no analytically useful information and may be discarded for data collected with a 1 mm pathlength. Information in these spectral regions may be obtained by adjusting the pathlength. Due to the water absorption, the width of the regions that need to be discarded increases as the pathlength analyzed increases. In addition, the temperature effects are seen to span the entire combination band region and first overtone spectral region. As will be shown, these changes in baseline are roughly equal in magnitude to the highly absorbing protein and much greater in magnitude than all other spectral analytes examined.

Figure 6A:
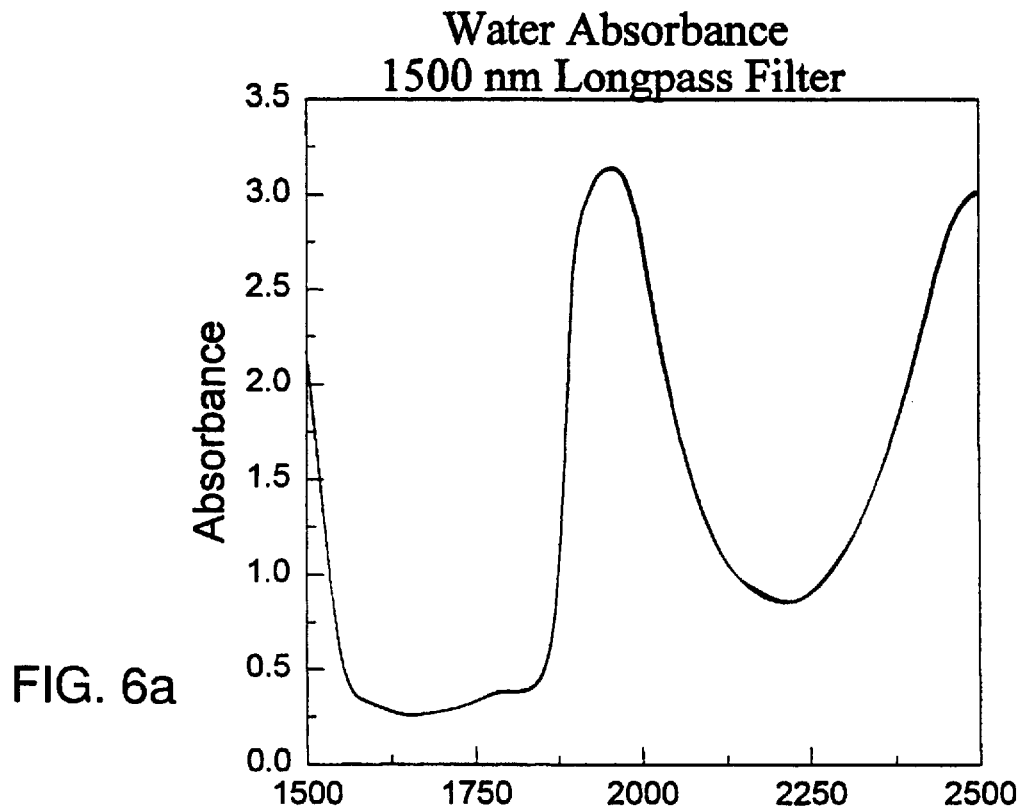
FIG. 6a is a plot of water absorbance vs. wavelength showing absorbance when a 1500 nm long pass filter is used.
Figure 6B:
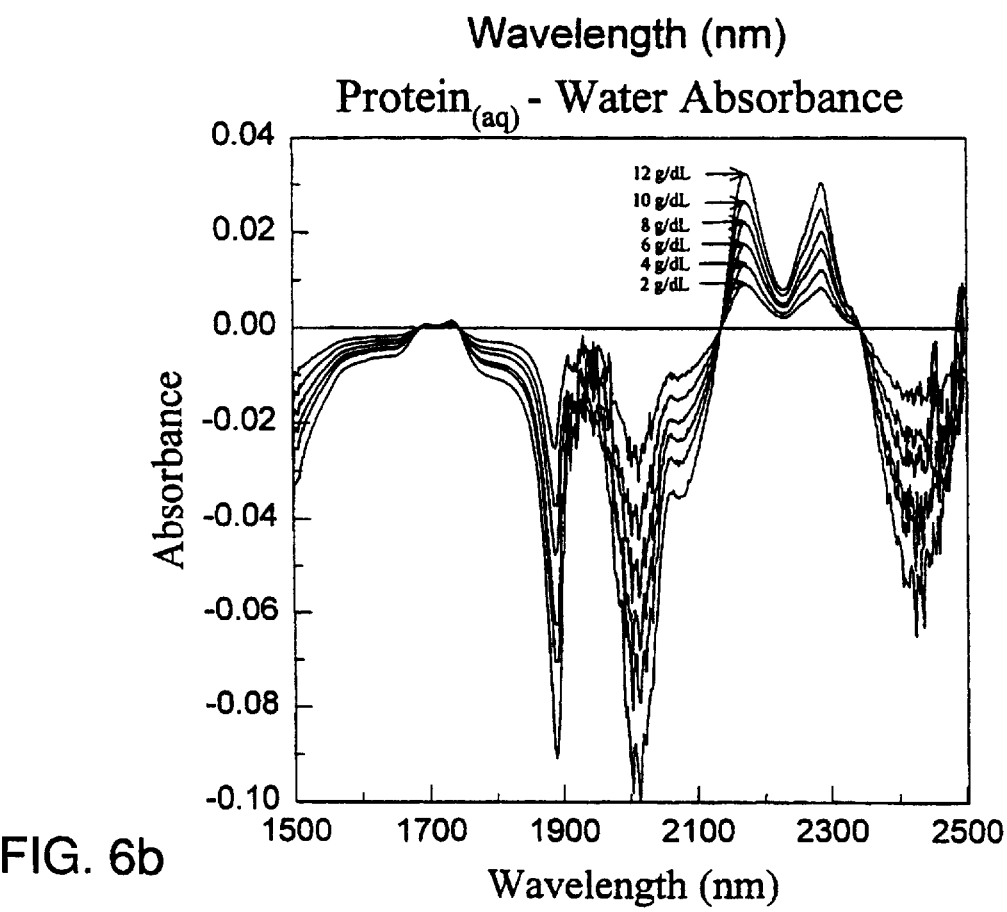
FIG. 6b is a plot of absorbance vs. wavelength showing $protein_{(aq)}$—water absorbance.

Albumin Protein:

After water and temperature effects, serum spectra are primarily composed of absorption from albumin protein which has a physiological range of 2.6 to 7.9 g/dL. Albumin protein absorbance bands are difficult to see in the presence of water, as shown in FIG. 6A. Subtracting out a buffer spectrum results in protein absorbance peaks at 2285, 2170, 1730, and 1690 nm, as shown in FIG. 6B. Large negative absorption bands also appear in the resulting spectra where water absorbs. These bands are not primarily due to variation in temperature as a derivative of the water band would appear as seen in FIG. 5B. The negative bands are due to displacement of water by albumin and scattering.

A program, such as the MATLAB program described above, is used to determine the best buffer in terms of temperature and best calculated pathlength to be used as a background spectrum for subtraction. In FIG. 6B, the buffer and albumin in buffer spectra both had the same 1 mm fixed pathlength. Because albumin is present in the 1 to 12 g/dL range in this example and water is 100 g/dL, the albumin occupies a significant volume of the cell and less water is present per unit volume. A program was written that multiplies the water spectrum by a percentage that can be sequentially varied over a wide range. The optimum calculated pathlength for each albumin in buffer spectrum was determined by minimizing the sum of the absolute value of the residuals in locations where albumin does not absorb and temperature effects are at a minimum (2085 to 2077 and 1655 to 1640 nm). The residual in the overtone region was weighted twice as much to compensate for the higher noise in the combination band region. To further minimize temperature effects, all buffer spectra collected were run through this optimization to find the best buffer in terms of temperature matching with the sample. Each albumin in buffer spectrum was run through this algorithm independently.

The results of subtracting the best buffer at the adjusted pathlength for each albumin spectrum are presented in FIG. 7. Additional albumin absorbance bands are now visible at 2060 nm and 2335 nm. Expansion of the graph about the 2060 nm absorbance bands reveals increasing absorbance for each increase in albumin concentration. The albumin band centered at 2170 nm is more symmetrical than the one seen in FIG. 6B. The two peaks in the first overtone spectral region have a better baseline correction and now increase in absorption linearly with increasing concentration. However, negative absorbance bands are still evident where water absorbs at 2020 and 1870 nm. The region between 2000 and 1900 nm is an artifact of the mathematical correction over a region where the absorbance is greater than 3 and the system does not respond. In addition, there is a large difference between 0 absorbance and the 1 g/dL albumin spectrum. This difference should be equal to the difference in absorbance from 1 to 2 g/dL. This offset can be reduced if the combination band region and the overtone region are treated individually. It should be pointed out that no baseline correction, smoothing, or scatter correction has been employed at this point.

Figure 8:
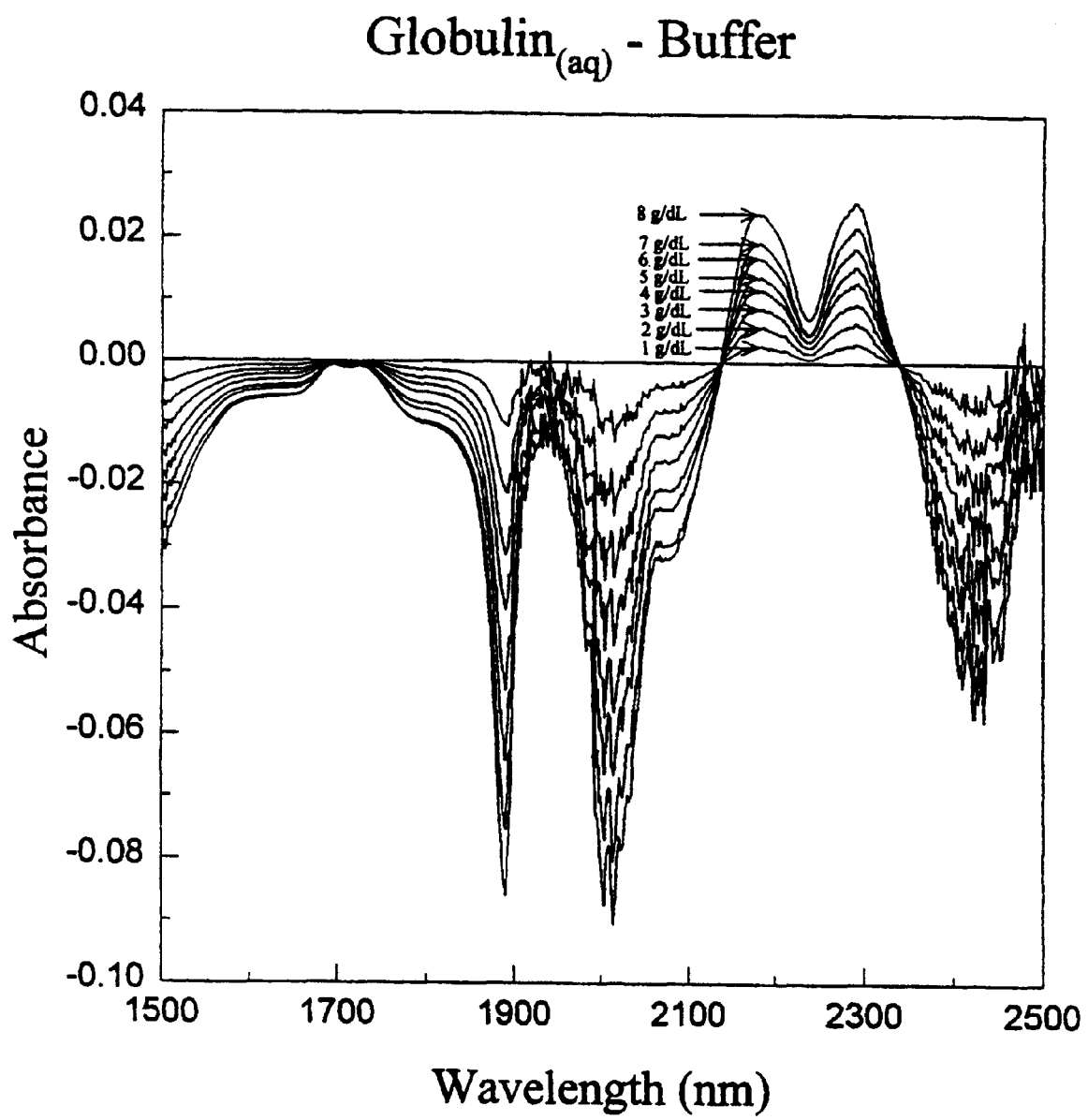
FIG. 8 is a plot of absorbance vs. wavelength showing $globulin_{(aq)}$—buffer.
Figure 9:
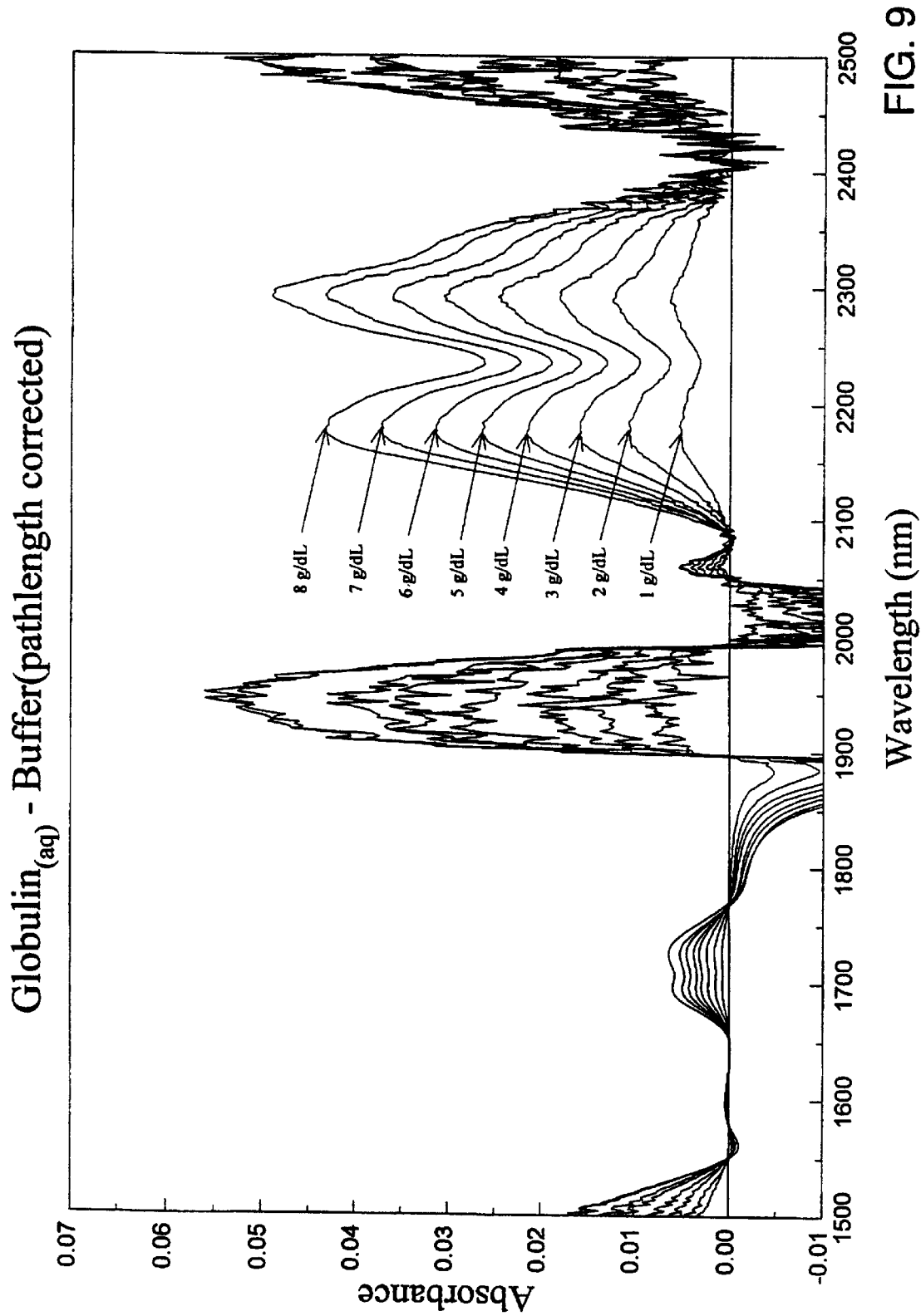
FIG. 9 is a plot of absorbance vs. wavelength showing $albumin_{(aq)}$—buffer (pathlength corrected)

Globulin Protein:

Physiological concentrations of globulin (0.7 to 8.1 g/dL) are less absorbing in the near-IR than albumin. Straight subtraction of the phosphate buffer allows the same peaks to be observed that are seen in albumin protein, as shown in FIG. 8. The temperature and pathlength correction algorithm discussed above was run with exactly the same parameters as for albumin and the same additional extra peaks were found, as shown on FIG. 9. Overlaying the albumin and globulin spectra reveals that the globulin absorbance band centered at 2170 nm is slightly broader than that of albumin protein.

Figure 10:
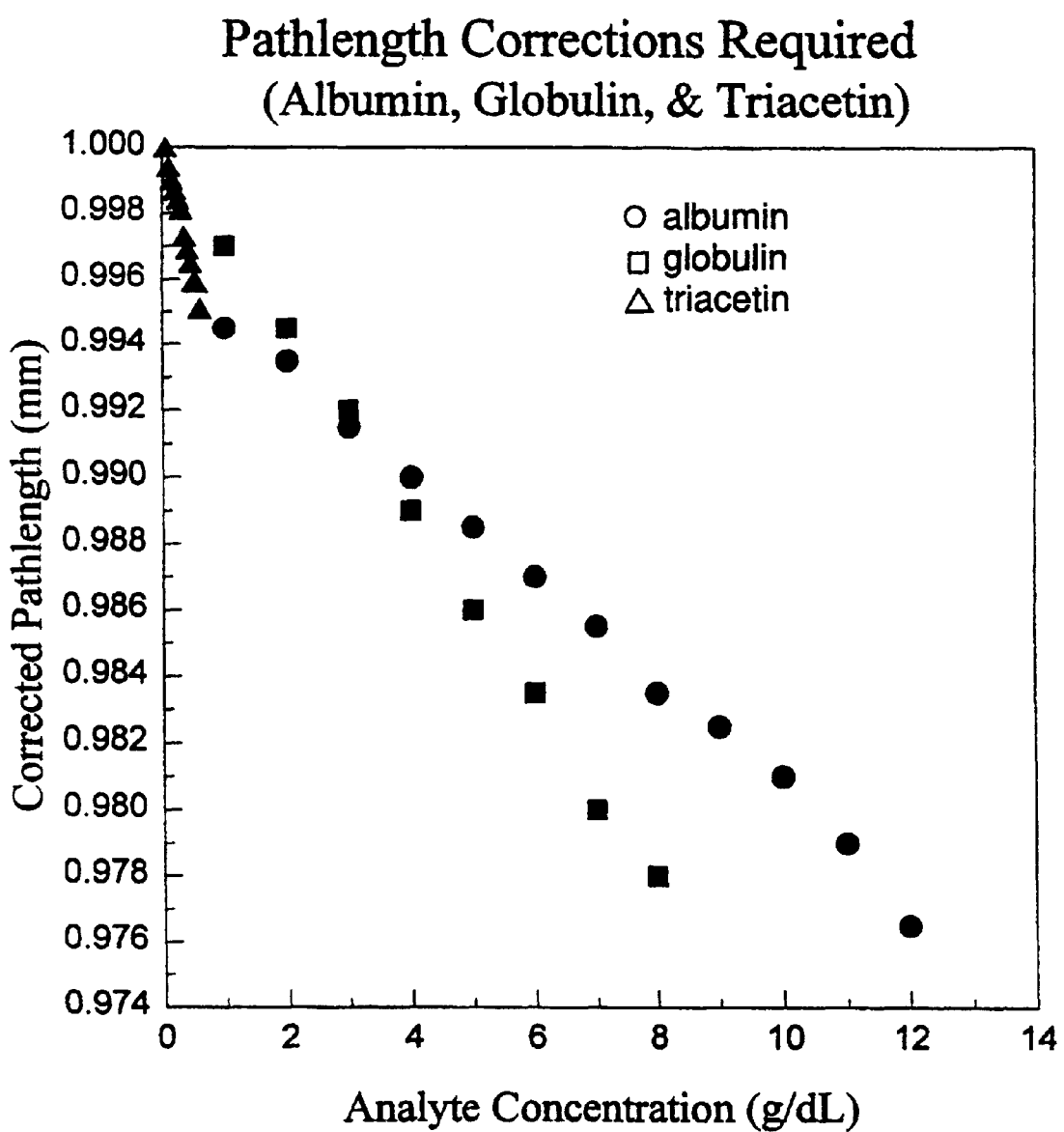
FIG. 10 is a plot showing pathlength corrections required for albumin, globulin, and triactetin.

The calculated pathlengths required for the background subtraction from each of the spectra are presented in FIG. 10. For albumin, the correction is linear with increasing concentration, but has a y-axis intercept of 0.996 mm. This is consistent with the poor baseline observed in FIG. 7. The corrections for globulin are also linear, but greater corrections are required per mg/dL analyte. This is consistent with the scattering tendencies of globulin. The y-axis intercept is 1.00, consistent with the excellent background subtraction.

Figure 11:
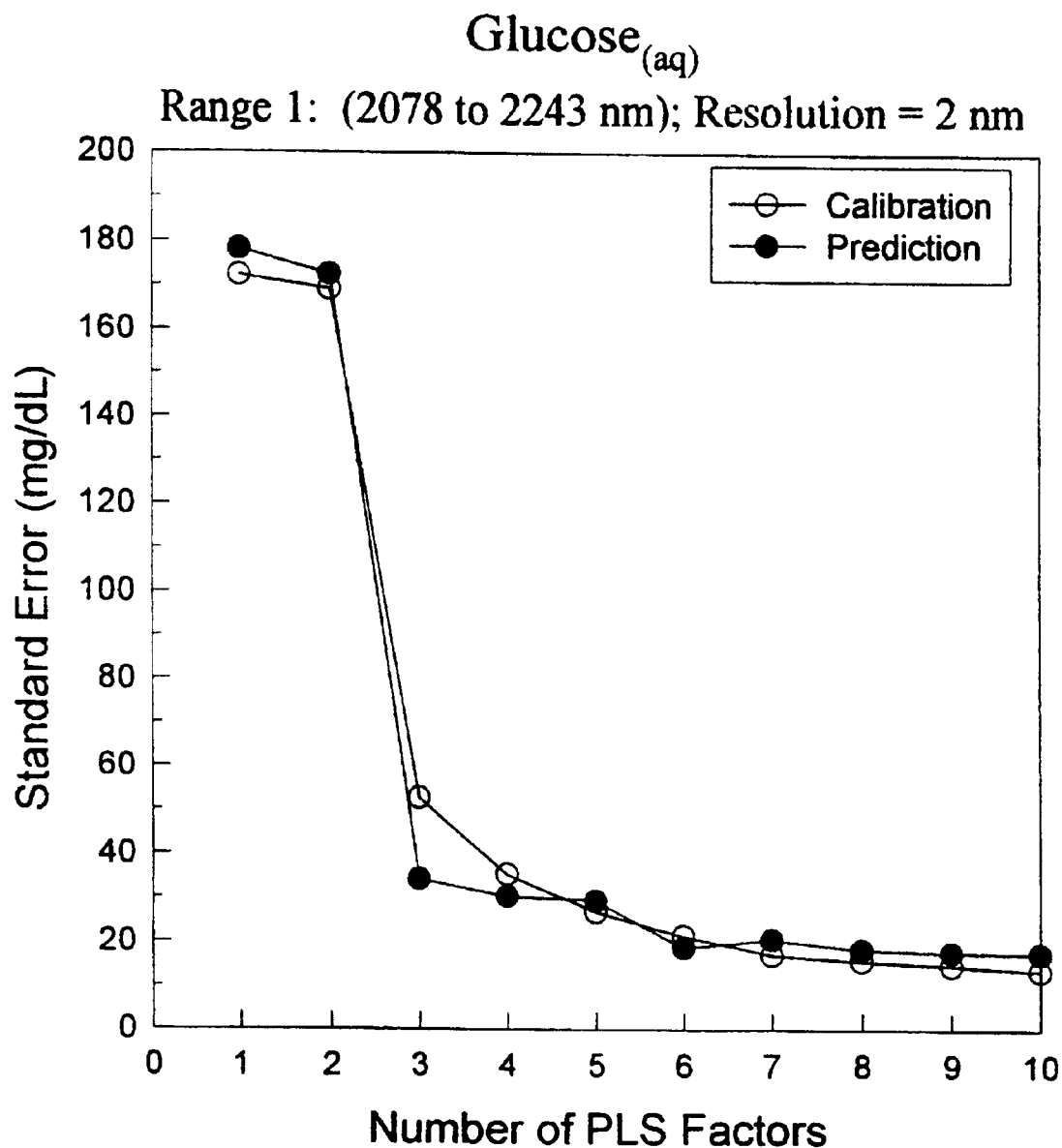
FIG. 11 is a plot of absorbance vs. wavelength showing $triacetin_{(aq)}$—buffer (pathlength corrected)

Triglycerides:

Triacetin is used to simulate triglycerides. The physiological range of triacetin is 50 to 450 mg/dL. The temperature and pathlength correction algorithm is again employed, but different regions are used in determining the minimum residual (2420 to 2440, 2080 to 2090, and 1575 to 1635, weighted 1:5:20). Six triacetin absorbance bands result centered at 2320, 2250, 2130, 1760, 1715, and 1675 nm, as shown on FIG. 11. The resulting pathlengths required for correction are linear with concentration, but much smaller deviations from 1 mm result due to the lower concentration of triacetin versus protein in serum, as shown on FIG. 10. The signal levels of the smaller triacetin absorbance bands approach the noise level of the spectrometer.

Figure 12A:
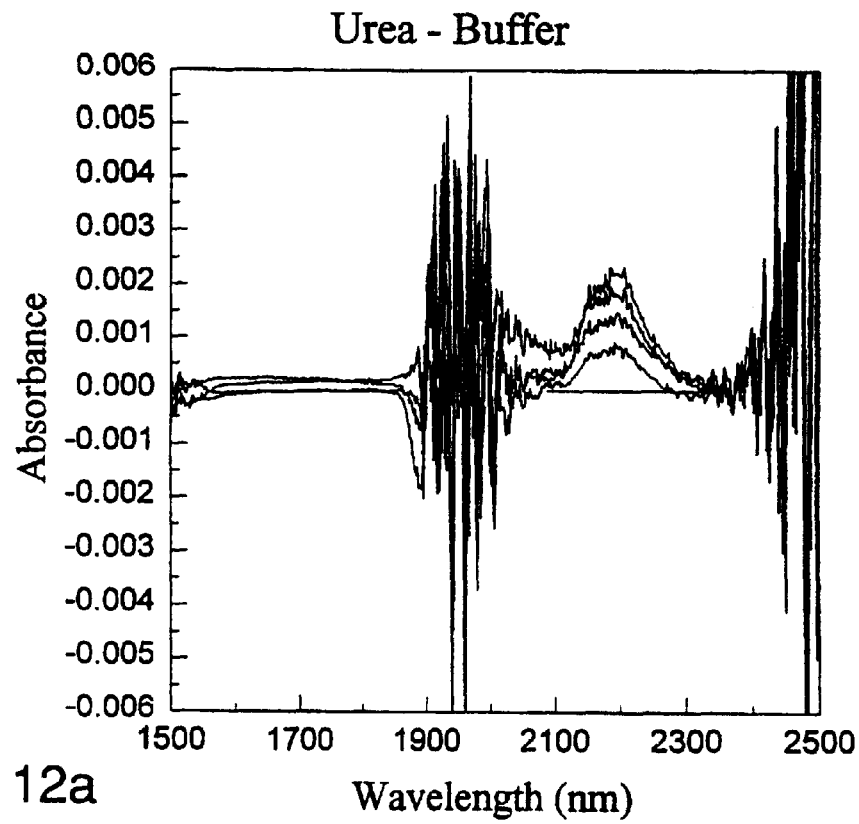
FIG. 12a is a plot of absorbance vs. wavelength showing urea—buffer.
Figure 12B:
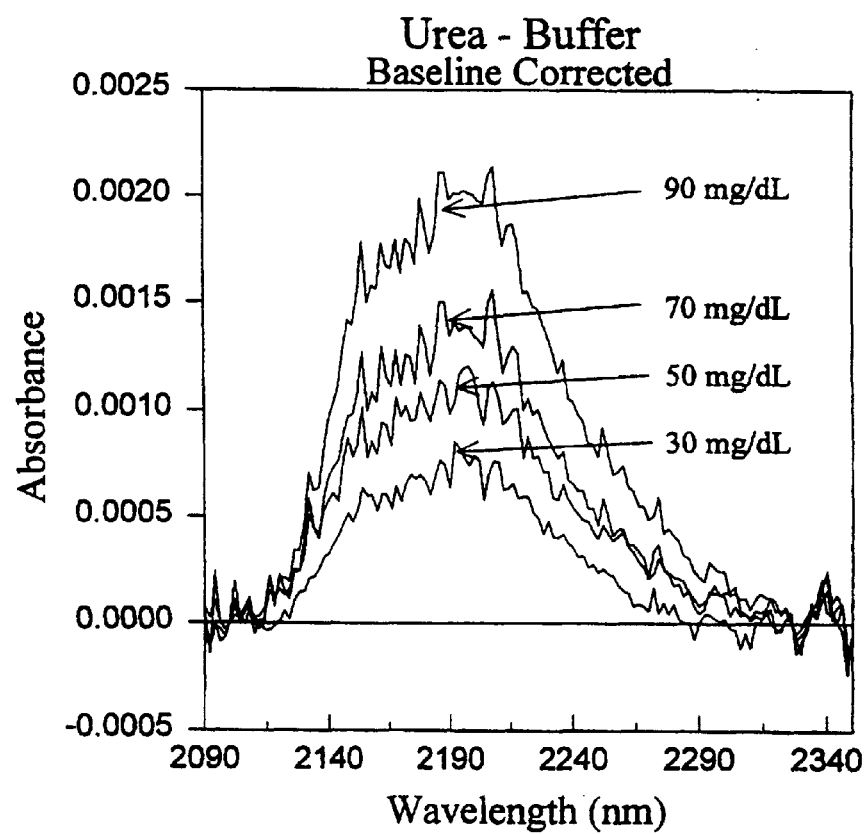
FIG. 12b is a plot of absorbance vs. wavelength showing urea—buffer (baseline corrected)

Urea:

Twelve urea in buffer spectra were collected. Due to the small physiological concentration of urea (6 to 123 mg/dL), the algorithm used to optimize the background by changing the effective pathlength of the buffer subtracted fails because no significant FIGS. of water are displaced. No temperature matching algorithm is employed, but buffer spectra collected with each sample are used. A straight background subtraction followed by a two point baseline correction (2094 to 2106 and 2320 to 2332 nm) was performed and is presented in FIG. 12. A single absorbance band is present centered at 2190 nm. No overtone peak is present. This is consistent with this absorption being related to N—H, whereas all of the other analyses have O—H fundamental vibrations. Only four spectra are presented due to large baseline drifts that obscure the linearity of the additional spectra. Higher concentration samples can be run to obtain a higher S/N and cleaner spectra, although the same resulting basis set is obtained.

Figure 13:
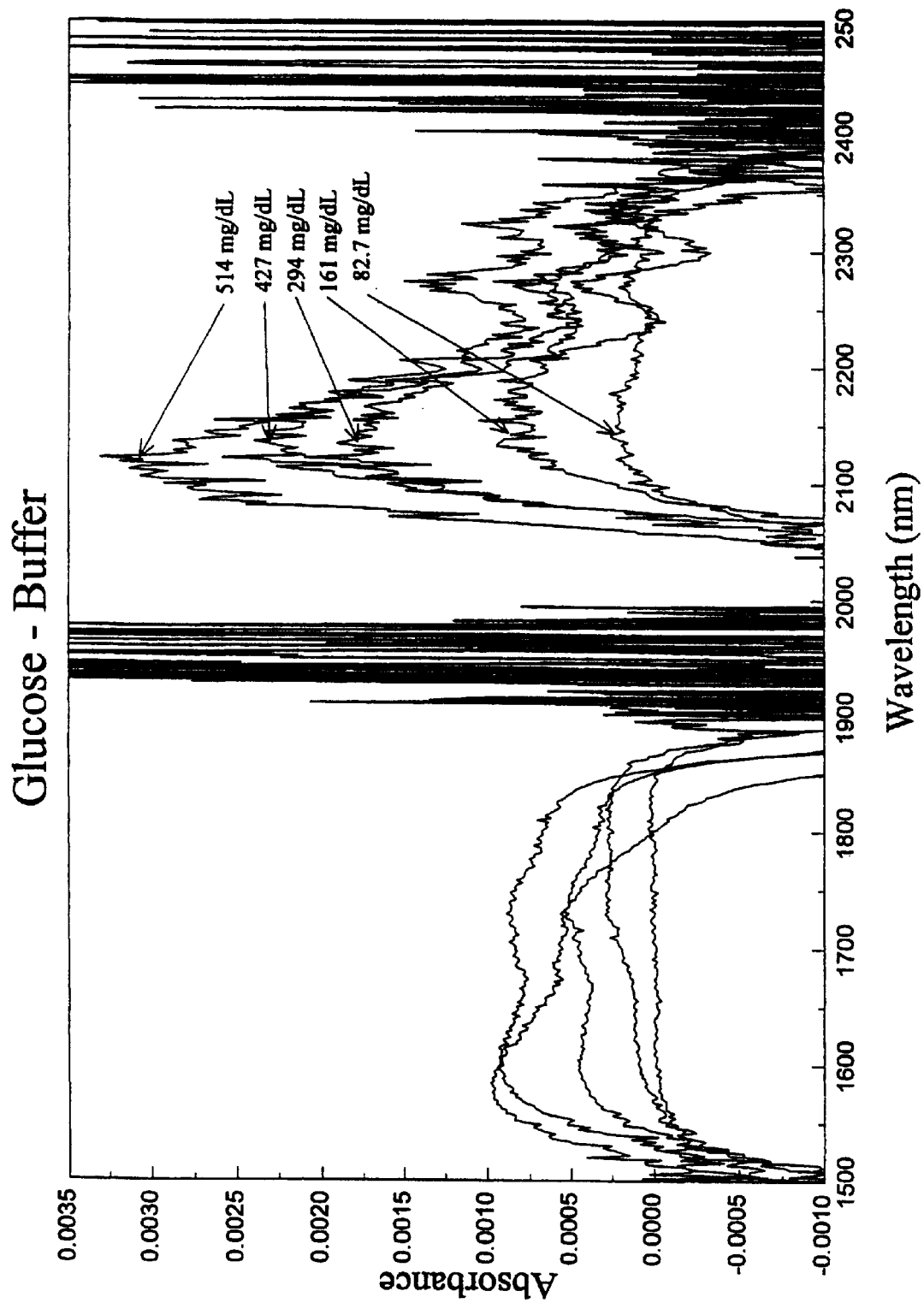
FIG. 13 is a plot of absorbance vs. wavelength showing glucose—buffer.

Glucose:

A complete glucose in buffer study was performed over the combination and first overtone spectral region of which a subset is presented here. Glucose was examined from 30 to 600 mg/dL (also from 0 to 5000 mg/dL) to cover the physiological as well as hypoglycemic and hyperglycemic levels of glucose. A straight subtraction of buffer from glucose in buffer shows absorbance bands centered at 2326, 2272, 1800, 2150, 1730, and 1590 nm, as shown in FIG. 13.

Conclusions:

Consistent with theory, for all analytes, the combination band spectral region yields larger absorbance than the first overtone spectral region. However, longer pathlengths quickly degrade the signal to noise level in the combination band region due to the large water absorbance, whereas the spectral quality in the first overtone spectral region should increase with small millimeter increases in pathlength. The absorbance bands in the region of glucose absorbance in decreasing order of absorbance are water, temperature effects, albumin protein, globulin protein, cholesterol, triglycerides, urea, and glucose. While every analyte analyzed absorbs more than glucose and over the same general spectral region, every analyte has a distinct absorbance signature. In principle, the serum spectra or the noninvasive spectra, can be deconvoluted.

The invention contemplates the generation of additional basis sets, such that substantially all interfering components are identified and factored into the spectroscopic analysis.

The following example illustrates the generation of a second basis set "Basis Set II."

EXAMPLE

Basis Set II

A study was rerun on dried, crushed, and pressed solid samples to give absorbance spectra with no water. A second basis set was collected based upon spectra of solid or neat components of human serum. The resulting absorbance spectra show the combination, first, and second overtone absorbance bands. In addition, for a given component the relative absorbance between regions may be compared. Combined, another method of wavelength selection is made available.

Experimental :

Pure component spectra of the liquid form of water (pH 7.35, 0.1 M phosphate buffer 38.0±0.2° C.), triacetin, and lactic acid were collected. Albumin, globulin, cholesterol, urea, and glucose exist as a solid in their pure state. For these analytes, each was individually ground with a mortal and pestle to a fine powder in the absence of potassium bromide. The powder was then compressed into a transparent pellet in a specially designed press that fits into the NIRS 5000 transmission module. Four replicates of each component were then obtained in the transmission mode. The pathlength of each analyte was not controlled.

Figure 14:
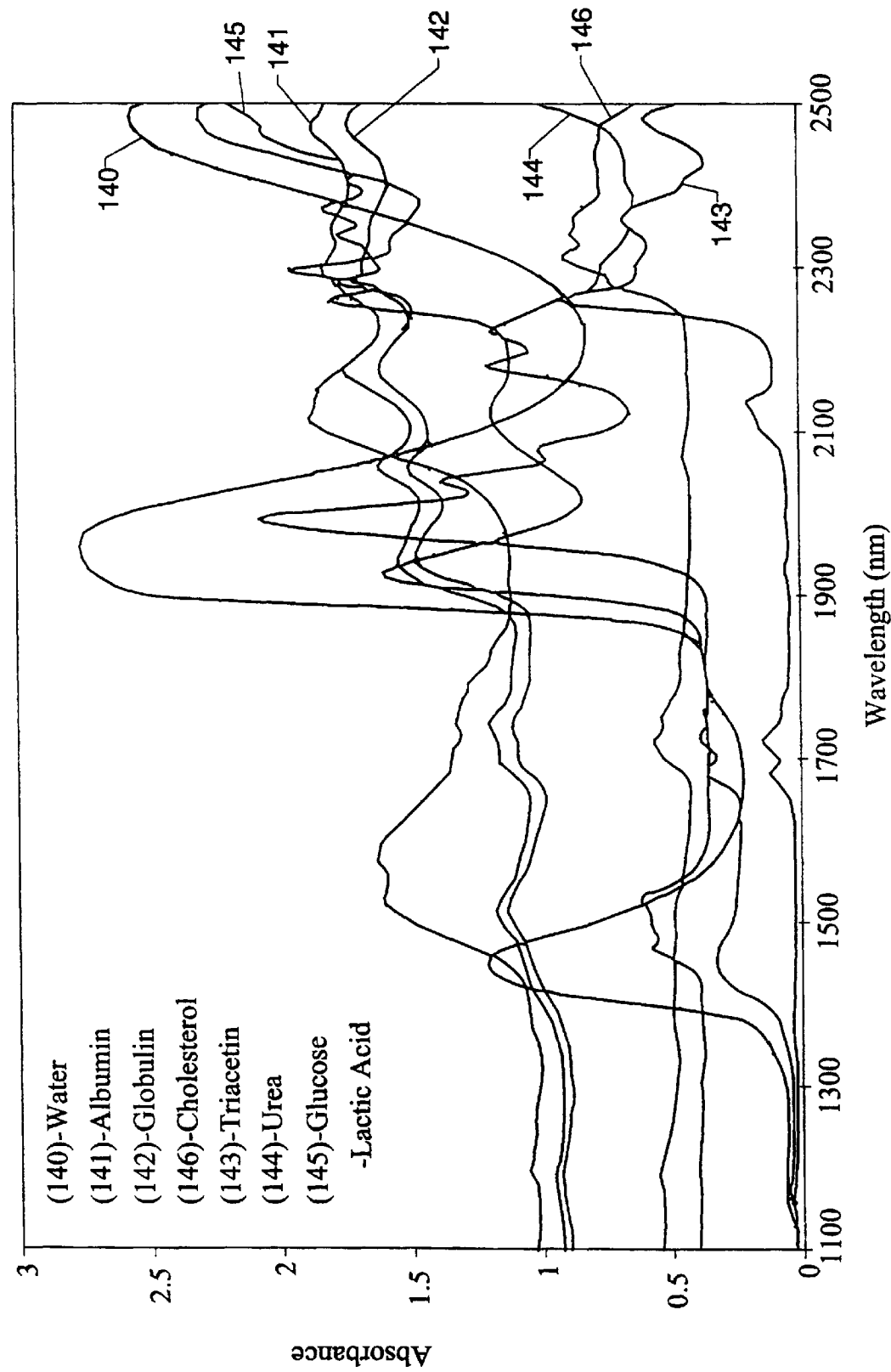
FIG. 14 is a plot of absorbance vs. wavelength for solid samples.

Results and Discussion :

The raw absorbance spectra for water, albumin, globulin, cholesterol, triacetin, urea, glucose, and lactic acid are presented in FIG. 14. Because the pathlength of each pellet was not controlled, the relative absorbance between components can not be compared. The relative absorbance between frequencies for a given analyte can be compared. The large baseline offsets are due to the thickness of the sample and resulting total light throughput. This plot is included to show the total absorbance of each analyte relative to the dynamic range of the NIRS 5000.

Figure 15:
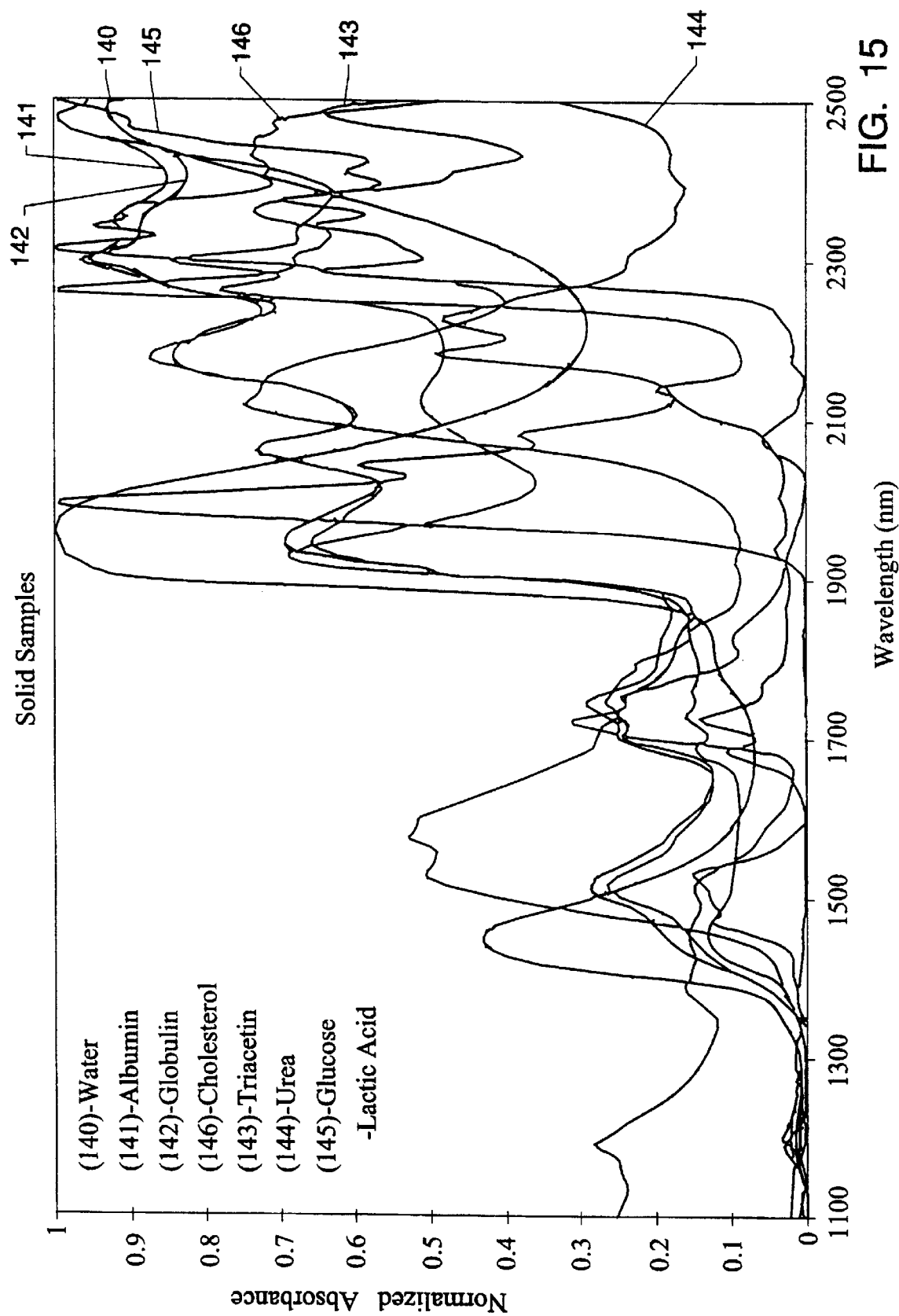
FIG. 15 is a plot of normalized absorbance vs. wavelength for solid samples.

For each component in FIG. 14, the minimum absorbance was subtracted out and the resulting spectra was normalized to 1 absorbance unit, as shown in FIG. 15. The resulting full scale plots make it easier to compare absorbance as a function of frequency and differences between components. For all three spectral regions, i.e. combination (2050 to 2350 nm), first (1550 to 1850 nm), and second overtone (1100 to 1400 nm), the absorbance bands are observed to be distinct. In principle, each component can be deconvoluted. It should be noted that when interacting with water, these absorbance bands may shift and broaden. Comparing with the aqueous absorbance from Basis Set I (above) reveals the absorbance bands of the neat or solid water (140), albumin (141), globulin (142), and triacetin (143) to be in the same location with the same widths. Both urea (144) and glucose (145) reveal additional resolution of peaks that have broadened and merged in the presence of water.

Several key spectral signatures emerge from this Example. First, the combination band region contains absorbance for each of the individual analytes. These absorbance are in every case more intense than those in the first and second overtone spectral regions. Cholesterol (146) absorbance drops off rapidly in this region as does triacetin. Neither interfere significantly with the glucose absorbance band centered at 2150 nm. The only interference is from water, albumin, and globulin which are shown in the Example—Linearity Study (below) to be removable by simple subtraction.

In the first overtone spectral region every component has an absorbance band except urea with its N-H bonds. Here the intensities of the absorbance bands range from 15% to 50% that of the corresponding combination band absorbance. It should be recognized that these values are for a fixed pathlength and can be adjusted based upon total pathlength.

Figure 16:
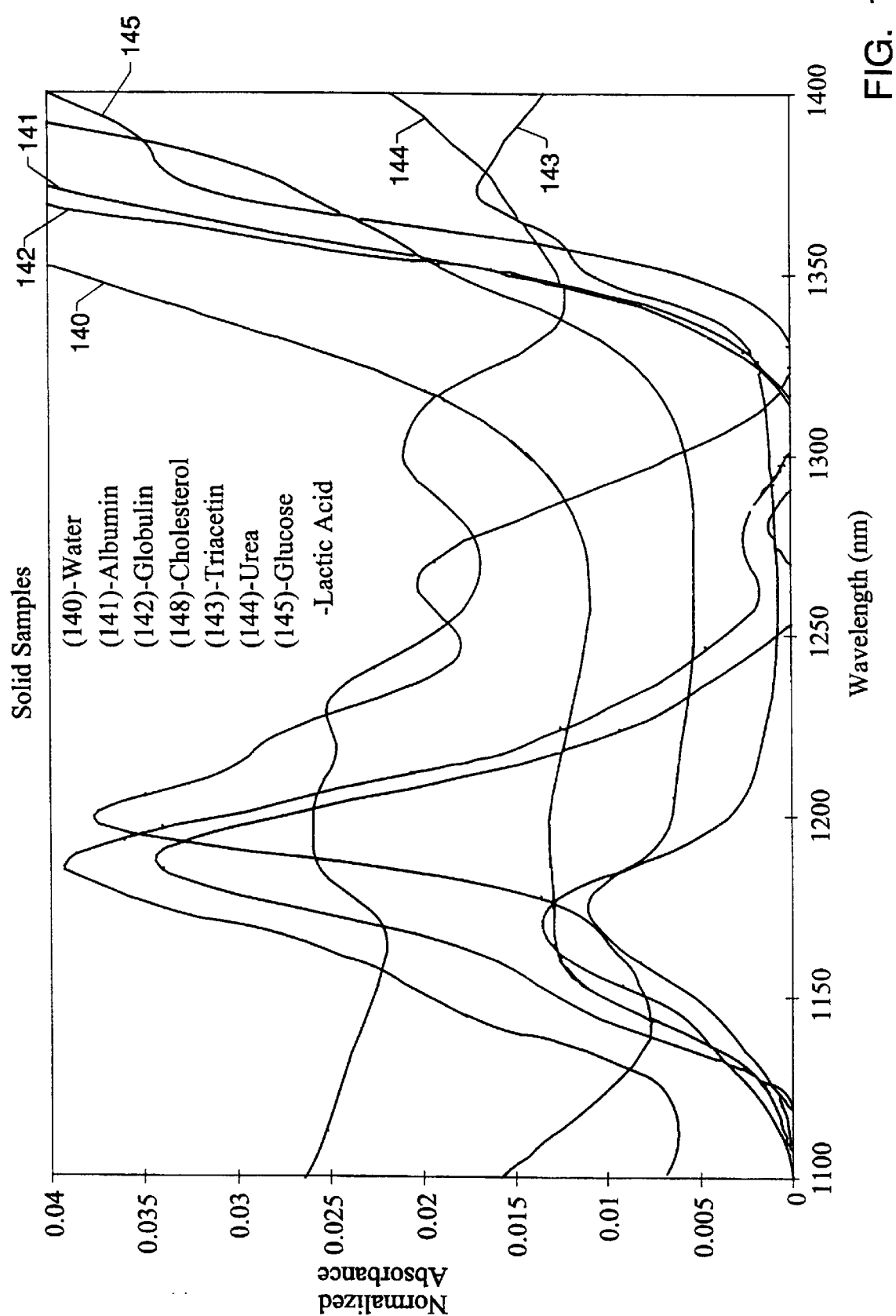
FIG. 16 is a second plot of normalized absorbance vs. wavelength for solid samples.

The second overtone spectral region has absorbance bands for every component examined, but the relative absorbance are the smallest, as shown on FIG. 16. The glucose band (145) seen here is very difficult to see in the presence of water (140).

Conclusions:

Each of the three regions contains information about every analyte with the exception of urea in the first overtone spectral region. The absorbance bands are highly overlapped and are generally less intense at higher frequencies. The absorbance bands are all distinct.

The following example illustrates the generation of a third basis set "Basis Set III."

EXAMPLE

Basis Set III

The first basis set was repeated with no edge filter present to allow comparison of all spectral ranges. The first Example above used a 1500 nm long pass filter to force the NIRS spectrometer to gain range on the 1700 nm spectral region. This Example could be repeated with increased optical pathlengths to yield higher signal to noise levels in the first and second overtone spectral regions.

The following example illustrates the generation of a fourth basis set "Basis Set IV."

EXAMPLE

Basis Set IV

It is necessary to measure interactions of molecules in solution. In this Example, a serum data set is collected.

Data Sets:

The first data set consists of spectra of glucose dissolved in a 0.1 M phosphate buffer adjusted to pH 7.35. Reagent grade glucose was weighed and diluted to a known volume with the 0.1 M phosphate buffer. Spectra were collected in the transmission mode with a 1 mm quartz cell using the NIRS 5000 spectrometer over the range of 1100 to 2500 nm with readings taken every 2 nm. A 1500 nm long pass filter was placed before the sample to force the NIRS spectrometer to set the gain on the peak signal at 1600 nm. Before and after every sample, 7 spectra of the 0.1 M phosphate buffer were collected. A total of 64 glucose$_{(aq)}$ samples were collected with 7 sequential replicates of each sample. The glucose samples covered a dynamic range of approximately 20 to 600 mg/dL. All samples were maintained at 38.0±0.2° C.

The second data set consists of serum samples prepared by Western States Plasma. Each serum sample was analyzed using a standard SMAC analysis yielding concentrations for calcium, ionized calcium (calculated), phosphorus, glucose, uric acid, urea nitrogen (BUN), creatinine, creatinine/BUN ratio, total protein, albumin, globulin, A/G ratio, total bilirubin, ALT, ALP, LD (LDH), AST, GGT, sodium, potassium, chloride, carbon dioxide, triglycerides, and cholesterol. To extend the dynamic range and level the concentration distribution, reagent grade urea and glucose were quantitatively added to the serum samples. The NIRS 5000 spectrometer was used in the fashion described above with the same wavelength region, pathlength, temperature control, and long pass filter. A 0.1 M phosphate buffer adjusted to pH 7.35 was run before and after each serum sample. A total of 196 serum samples were collected with 4 sequential replicates of each sample. The glucose analyte covered a dynamic range of approximately 20 to 600 mg/dL.

Experimental:

Glucose is determined in each data set using PLS regression analysis. The data sets are broken up into calibration and prediction keeping all replicate spectra together. A data point was originally collected every 2 nm from 1100 to 2500 nm. Additional data sets are formed from this data set by keeping every other point, every $3^{rd}$ point, every $4^{th}$ point, . . . , to every $32^{nd}$ point. PLS calibration models and predictions are then determined using 1 to 10 PLS factors.

Figure 17:
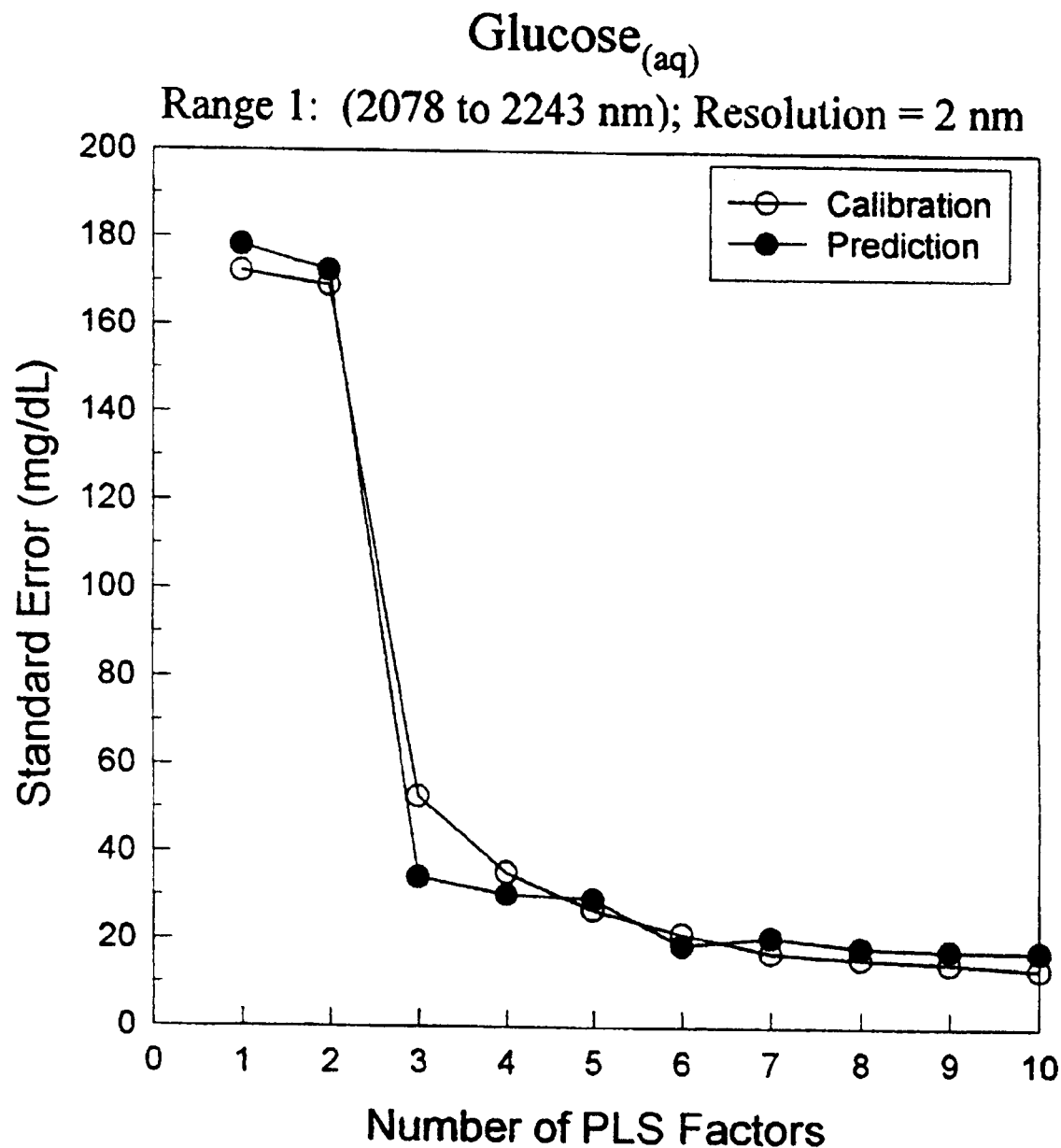
FIG. 17 is a plot of standard error (mg/dL) vs. number of PLS factors for $glucose_{(aq)}$.

Results and Discussion:

For each resolution, the resulting standard error of calibration (SEC) and standard error of prediction (SEP) is determined for 1 to 10 PLS factors, as shown on FIG. 17. Here, selection of the optimum number of factors needs to be achieved. As different ranges need to be compared, differences in the number of PLS factors employed can lead to erroneous conclusions. Statistical approaches to determining the optimum number of factors have failed. Because the SEP does not increase as the system is over-modeled, and further because the SEC and SEP yield similar results with 10 factors, it was decided for the purposes of this Example only to compare standard errors from range to range using the results obtained with ten PLS factors.

Ten spectral ranges are analyzed in both the glucose in water and glucose in serum data sets. These are summarized in Table 1 below. Ranges 1 to 3 and 5 to 7 correspond to the full width at zero height of the six glucose absorbance bands isolated in the near-IR. Ranges 4 and 8 splice together regions 1 to 3 and 5 to 7, respectively. Ranges 9 and 10 expand regions 4 and 8 into regions of increasing water absorbance, increasing noise, and no additional glucose information.

TABLE 1

Spectral Ranges Employed

| Range Number | Spectral Range (nm) |
|---|---|
| 1 | 2078 to 2243 |
| 2 | 2243 to 2272 |
| 3 | 2297 to 2366 |
| 4 | 2078 to 2366 |
| 5 | 1587 to 1674 |
| 6 | 1674 to 1709 |
| 7 | 1709 to 1754 |
| 8 | 1587 to 1754 |
| 9 | 2000 to 2500 |
| 10 | 1520 to 1805 |

Clearly, the wider spectral region that incorporates more glucose information (and water and temperature) results in a lower standard error at any resolution than any of the three individual glucose absorbance bands.

The nominal resolution of the NIRS spectrometer is 10 nm for the standard 0.040" exit slit used in this Example. Still, the standard error is observed to increase slightly as the resolution degrades from 2 to 10 nm. This is due to the manner in which the data sets were created from the original 2 nm resolution data set. For instance, in the 6 nm resolution data set generated, every third spectral point is kept. This means that two-thirds of the data are discarded. The discarded data has glucose, water, and temperature signal. In addition, by keeping these extra points, the effective noise is decreased by signal averaging. In as much as the true resolution of the NIRS 5000 is 10 nm, 100% of the slope observed on the SE vs. resolution graph is due to this systematic error. In addition, the same slope is observed from 10 to 32 nm resolution.

Figure 18A:
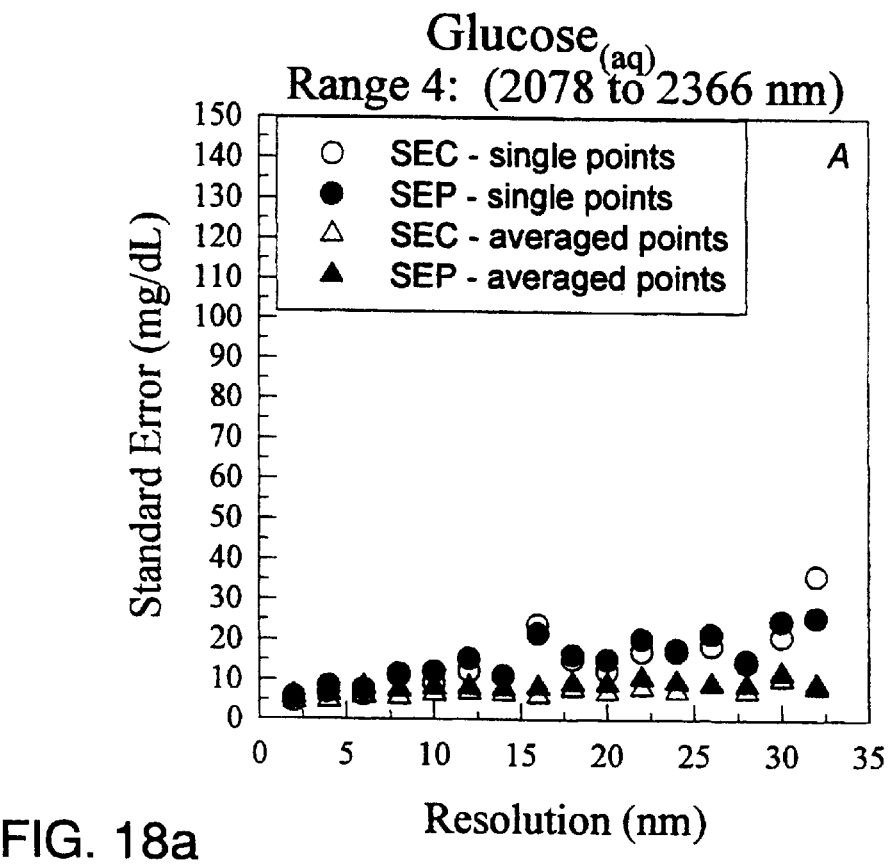
FIG. 18a is another view of the fourth plot of standard error (mg/dL) vs. resolution (nm) for $glucose_{(aq)}$.
Figure 18B:
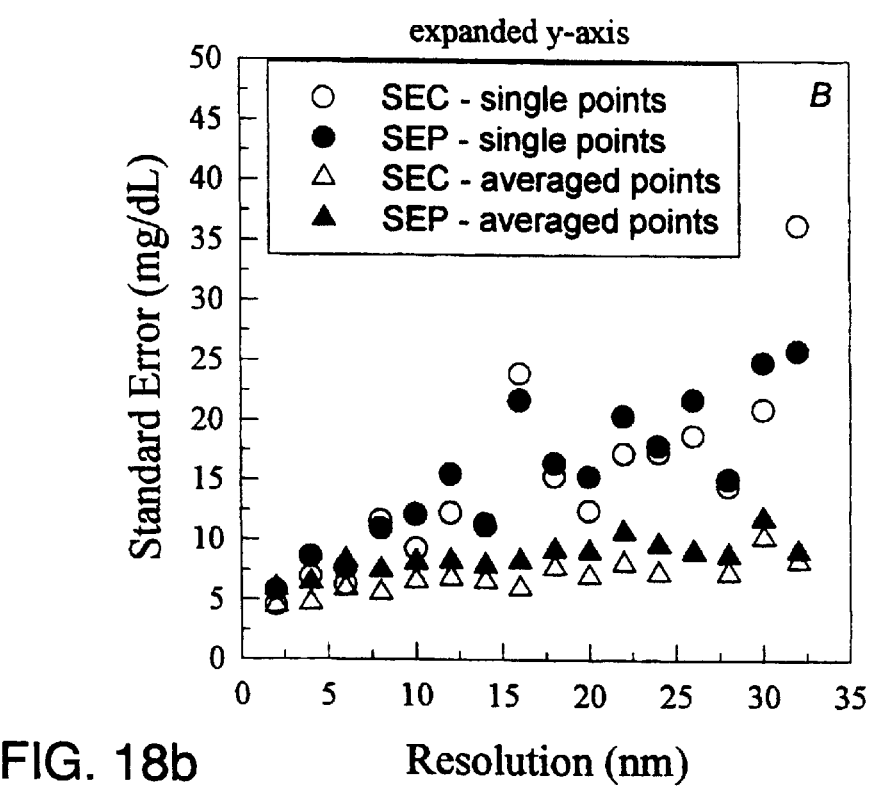
FIG. 18b is another view of the fourth plot of standard error (mg/dL) vs. resolution (nm) for $glucose_{(aq)}$ showing an expanded y-axis.
Figure 19:
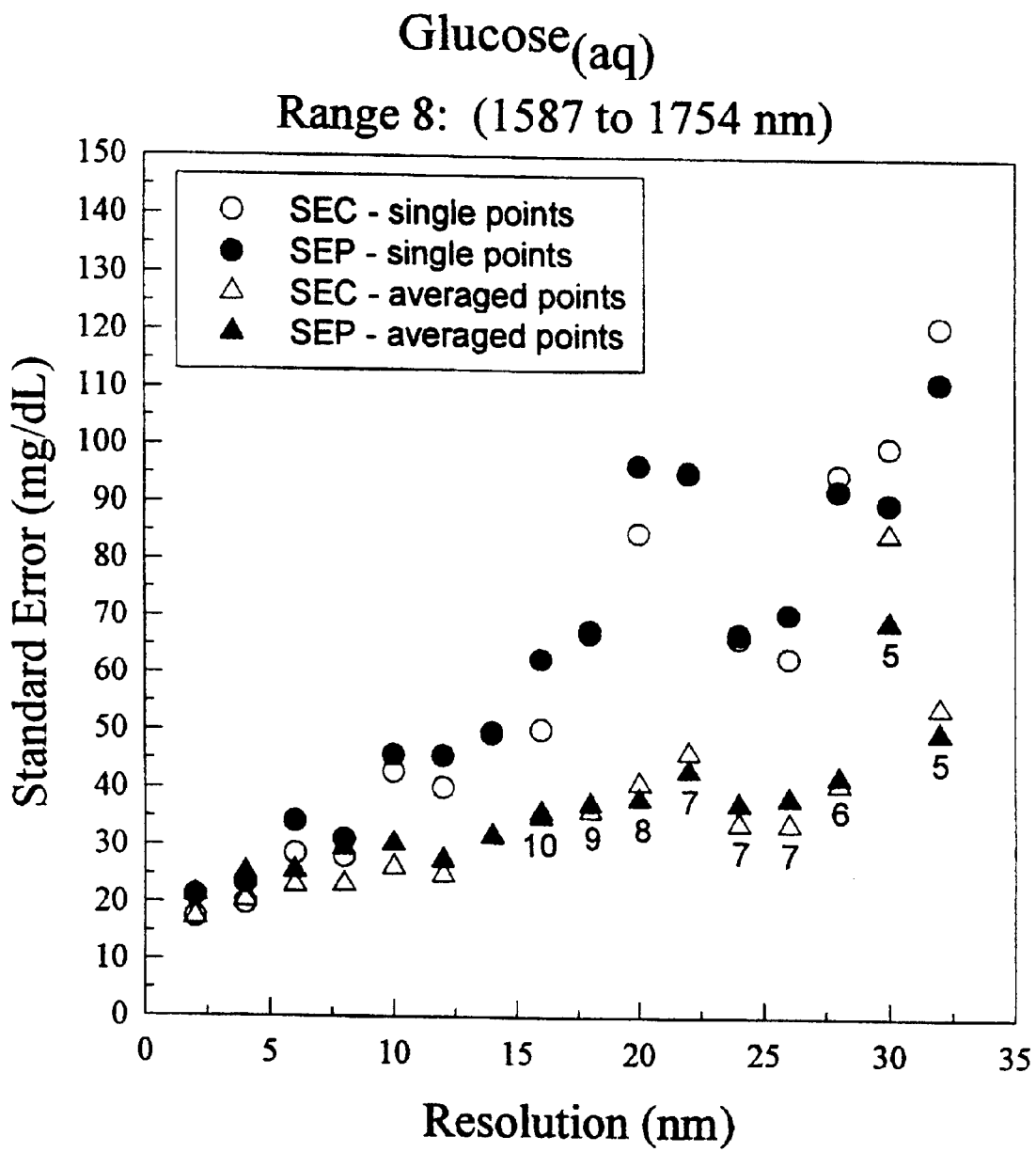
FIG. 19 is another view of the eighth plot of standard error (mg/dL) vs. resolution (nm) for $glucose_{(aq)}$.
Figure 20:
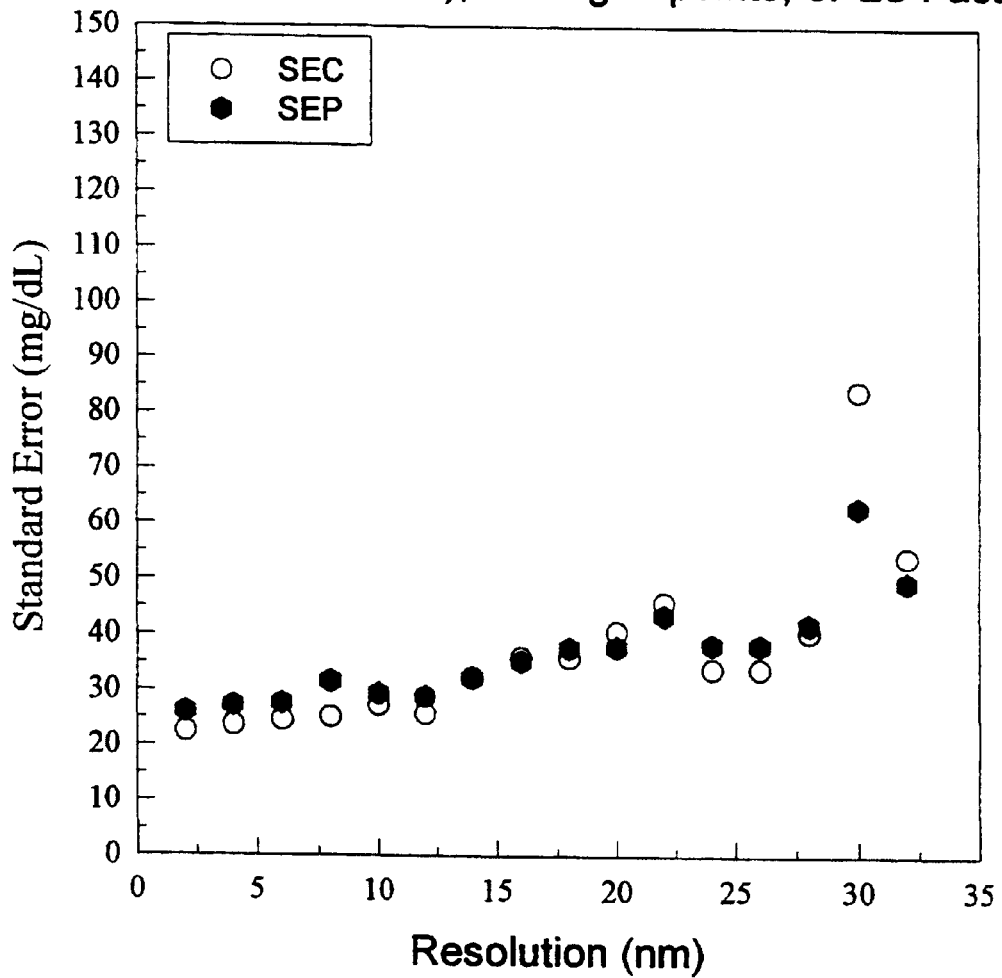
FIG. 20 is another view of the eighth plot of standard error (mg/dL) vs. resolution (nm) for $glucose_{(aq)}$ showing averaged points of six PLS factors.
Figure 21:
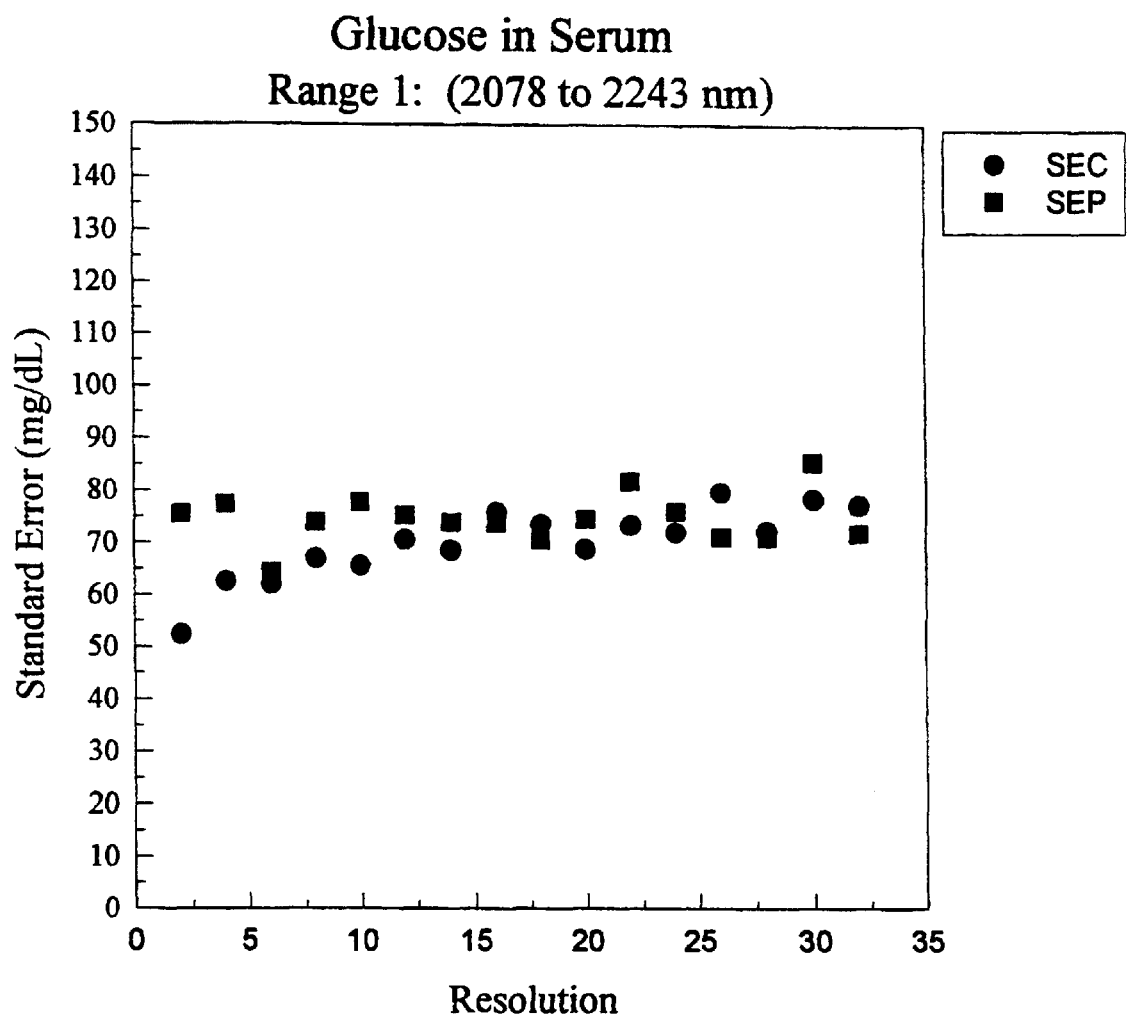
FIG. 21 is a plot of standard error (mg/dL) vs. resolution (nm) for glucose in serum.
Figure 22:
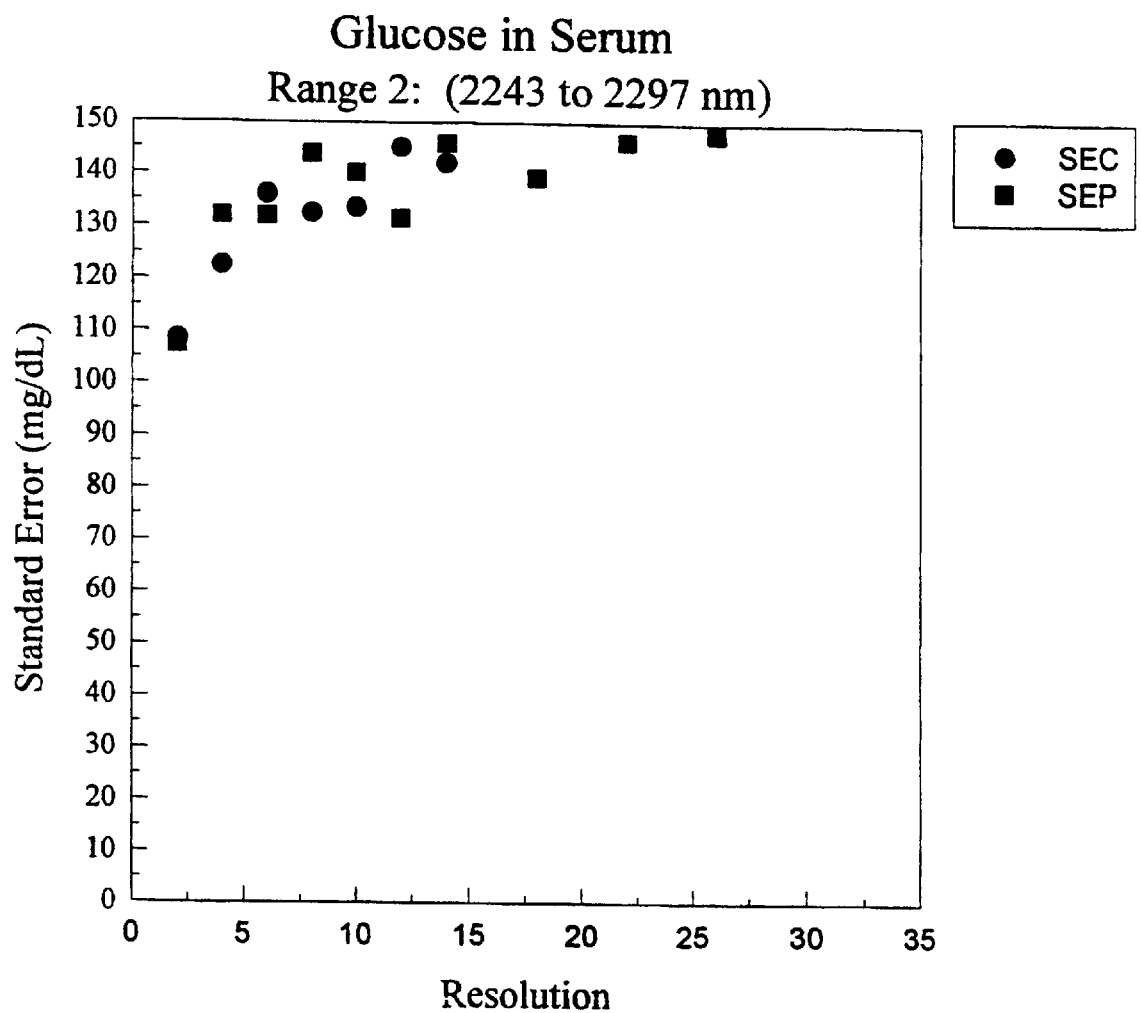
FIG. 22 is a second plot of standard error (mg/dL) vs. resolution (nm) for glucose in serum.
Figure 23:
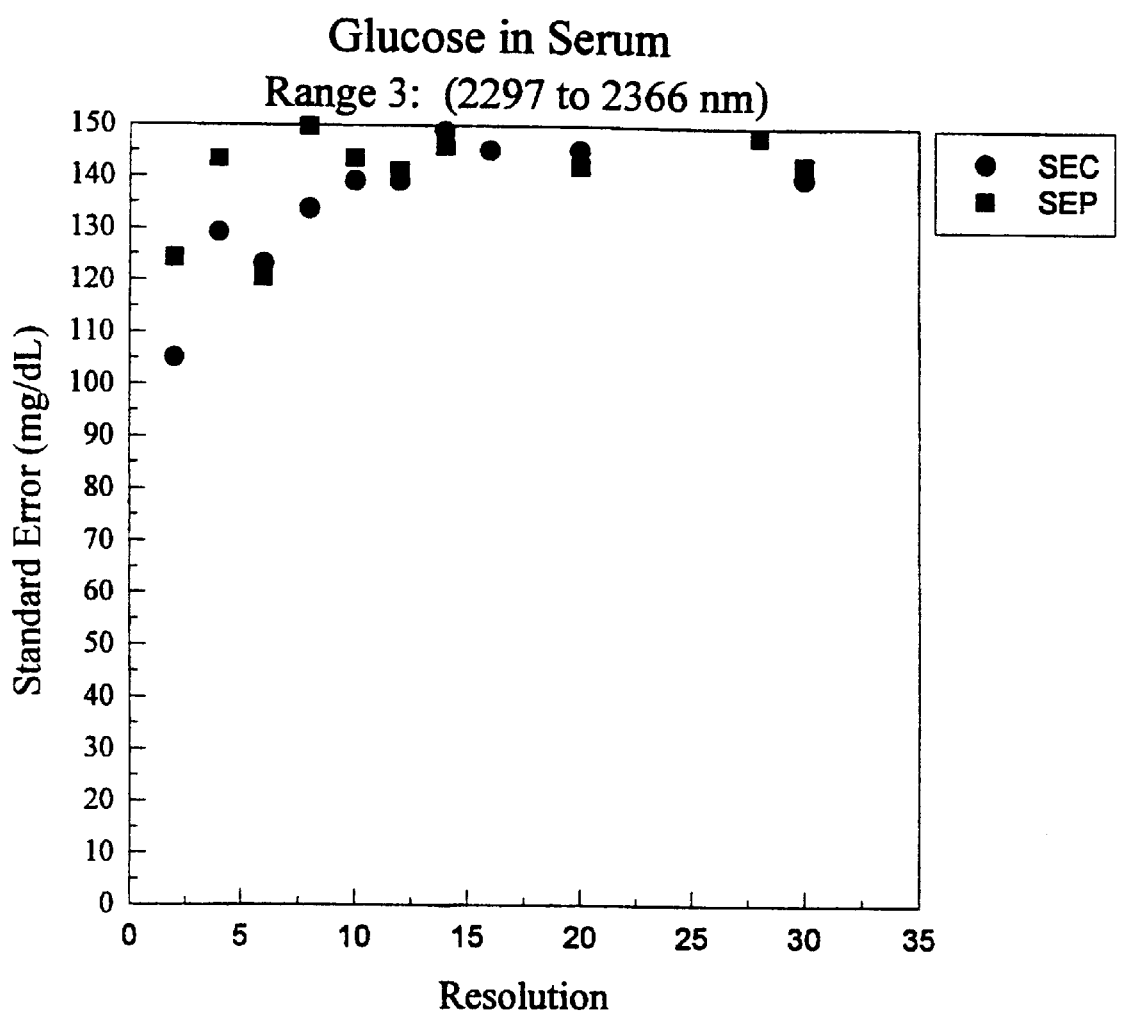
FIG. 23 is a third plot of standard error (mg/dL) vs. resolution (nm) for glucose in serum.
Figure 24:
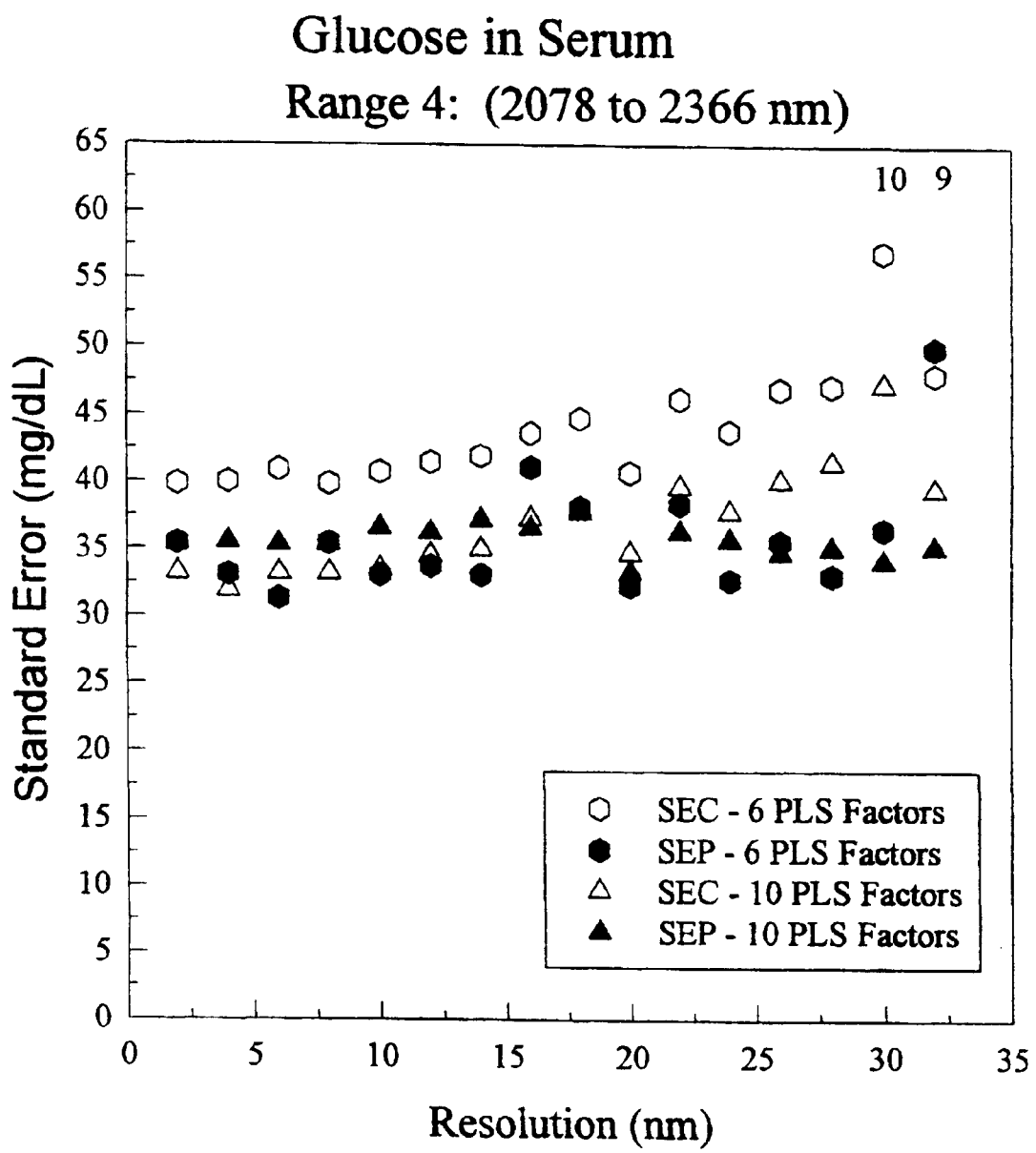
FIG. 24 is a fourth plot of standard error (mg/dL) vs. resolution (nm) for glucose in serum.
Figure 25:
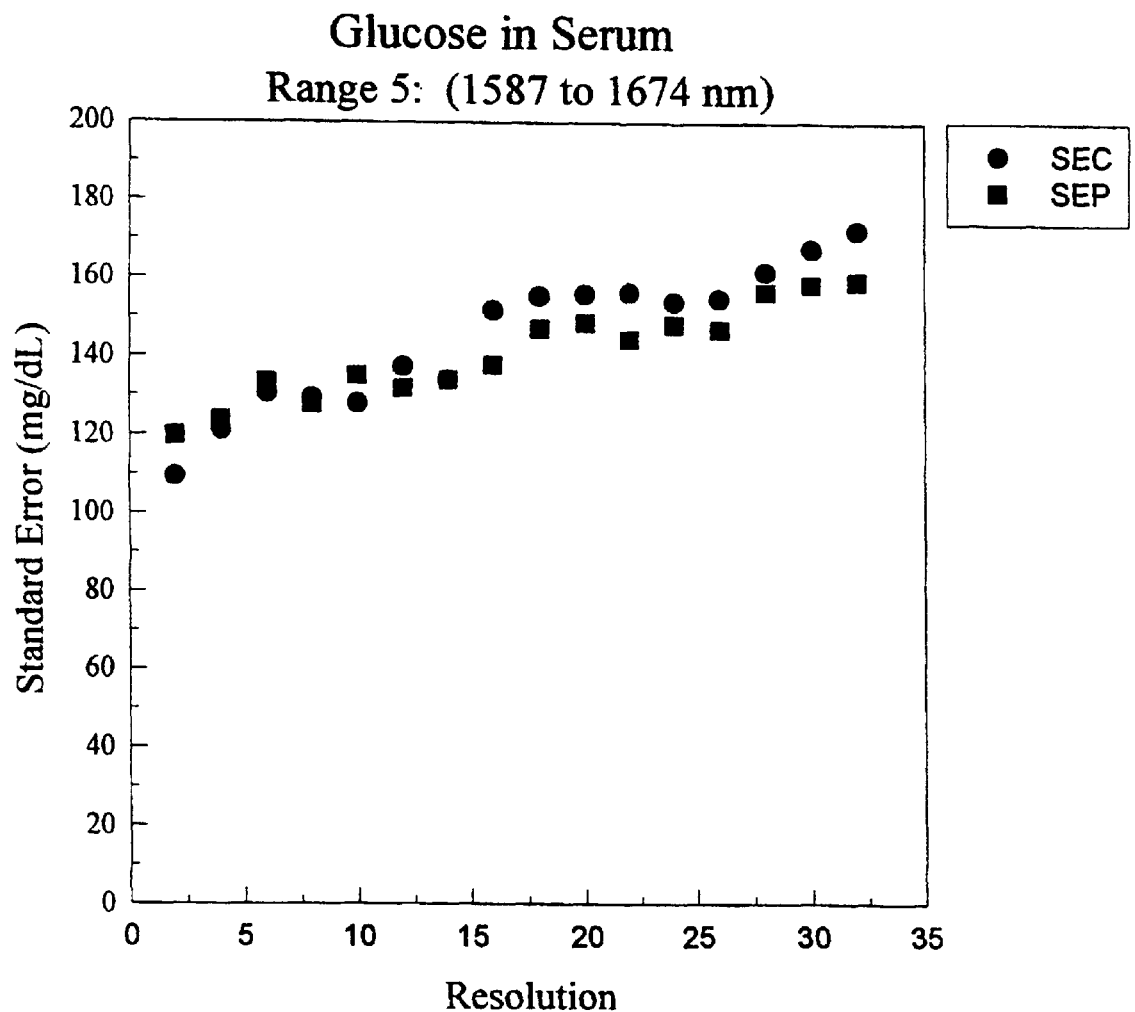
FIG. 25 is a fifth plot of standard error (mg/dL) vs. resolution (nm) for glucose in serum.
Figure 26:
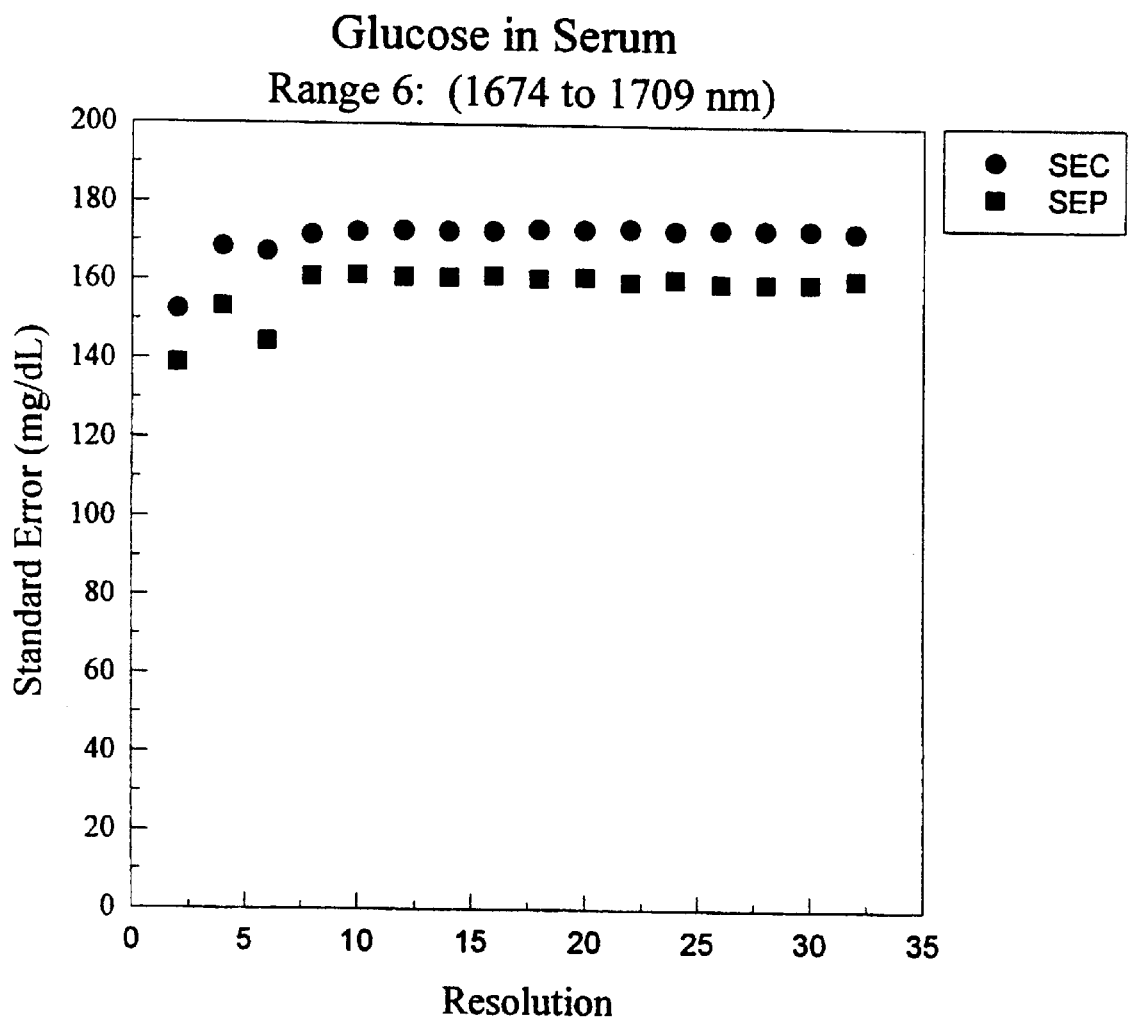
FIG. 26 is a sixth plot of standard error (mg/dL) vs. resolution (nm) for glucose in serum.
Figure 27:
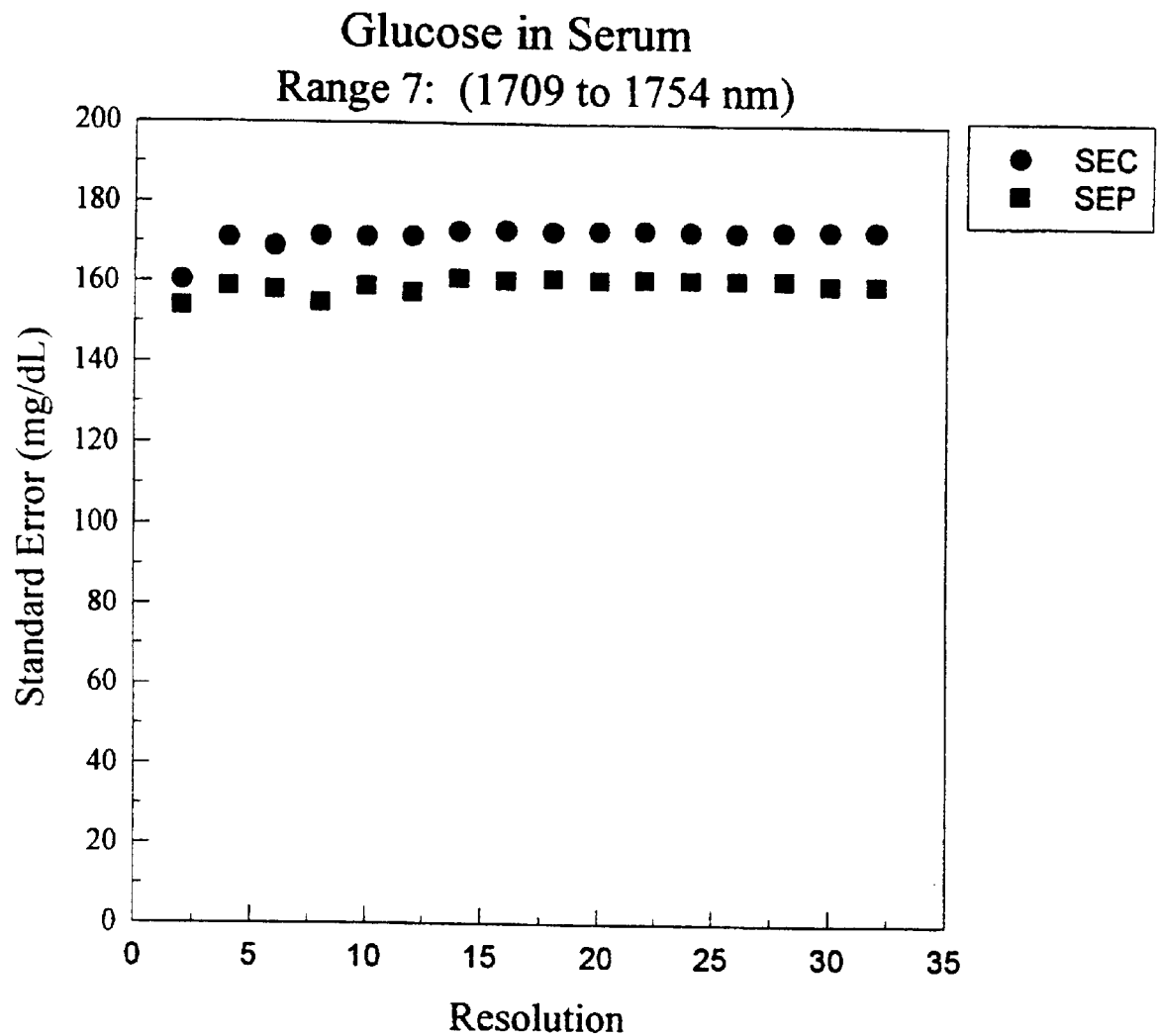
FIG. 27 is a seventh plot of standard error (mg/dL) vs. resolution (nm) for glucose in serum.
Figure 28:
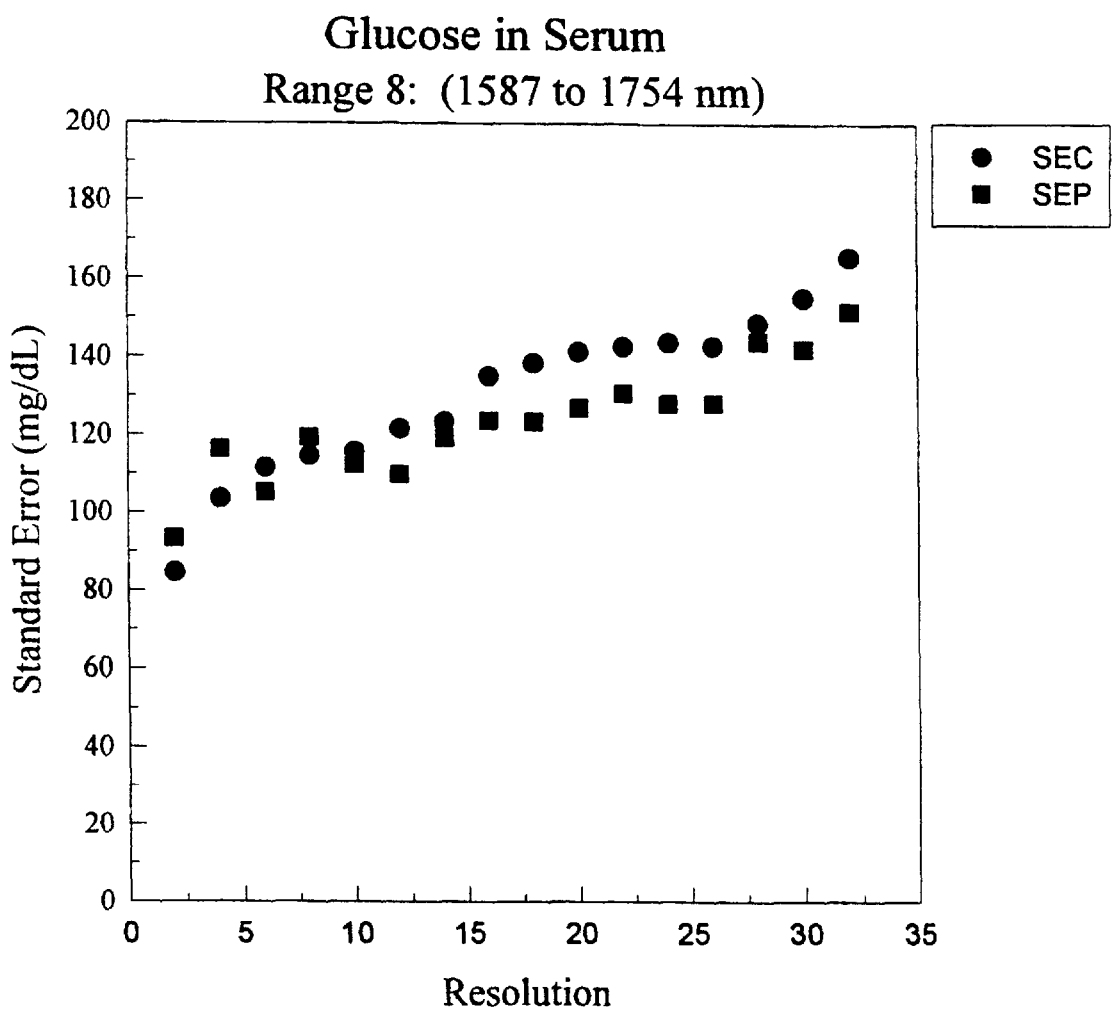
FIG. 28 is an eighth plot of standard error (mg/dL) vs. resolution (nm) for glucose in serum.

The original data set with points every two manometers was again broken down into data sets with resolution ranging from 2 to 32 nm at 2 nm intervals. This time, the data was averaged instead of just discarding extra points. For example, at 6 nm resolution points at 1100, 1102, and 1104 nm were averaged to a single point. The next point averaged the data points at 1106, 1108, and 1110 nm. The PLS analysis was then repeated and the standard errors with the tenth factor determined, as shown in FIG. 18. The increase in standard error observed with degrading resolution is observed to range from 5 to 10 mg/dL standard error as opposed to 5 to 25 mg/dL standard error from 2 to 32 nm resolution. Clearly, the failure to average the data points results in an increase of the slope of standard error versus resolution. While the standard error roughly doubles from 2 to 32 nm resolution, the data indicates that for a glucose in water solution, the acceptable resolution may be 32 nm or more. This makes chemical sense in as much as the narrowest absorbance band in this Example is 54 nm wide. In must be pointed out that there are no spectral interferences in this Example. Therefore, the actual acceptable resolution can only degrade from this resolution. 2° C. for the first overtone region, for data sets generated at 2 to 32 nm resolution using averaged data, the increase in standard error with degrading resolution is greatly reduced, as shown on FIG. 19. In addition, for this spectral region, less than ten points are retained at resolutions greater than 16 nm. The PLS algorithm used only operates on as many factors as there are data points. If queried for standard errors with additional factors, the standard error for the number of factors equal to the number of points available is generated. Because the standard errors continue to decrease with an increasing number of factors in this Example (see FIG. 17), the comparison of standard errors for various resolutions using ten PLS factors is not valid. A direct comparison of standard errors at degrading resolution for the 1587 to 1754 nm spectral region with six PLS factors is presented in FIG. 20. The increased standard error observed with degrading resolution is now not observed with resolutions under 15 nm. This is a true comparison of standard errors for this spectral region. The results in FIG. 18 for the 2078 to 2366 nm spectral region are still valid due to its large range which contains ten or more points up to 30 nm resolution.

Glucose in Serum:

The SEC and SEP plots versus resolution for glucose in the serum study for the ten different spectral regions are provided in FIGS. 21 to 30. The results are generally the same as for glucose in water.

Figure 29:
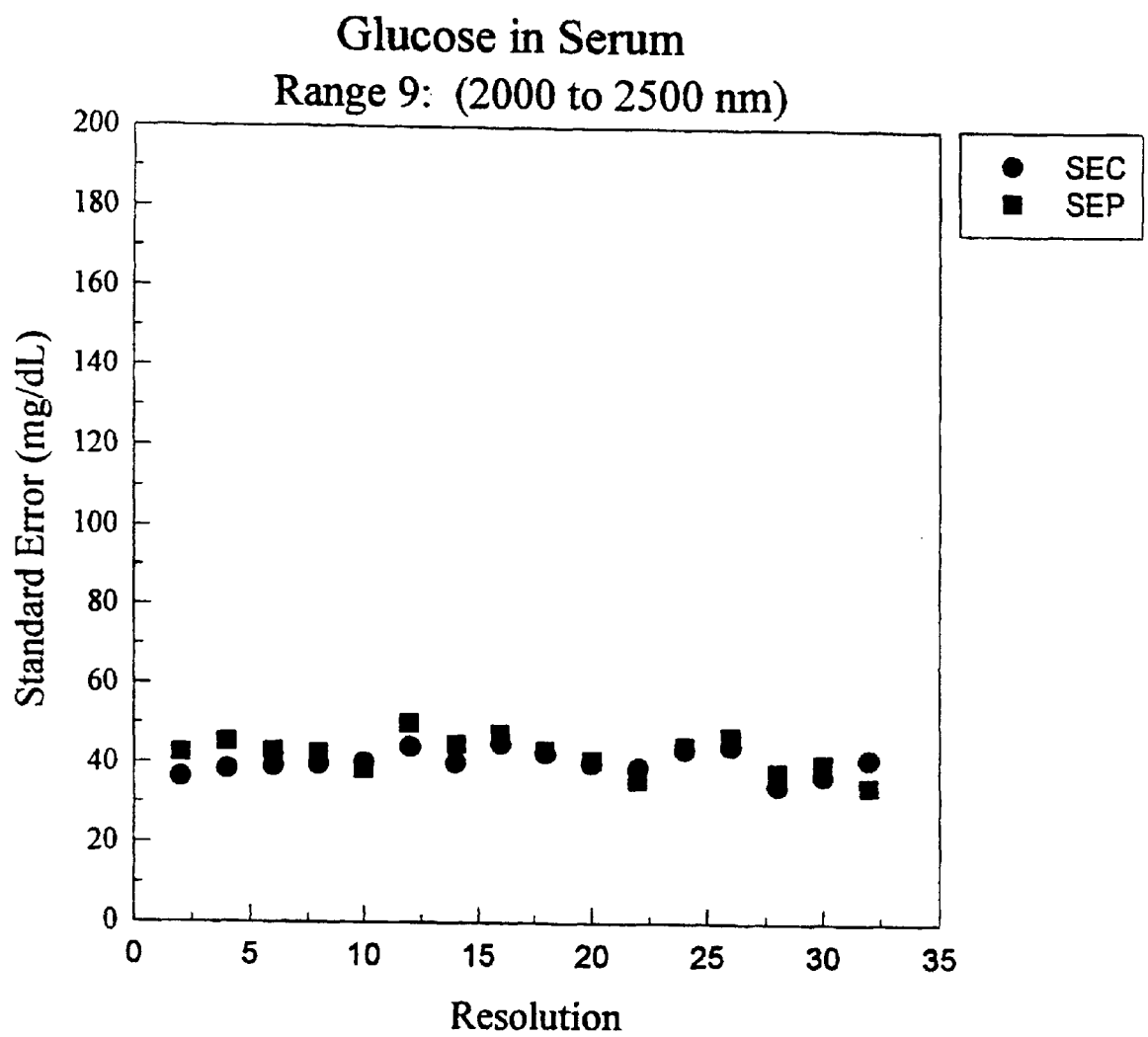
FIG. 29 is a ninth plot of standard error (mg/dL) vs. resolution (nm) for glucose in serum.

The combination band region is analyzed first. Range 1 with the largest glucose absorbance band yields the lowest standard errors for a region isolating a single glucose absorbance band, as shown on FIG. 21. Ranges 2 and 3 yield larger standard errors and have smaller glucose absorbance bands with a decreased signal to noise level, as shown on FIGS. 22 and 23. Analysis of ranges 2 and 3 at degraded resolutions is limited by the number of data points present in each range. Range 4 which couples the first three regions demonstrates the lowest standard errors, as shown on FIG. 24. Again, the averaging of points reduces the increase in standard error with degrading resolution. The increase in standard error from 35 to 50 mg/dL observed as resolution degrades from 2 to 30 nm is entirely due to the loss of information in extracting rather than averaging data points. While the standard errors are higher than in the glucose in water Example, this Example demonstrates that even in the presence of all of the spectral interferences, except skin and blood cells, the resolution is essentially not an effect until after a resolution of 30 nm. This is the same result as for glucose in water. The number of PLS factors incorporated is not an issue due to the fact that 10 points are present even at 30 nm resolution. Range 9 incorporates all of range 4 and extends past where glucose absorbs at both higher and lower frequencies, as shown in FIG. 29. No resolution effect on standard error is observed from 2 to 32 nm.

Figure 30:
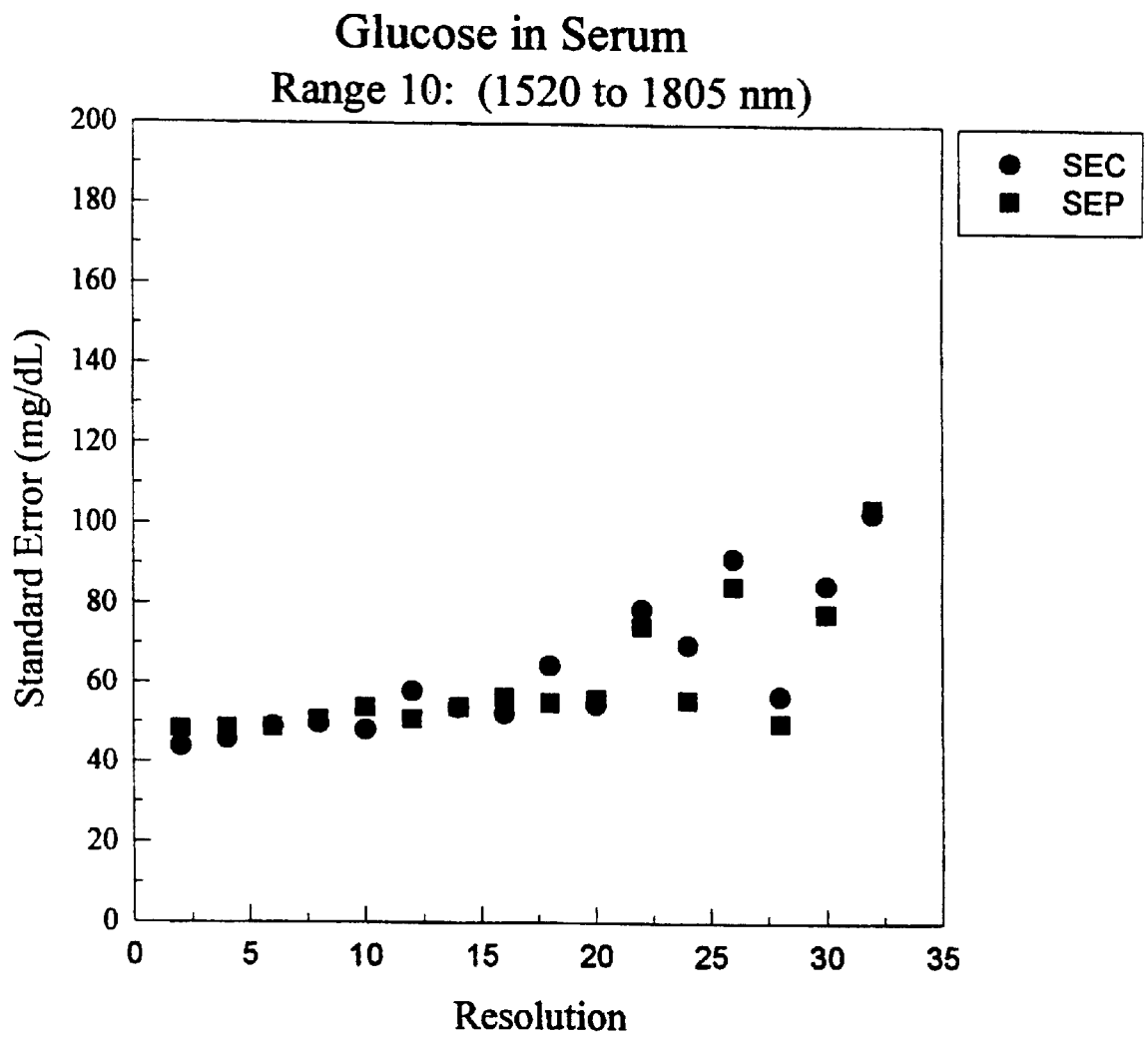
FIG. 30 is a tenth plot of standard error (mg/dL) vs. resolution (nm) for glucose in serum.
Figure 31:
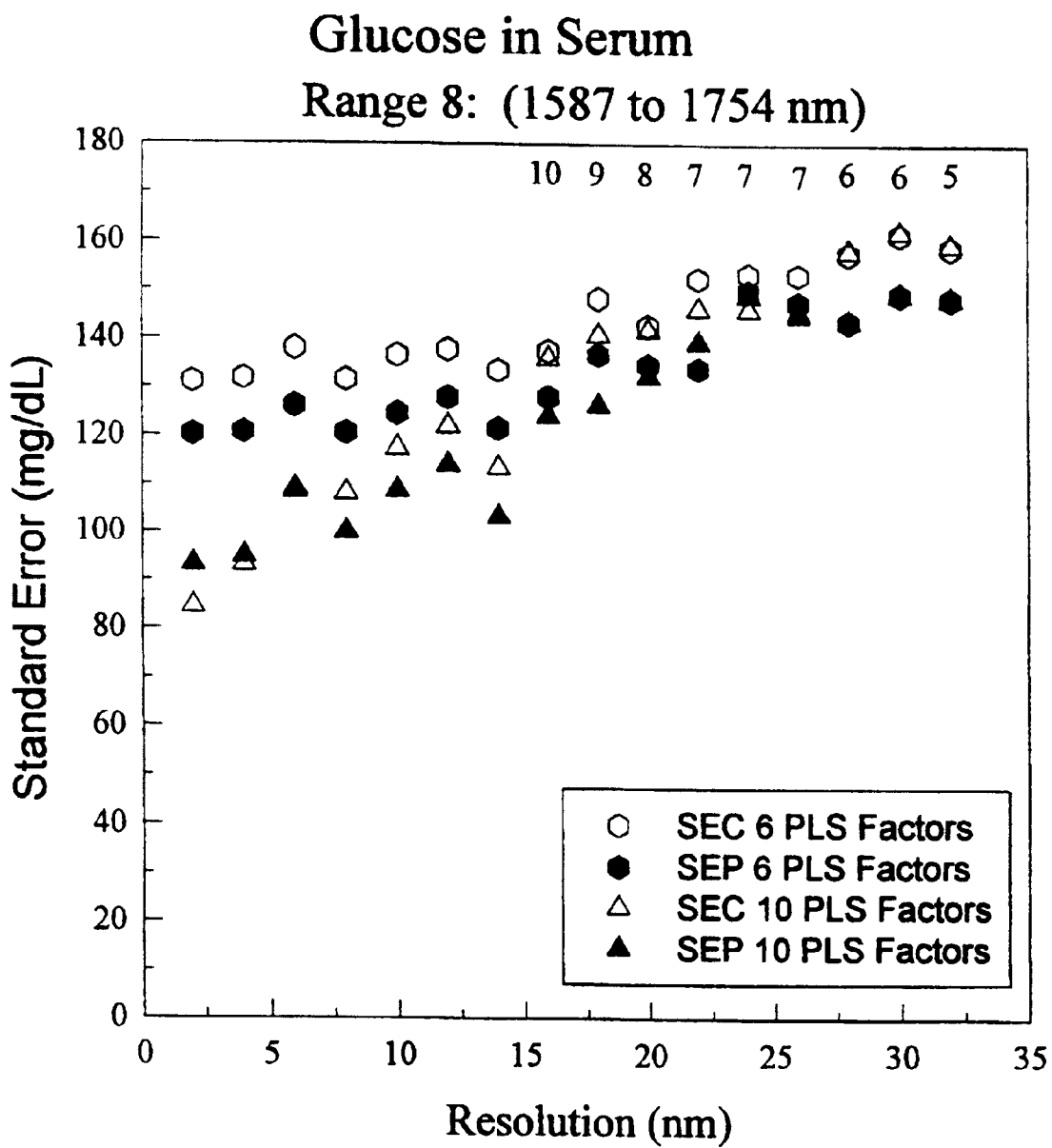
FIG. 31 is another view of the eighth plot of standard error (mg/dL) vs. resolution (nm) for glucose in serum.

The effects of resolution in the first overtone spectral region are more difficult to interpret due to decreased signal to noise and the narrower spectral ranges chosen. Range 5 has the largest glucose absorbance band in the overtone spectral window and results in the lowest standard errors. Ranges 6 and 7 were shown to have very poor signal to noise levels for glucose in water (not presented). The standard errors are essentially mean centered prediction values, as shown on FIGS. 26 and 27. The effect is worsened at degrading resolution due to the number of points in each spectral range. Range 8 reveals real glucose predictions, as shown on FIG. 28. This range was reanalyzed with the averaged rather than the selected data, see FIG. 31. Using ten PLS factors, the increasing standard error with degrading resolution observed is virtually identical to the nonaveraged data due to the number of points present in the data. This is shown by comparing the standard errors with only six PLS factors (6 points present at 30 nm resolution). No resolution effect is observed until a resolution of 20 nm. Range 10 which expands to higher and lower frequencies from range 8 has 10 data points present at 30 nm resolution and shows no resolution effect until 20 nm, as shown in FIG. 30.

Conclusions:

The glucose in water data set has sufficient signal to noise to determine glucose with the specifications required. The rise in standard error for the narrow glucose absorbance bands with degrading resolution is not real. It is partially the result of selecting the points rather than averaging the points to generate new data sets. In addition, the new data sets did not contain enough data points to compare analysis of 2 nm resolution data and 32 nm resolution data with ten PLS factors. Resolution effects may be addressed by using fewer PLS factors in this comparison or by using larger spectral ranges. For both methods, the resolution effects are minimal to 30 nm in the combination band region and 15 nm in the first overtone spectral window.

Because it is preferred to get the highest signal to noise ratio possible from the instrument, it is acceptable to have 30 nm resolution. That is, by having less (but, nonetheless, acceptable) resolution, e.g. by having 30 nm resolution instead of 10 nm resolution, the instrument captures more signal relative to noise. Thus, even though the resolution is coarser, more information is contained in signal generated by the instrument. As a result, the resolution selected in the preferred embodiment of the invention provides a more accurate picture of the spectra, even though the instrument has coarser resolution. This is because there is a higher signal to noise ratio at the resolution required. In contrast, if extra resolution were available in the instrument, but there was a lower signal to noise ratio, less information would be available for processing by the basis sets.

In the Example, the glucose in serum data sets resulted in roughly three times the standard error as in the glucose data set. Again, analysis is limited to either large spectral windows or to comparisons with fewer PLS factors for narrower ranges. In the combination band spectral region, the increase in standard error observed with degrading resolution is minimal to 30 nm resolution. In the first overtone spectral window, the slope to standard error versus resolution is minimal to 20 nm resolution. These results are virtually identical to those generated in the glucose in water study. The effects of the proteins, triglycerides, cholesterol, urea, salts, and minor organic constituents is observed not to effect the required resolution.

EXAMPLE

Basis Set V

It is necessary to measure effect of scattering of whole blood cells. This basis set is generated as follows:

Collect blood data set in transmission and as diffuse reflectance.

Repeat component extraction.

Couple in scatter correction

Deconvolve (see deconvolution discussion below).

EXAMPLE

Basis Set VI

It is necessary to measure the effect of skin. Animal studies are performed and all prior analysis techniques are repeated. Noninvasive studies can be viewed as extensions of the basis set.

Uses of Basis Sets.

Chemical and physical knowledge of a system are required for such factors as:

Intelligent wavelength selection, e.g. knowledge of the location and degree of interferences of each analyte.

Interpretation of noise levels as a function of region.

Interpretation of signal levels for each analytes as a function of wavelength.

Selection of optimal signal to noise regions for each analyte.

Resolution specifications for an instrument implementation of the invention are set forth above. The number of analog-to-digital (A/D) bits required to provide appropriate instrument resolution can be calculated from noninvasive spectra and glucose intensities (absorbance). For this determination, it is necessary to know the maximum intensity of the whole system and the intensity of glucose at the required standard error. If the maximum intensity of the sample is 10 to the negative absorbants unit, it is only necessary calculate the intensity of the body scan, including all absorbants. To determine the intensity of glucose, the required standard error is 9 mg/dL. The intensity of glucose and water, and the intensity of water is used (as described above) to calculate the intensity of the glucose and water minus the intensity of water. This results in a value for the intensity of glucose. Once the intensity of glucose is determined, it is then necessary to determine the change in intensity of glucose, e.g. by drawing in a base line to the peak, and plotting the change in intensity of glucose versus glucose concentration. This provides a best fit of the data that can be fitted to a line to calculate the change in intensity at 9 mg/dL. Once this value is obtained, the ratio of this value to maximum intensity of the glucose is readily calculated. This ratio defines the number of bits that are required in the system for analog- to-digital conversion. For example, if the ratio is 50,000, then a 16 bit A/D is required because sufficient quantization must be provided to avoid aliasing problems. Thus, the basis set is useful in defining instrument parameters.

Interpretation of multivariate results. Multivariate results are difficult to validate. Standard errors must correlate with basis set information. If noisy regions are added, the signal to noise ratio decreases. It is therefore necessary to correlate standard errors with the signal to noise ratio.

With regard to the removal of second, third, . . . order light in a grating based spectrometer, a long pass filter is required. The basis set dictates the specifications of the filter.

With regard to the removal of scatter, such determinations are based upon refractive index change. In the preferred embodiment of the invention, the basis sets remove scatter and temperature effects. This step is repeated for additional analytes, and the reduced spectra are further processed using multivariate approaches.

Deconvolution of noninvasive spectra. The partial deconvolution reduces the rank of first temperature and water, then proteins, then organic constituents. The resulting spectra can then be fed into the multivariate approaches. However, the reduced dynamic range of signals forces PLS to lock in on smaller analytes, such as urea and glucose, instead of water and temperature.

There are a limited number of interferences for glucose in the near-IR. The major interferences have convenient breaks in concentration. The largest concentrations/effects are temperature and water. Processing should remove the Refractive index, which is on the order of 100 g/dL.

Large concentration gaps exists between water and the proteins. Iterative deconvolution can be used to take advantage of this fact.

Albumin and globulin proteins are on the order of 1 to 7 g/dL. These interferants are easily identified and removed by spectral subtraction or rotation.

EXAMPLE

Linearity

Introduction:

The basis set is used to determine the location and intensity of each of the major species interfering with glucose. It also demonstrates that for a given component, the absorbance increases linearly with increasing concentration. In this Example, it is shown that the absorbance of multiple components is the sum of the individual components, as assumed by Beer's law. This is critical to the herein described approach of using spectral subtraction of chemical information to enhance the signal to noise level of glucose.

Experimental :

Spectra were collected in quadruplicate with a NIRS 5000 spectrometer configured in the transmission mode with a 1 mm pathlength quartz sample cell. All samples are reagent grade and were prepared in a 0.1 M phosphate buffer at pH 7.35 and spectra were collected at 38.0±0.2° C.

Six single analyte solutions were prepared: 4000 & 8000 mg/dL albumin, 2000 & 4000 mg/dL globulin, and 200 & 400 mg/dL triacetin. Eight additional samples were prepared consisting of all possible permutations and combinations of the above six sample concentrations. For example, one sample consisted of 8000 mg/dL albumin, 2000 mg/dL globulin, and 200 mg/dL triacetin.

Figure 32:
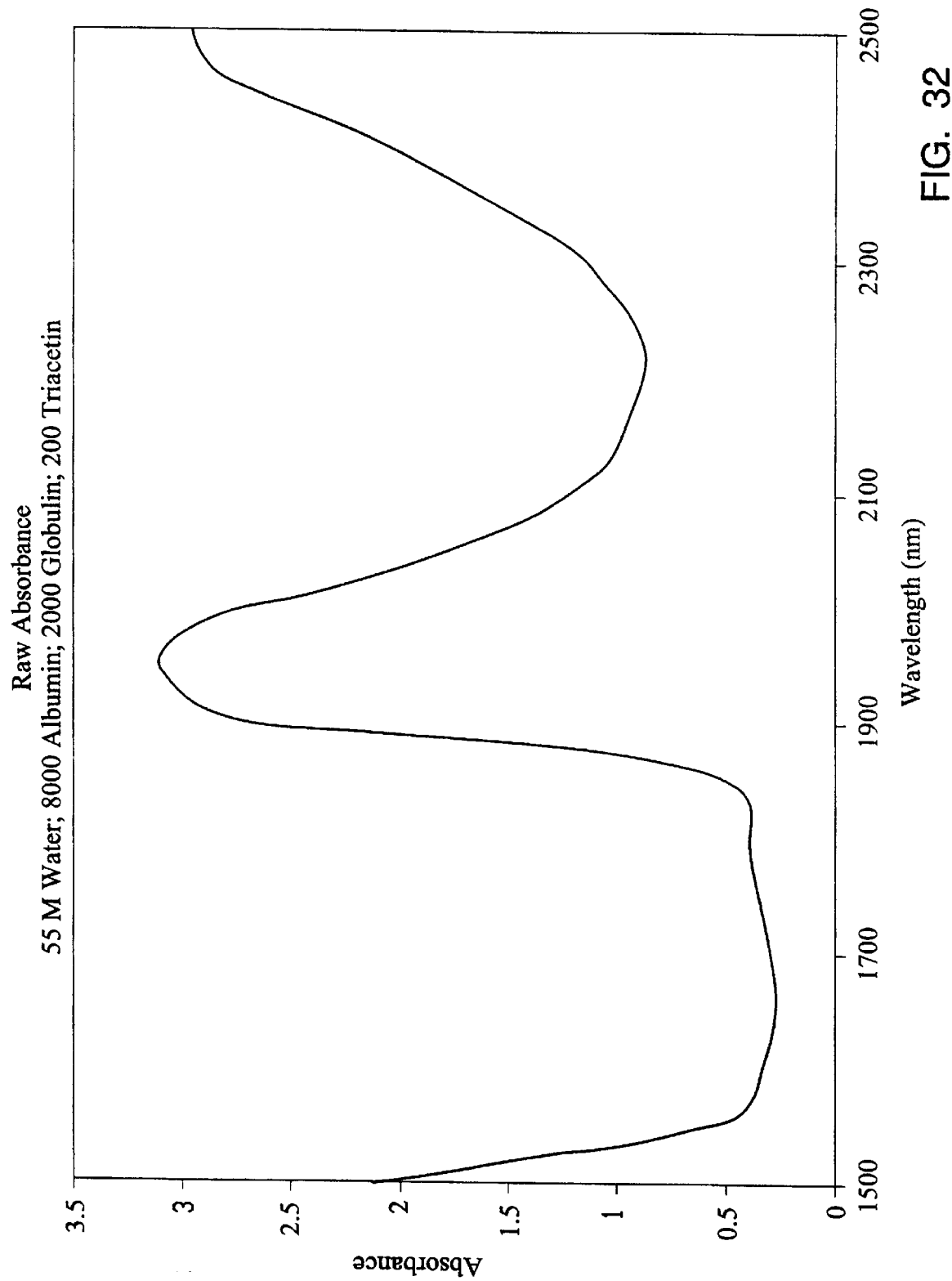
FIG. 32 is a plot of absorbance vs. wavelength showing raw absorbance for a sample containing water, albumin, globulin, and triacetin.
Figure 33:
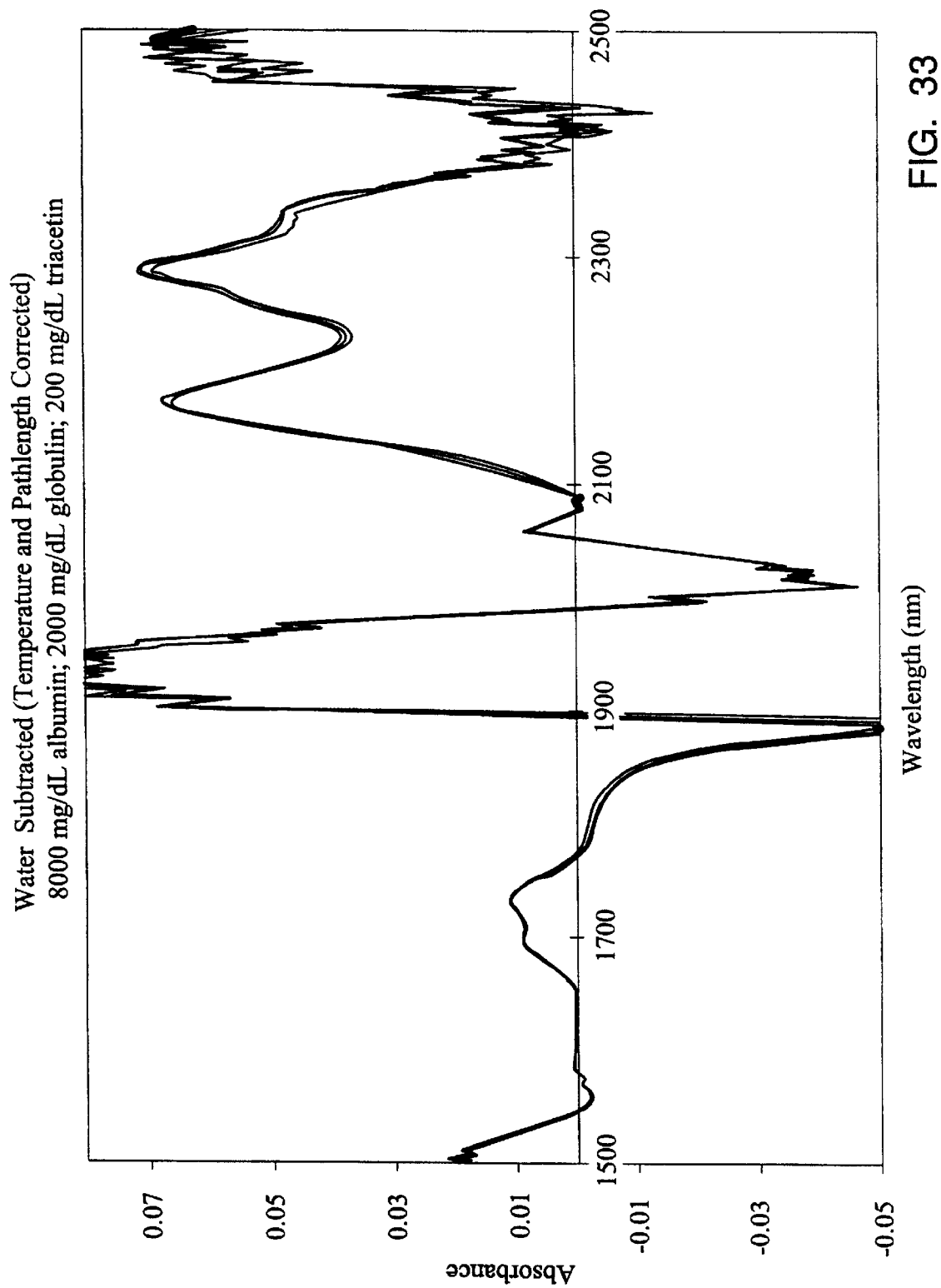
FIG. 33 is a plot of absorbance vs. wavelength for a sample containing albumin, globulin, and triacetin and from which water is subtracted and temperature and pathlength are corrected.

Results and Discussion :

Three spectra of water, 8000 mg/dL albumin, 2000 mg/dL globulin and 200 mg/dL triacetin appear primarily as water absorbance bands, as shown on FIG. 32. Subtraction of the water with the same algorithm used in the basis data set that attempts to match pathlength and temperature effects (discussed above) was employed to minimize the residual about zero absorbance over the spectral ranges 1640 to 1655 nm and 2077 to 2085 nm, as shown in FIG. 33. Results of incomplete temperature and pathlength subtraction dominate in the regions surrounding 1890 to 2010 nm where no signal results due to large water absorbance. The resulting spectra show the six dominant protein absorbance bands centered at 1690, 1730, 2060, 2170, 2285, and 2335 nm.

Figure 34:
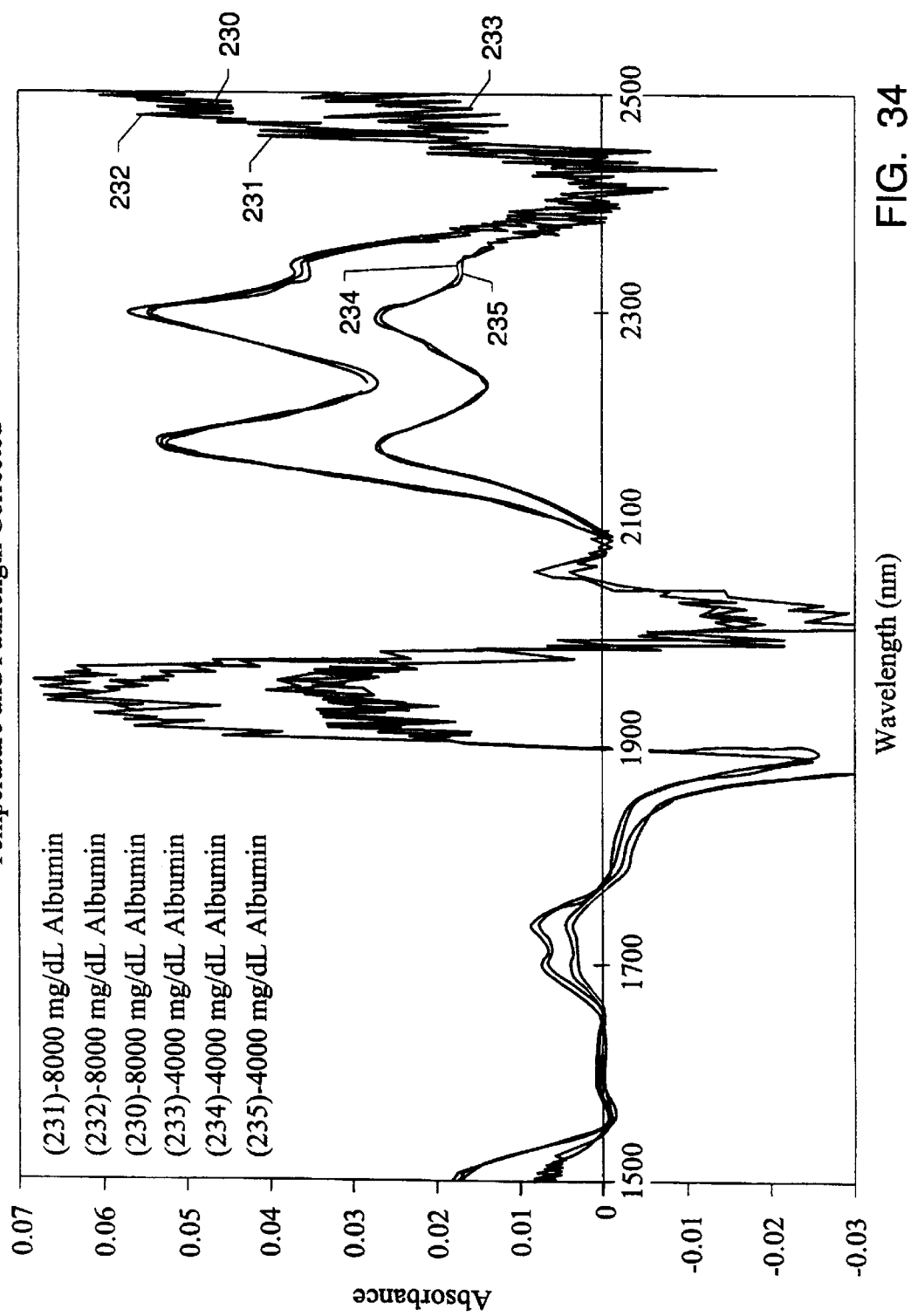
FIG. 34 is a plot of absorbance vs. wavelength showing linearity for albumin spectra where temperature and pathlength are corrected.
Figure 35:
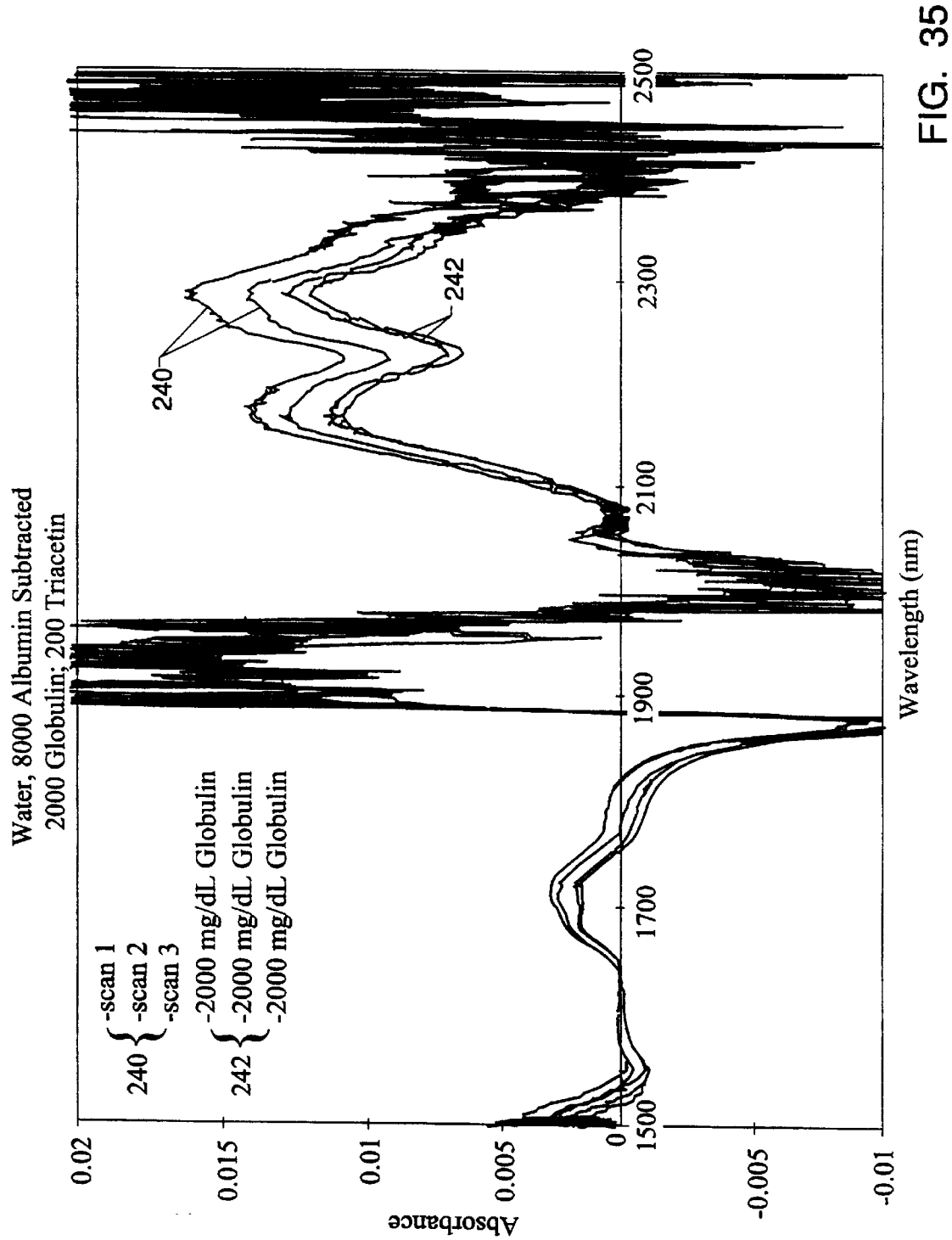
FIG. 35 is a plot of absorbance vs. wavelength for a sample containing globulin and triacetin and from which water and albumin are subtracted.

Spectra of the single analyte albumin samples are shown in FIG. 34. The 8000 mg/dL albumin peaks are nearly exactly double the 4000 mg/dL albumin peaks indicating that Beer's law is holding. The average of the 8000 mg/dL albumin spectra was subtracted from the spectra in FIG. 33 to yield the spectra shown in FIG. 35. Overlaid with this are the 2000 mg/dL globulin spectra. Clearly, the basic shape of the globulin spectra is discernible after subtraction of the 100,000 mg/dL (100 g/dL) water and the 8000 mg/dL albumin. The difference is the sum of the 200 mg/dL triacetin and baseline drift.

Figure 36:
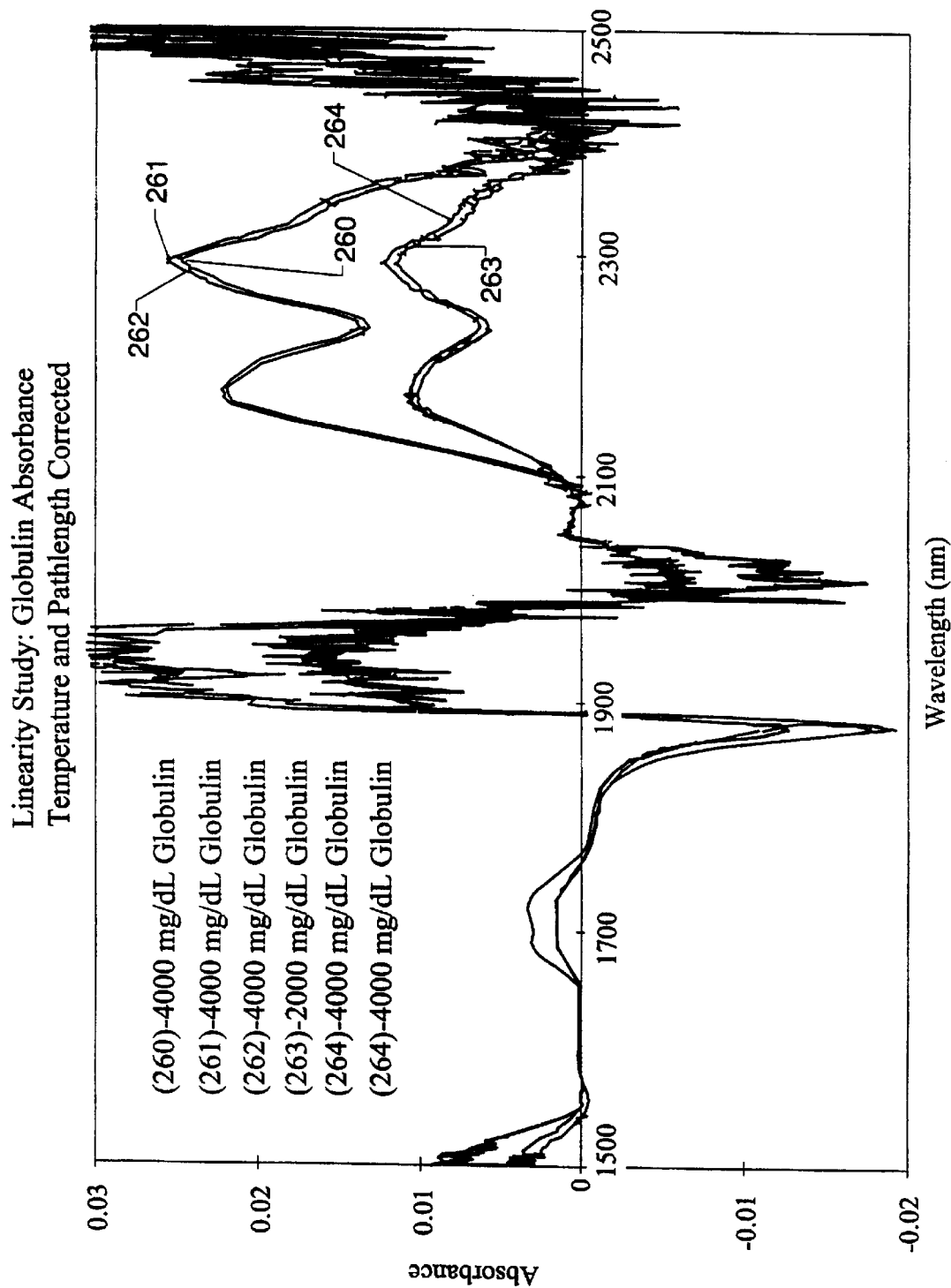
FIG. 36 is a plot of absorbance vs. wavelength showing linearity for globulin spectra where temperature and pathlength are corrected.
Figure 37:
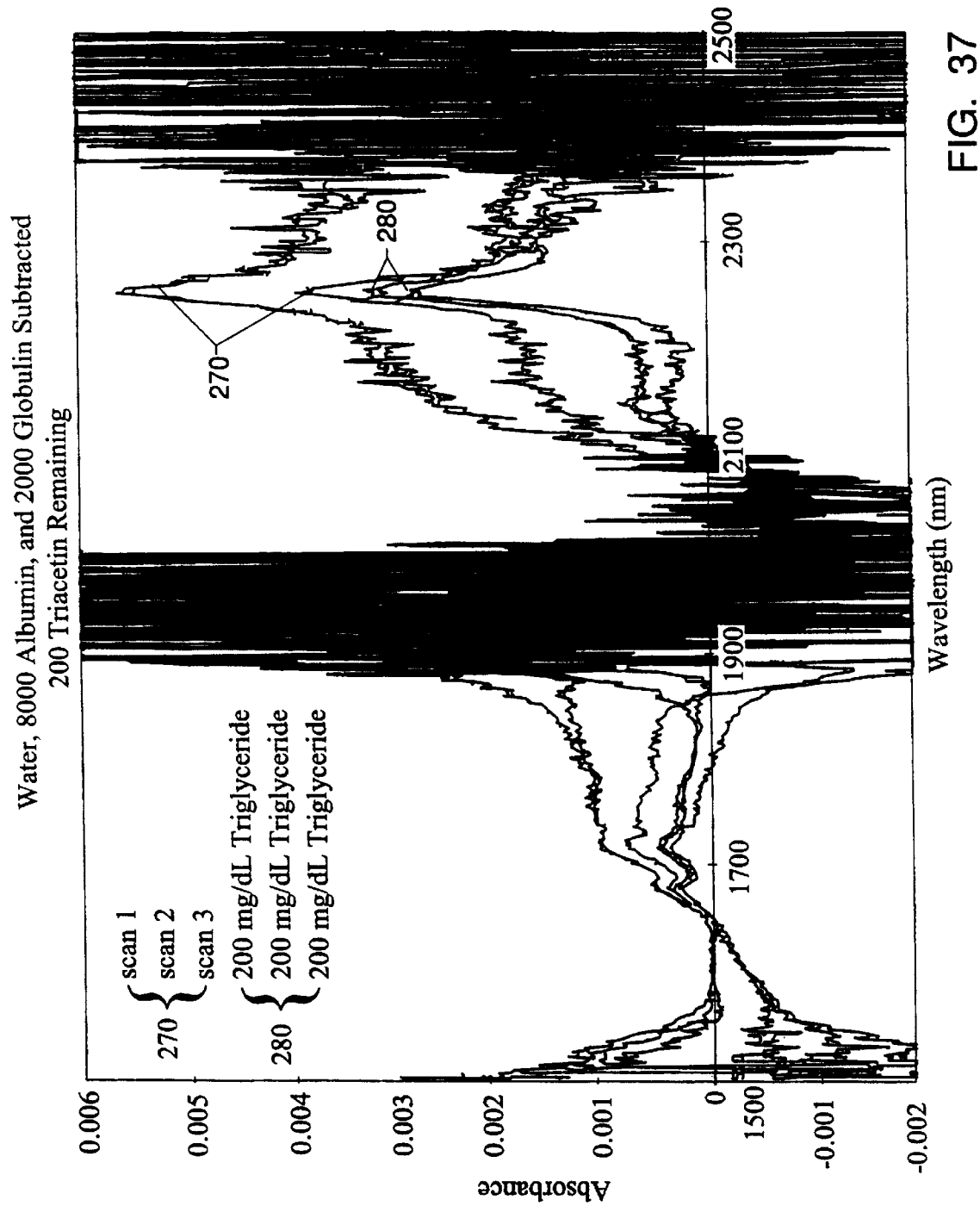
FIG. 37 is a plot of absorbance vs. wavelength for a sample containing triacetin and from which water, albumin, and globulin are subtracted.

Spectra of the single analyte globulin samples are shown in FIG. 36. The 4000 mg/dL globulin peaks (260, 261, 262) are nearly exactly double the 2000 mg/dL globulin peaks (263, 264). Again, the average of the 2000 mg/dL globulin spectra is subtracted from the spectra shown in FIG. 33 to yield the spectra in FIG. 37. Overlaid with this are the standard 200 mg/dL triacetin spectra. Once again, the 200 mg/dL triacetin peaks centered at 1675, 1715, 1760, 2130, 2250, and 2320 mg/dL can be seen after the subtraction of 100,000 mg/dL water, 8000 mg/dL albumin, and the 2000 mg/dL globulin. Unknown concentrations may be subtracted by rotation.

Conclusions:

For a relatively simple mixture, subtraction of the high concentration water, albumin, and globulin results in spectra of triacetin. Clearly, small errors in temperature and pathlength correction propagate into large errors of baseline for the lower concentration analytes. It is also possible that the error in subtraction may be due to scattering. To correct for this, a standard multiple scatter correction algorithm may be used. Clearly, straight subtraction can yield spectra that visually appear to yield higher signal to noise for the lower concentration analytes.

NOTE:

the only two species in serum that have higher near-IR absorption than glucose that were not included in this Example are cholesterol and urea.

In applying the invention, direct spectral subtraction is replaced with iterative subtraction, based upon regions of minimal or defined absorbance of remaining analytes. In another, equally preferred embodiment of the invention, another concentration gap may taken advantage of for purposes of isolating the analyte vis-a-vis interferants. Two presently preferred approaches includes:

Analyze with multivariate techniques because the dynamic range of interferences and glucose is the same; and Further removal of triglycerides, cholesterol, urea by deconvolution/ subtraction.

One approach to generating basis sets is iterative. For example, within a sample, after subtracting water, a determination of albumin and globulin is made. Once albumin and globulin are determined, and there is knowledge of water concentration, the albumin and globulin may be again removed, only this time more accurately. This iterative process proceeds to some predetermined limit of precision, and then triglycerides and cholesterol are integrated into the analysis.

Although the invention is described herein with reference to the preferred embodiment, one skilled in the art will readily appreciate that other applications may be substituted for those set forth herein without departing from the spirit and scope of the present invention. Accordingly, the invention should only be limited by the Claims included below.

What is claimed is:

1. A method for determining the concentration of a target analyte in a sample using multi-spectral analysis, comprising the steps of:

generating at least one basis set that includes at least one interfering component in said sample; and applying a spectroscopic signal representative of said sample to said basis set;

wherein a component of said sample corresponding to said analyte is identified by application of said basis set.

2. The method of claim 1, wherein said sample is serum; and wherein said basis set comprises interfering components that include any of water, temperature/hydrogen effects, bonding effects, albumin, globulin, protein, triglycerides, cholesterol, urea, scatter correction, refractive index correction, depth of penetration, and organic, body, and physical components.

3. The method of claim 1, wherein said basis set does not include those components that do not interfere with detection of said analyte.

4. The method of claim 1, further comprising the step of: identifying all relevant interfering components.

5. The method of claim 4, further comprising the step of: determining how each of said interfering components interact.

6. The method of claim 5, further comprising the step of: extracting each of said interfering components.

7. The method of claim 6, further comprising the step of: comparing spectra for each of said interfering components with that of each of said interfering components in solution.

8. The method of claim 1, wherein a basis set is sequentially and iteratively generated for each of said interfering components.

9. The method of claim 8, further comprising the step of: combining said basis sets mathematically to generate a set of transforms that may be stored in a look-up table for use during analysis.

10. The method of claim 1, further comprising the steps of:

characterizing each of said interfering components in said sample; and subtracting each of said interfering components from spectra produced at a frequency of interest.

11. The method of claim 1, further comprising the steps of:

applying said basis set to a first signal produced during said multi-spectral analysis to identify a second signal representative of said analyte;

applying multivariate analysis to said second signal.

12. The method of claim 11, wherein said multivariate analysis comprises a partial least squares analysis, followed by a principal components analysis.

13. A method generating at least one basis set for application in determining the concentration of a target analyte in a sample using multi-spectral analysis, said method comprising the steps of:

identifying at least one relevant interfering component of said sample at a same frequency as that of said analyte;

identifying said at least one relevant interfering component at other frequencies to quantify absorbance of said interfering components at said other frequencies; and removing said at least one interfering component at said analyte frequency.

14. The method of claim 13, wherein each step of said method is repeated for each of said at least one interfering component to produce a plurality of basis sets for an analyte.

15. The method of claim 13, further comprising the step of:

determining the concentration of said target analyte in said sample with said basis set by:

collecting spectra data with a spectroscopic device;

converting said spectral data collected by said spectroscopic device to digital data;

operating upon such digital input data in accordance with various transforms stored in one or more lookup tables (LUTs), wherein said LUTs contain transforms that incorporate said basis set, and wherein said transforms use said basis set to identify and remove interfering constituents from the spectral signal produced by said spectroscopic device.

16. The method of claim 15, wherein said basis set is applied before or in connection with a physical model that corrects for interfering physical factors that include any of scattering, pathlength, and temperature.

17. The method of claim 13, further comprising the step of:

storing said basis set in a lookup table.

18. The method of claim 13, said basis set comprising:

a series of spectra of said analyte at different physiological concentrations of interest.

19. The method of claim 13, further comprising the step of:

providing a plurality of basis sets that are used to quantify an analyte in a liquid sample.

20. The method of claim 13, further comprising the step of:

selecting different pathlengths for each spectral window.

21. The method of claim 20, wherein said pathlengths comprise:

about 1 mm for a combination band region;

about 2 to 8 mm for a first overtone region; and about 10 mm or greater for a second overtone region.

22. The method of claim 13, wherein one or more basis sets are applied to a spectroscopic signal during analysis to produce an accurate spectral representation from which analyte concentration may be accurately determined.

23. The method of claim 13, wherein said basis set includes all interfering components found in said sample.

24. An apparatus for determining the concentration of a target analyte in a sample using multi-spectral analysis, comprising:

at least one basis set that includes at least one interfering component in said sample;

wherein a spectroscopic signal representative of said sample is applied to said basis set; and wherein a component of said sample corresponding to said analyte is identified by application of said basis set.

25. The apparatus of claim 24, wherein said sample is serum; and wherein said basis set comprises interfering components that include any of water, temperature/hydrogen effects, bonding effects, albumin, globulin, protein, triglycerides, cholesterol, urea, scatter correction, refractive index correction, depth of penetration, and organic, body, and physical components.

26. The apparatus of claim 24, wherein said basis set does not include those components that do not interfere with detection of said analyte.

27. The apparatus of claim 24, said basis set further comprising:

all relevant interfering components.

28. The apparatus of claim 27, wherein said basis set is generated by determining how each of said interfering components interact.

29. The apparatus of claim 28, wherein said basis set is further generated by extracting each of said interfering components.

30. The apparatus of claim 29, wherein said basis set is further generated by comparing spectra for each of said interfering components with that of each of said interfering components in solution.

31. The apparatus of claim 24, further comprising:

a basis set is for each of said interfering components.

32. The apparatus of claim 31, said basis set further comprising:

a mathematically generated set of transforms that may be stored in a look-up table for use during analysis.

33. The apparatus of claim 24, wherein said basis set is generated by characterizing each of said interfering components in said sample; and subtracting each of said interfering components from spectra produced at a frequency of interest.

34. The apparatus of claim 24, wherein said basis set is applied to a signal produced during said multi-spectral analysis to identify a signal representative of said analyte; and wherein multivariate analysis is applied to said signal.

35. The apparatus of claim 34, wherein said multivariate analysis comprises a partial least squares analysis, followed by a principal components analysis.

36. A tangible medium embodying computer executable code comprising a basis set for application in determining the concentration of a target analyte in a sample using multi-spectral analysis, said basis set comprising a computer implemented method for:

collecting and storing spectral information representative of relevant interfering components of said sample at a same frequency as that of said analyte;

collecting and storing spectral information representative of substantially all of said relevant interfering components at other frequencies;

quantifying absorbance of said interfering components at said other frequencies;

receiving a signal corresponding to a spectroscopic signal representative of said sample; and removing spectral information of said interfering components from a sample spectra at said analyte frequency.

37. The medium of claim 36, further comprising:

a plurality of basis sets for an analyte.

38. The medium of claim 36, in combination with:

an instrument for determining the concentration of said target analyte in said sample with said basis set, said instrument comprising:

a spectroscopic device for collecting spectra data;

an analog-to-digital converter for converting said spectral data collected b y said spectroscopic device to digital data;

a processor for operating upon such digital input data in accordance with various transforms stored in one or more look-up tables (LUTs), wherein said LUTs contain transforms that incorporate said basis set, and wherein said transforms use said basis set to identify and remove substantially all interfering constituents from the spectral signal produced by said spectroscopic device.

39. The medium of claim 38, wherein said basis set is applied before or in connection with a physical model that corrects for interfering physical factors that include any of scattering, pathlength, and temperature.

40. The medium of claim 36, wherein said basis set is stored h a lookup table.

41. The medium of claim 36, said basis set comprising:

a series of spectra of said analyte at different physiological concentrations of interest.

42. The medium of claim 36, further comprising:

a plurality of basis sets that are used to quantify an analyte in a liquid sample.

43. The medium of claim 36, wherein different pathlengths are selected for each spectral window.

44. The medium of claim 43, wherein said pathlengths comprise:
   about 1 mm for a combination band region;
   about 5 to 10 mm for a first overtone region; and
   about 10 mm or greater for a second overtone region.

45. The medium of claim 36, wherein one or more basis sets are applied to a spectroscopic signal during analysis to produce an accurate spectral representation from which analyte concentration may be accurately determined.

46. The medium of claim 36, wherein said basis set includes all interfering components found in said sample.

47. The medium of claim 36, wherein said spectral information is non invasively collected.

* * * * *